US009708356B2

(12) United States Patent
Nakagame et al.

(10) Patent No.: US 9,708,356 B2
(45) Date of Patent: Jul. 18, 2017

(54) METHOD FOR MANUFACTURING MONOSACCHARIDES, OLIGOSACCHARIDES, AND FURFURALS FROM BIOMASS

(71) Applicant: Oji Holdings Corporation, Chuo-ku, Tokyo (JP)

(72) Inventors: Seiji Nakagame, Tokyo (JP); Nobuhisa Dano, Tokyo (JP); Takayuki Obuchi, Tokyo (JP); Shinya Hagiwara, Tokyo (JP); Yosuke Uchida, Tokyo (JP); Koki Kisara, Tokyo (JP); Tomoaki Sasaki, Tokyo (JP)

(73) Assignee: Oji Holdings Corporation, Tokyo (JP)

( * ) Notice: Subject to any disclaimer, the term of this patent is extended or adjusted under 35 U.S.C. 154(b) by 594 days.

(21) Appl. No.: 14/360,387

(22) PCT Filed: Nov. 2, 2012

(86) PCT No.: PCT/JP2012/078460
§ 371 (c)(1),
(2) Date: May 23, 2014

(87) PCT Pub. No.: WO2013/080742
PCT Pub. Date: Jun. 6, 2013

(65) Prior Publication Data
US 2014/0288298 A1    Sep. 25, 2014

(30) Foreign Application Priority Data

Nov. 30, 2011  (JP) .................................. 2011-261364
Dec. 28, 2011  (JP) .................................. 2011-288978
(Continued)

(51) Int. Cl.
*C13K 13/00*     (2006.01)
*C07H 1/08*      (2006.01)
(Continued)

(52) U.S. Cl.
CPC .............. *C07H 1/08* (2013.01); *C07D 307/50* (2013.01); *C07H 3/02* (2013.01); *C07H 3/06* (2013.01);
(Continued)

(58) Field of Classification Search
CPC . D21H 11/02; C13K 1/02; C13K 1/04; C13K 13/00; C13K 13/002; C13K 13/02;
(Continued)

(56) References Cited

U.S. PATENT DOCUMENTS 3,354,029 A * 11/1967 Aurell ..................... D21C 3/22
                                              162/41
3,475,271 A * 10/1969 Laakso .................... D21C 7/00
                                              162/242
4,436,586 A *  3/1984 Elmore .................... C12P 7/10
                                              162/19

FOREIGN PATENT DOCUMENTS

JP          30-8066 B1      11/1955
JP         37-3724 B1       6/1962
(Continued)

*Primary Examiner* — David M Brunsman
(74) *Attorney, Agent, or Firm* — Foley & Lardner LLP

(57) ABSTRACT

The present invention provides a method for efficiently producing monosaccharides, oligosaccharides, and furfurals from biomass. A biomass is hydrolyzed under conditions under which monosaccharides, oligosaccharides, and furfurals are produced while continuously supplying an aqueous suspension of the biomass from a supply port of a continuous primary hydrolysis device and moving the suspension through the device. A hydrolysis solution is continuously discharged from a discharge port of the continuous hydrolysis device, and a hydrolysis solution containing monosaccharides, oligosaccharides, and furfurals are extracted from an intermediate extraction port provided at any position between the supply port and the discharge port of the continuous primary hydrolysis device. The extracted hydrolysis solution is then subjected to secondary hydrolysis.

15 Claims, 31 Drawing Sheets

(30) Foreign Application Priority Data

| | | |
|---|---|---|
| Mar. 7, 2012 | (JP) | 2012-050849 |
| Mar. 30, 2012 | (JP) | 2012-078499 |
| Apr. 17, 2012 | (JP) | 2012-093459 |
| Jul. 12, 2012 | (JP) | 2012-156062 |
| Jul. 23, 2012 | (JP) | 2012-162834 |
| Jul. 26, 2012 | (JP) | 2012-165359 |
| Oct. 12, 2012 | (JP) | 2012-226726 |

(51) Int. Cl.

| | |
|---|---|
| *C07H 3/02* | (2006.01) |
| *C07H 3/06* | (2006.01) |
| *C07D 307/50* | (2006.01) |
| *C13K 1/04* | (2006.01) |
| *C13K 1/02* | (2006.01) |
| *D21C 1/02* | (2006.01) |
| *D21C 3/02* | (2006.01) |
| *D21C 11/00* | (2006.01) |
| *C08H 8/00* | (2010.01) |

(52) U.S. Cl.
CPC .......... *C08H 8/00* (2013.01); *C13K 1/02* (2013.01); *C13K 1/04* (2013.01); *C13K 13/00* (2013.01); *C13K 13/002* (2013.01); *D21C 1/02* (2013.01); *D21C 3/02* (2013.01); *D21C 11/0007* (2013.01)

(58) Field of Classification Search
CPC ... C07H 1/08; C07H 3/02; C07H 3/06; C07D 307/50
See application file for complete search history.

(56) References Cited

FOREIGN PATENT DOCUMENTS

| | | |
|---|---|---|
| JP | 37-11135 B1 | 8/1962 |
| JP | 58-126387 A | 7/1983 |
| JP | 2006-043504 A | 2/2006 |
| JP | 2009-517553 A | 4/2009 |
| JP | 2010-253348 A | 11/2010 |
| JP | 2011-103874 A | 6/2011 |
| WO | WO 2007/064293 A1 | 6/2007 |

\* cited by examiner

Ratio (%) a: ratio (%) of unreacted sugar after secondary hydrolysis
(after secondary hydrolysis / before secondary hydrolysis) x 100

Ratio (%) a: ratio (%) of unreacted sugar after secondary hydrolysis
(after secondary hydrolysis / before secondary hydrolysis) x 100

Ratio (%) a: ratio (%) of unreacted sugar after secondary hydrolysis
(after secondary hydrolysis / before secondary hydrolysis) x 100

METHOD FOR MANUFACTURING MONOSACCHARIDES, OLIGOSACCHARIDES, AND FURFURALS FROM BIOMASS

CROSS-REFERENCE TO RELATED APPLICATIONS

This application is a National Stage application of PCT/JP2012/078460, filed Nov. 2, 2012, which claims priority from Japanese patent application nos. JP 2011-261364, filed Nov. 30, 2011, JP 2011-288978, filed Dec. 28, 2011; JP 2012-050849, filed Mar. 7, 2012; JP 2012-078499, filed Mar. 30, 2012; JP 2012-093459, filed Apr. 17, 2012; JP 2012-156062, filed Jul. 12, 2012; JP 2012-162834, filed Jul. 23, 2012; JP 2012-165359, filed Jul. 26, 2012; and JP 2012-226726, filed Oct. 12, 2012.

TECHNICAL FIELD

The present invention relates to a method for efficiently manufacturing monosaccharides, oligosaccharides, and/or furfurals by performing continuous primary hydrolysis on a biomass and performing secondary hydrolysis on the primary hydrolysis solution obtained by continuous primary hydrolysis.

BACKGROUND ART

A biomass resource is an organic resource which is produced by photosynthesis from water, carbon dioxide, and solar energy and can be utilized as an energy source or a chemical raw material. If the production volume of the product produced from a biomass resource and the amount of the product that is used can be harmonized, a biomass resource is a renewable resource that can be used without increasing carbon dioxide emissions.

Biomass refers to "waste biomass", which is organic waste that is discharged as unnecessary substances in processes involving life or industrial activities, "unused biomass" such as non-edible parts of crops plowed into farmland or left in the forest (for example, the stems/leaves of corn) or timber from forest thinning, "resource crops", which are plants grown in currently fallow land or unused land for the purpose of obtaining material and energy resources rather than producing food or wood, "new crops" that are resource crops having functions such as productivity improved by breeding using conventional methods and genetic recombination techniques, and the like.

Biomass is composed of components such as cellulose, hemicellulose, lignin, and intracellular components, and the component ratio differs depending on the type of biomass. For example, wood-based biomass is composed of approximately 50% cellulose, from 20 to 25% hemicellulose, from 20 to 25% lignin, and approximately 5% intracellular components. These components can be used industrially.

For example, cellulose can be used as a paper pulp or a dissolving pulp. Further, since cellulose is a polymer of glucose, it is possible to obtain glucose or cellooligosaccharide from cellulose. Glucose can be used as a raw material for the fermentation of ethanol or lactic acid, and cellooligosaccharide can be used as a functional food. A sugar alcohol obtained by reducing glucose (sorbitol) is widely used as a sweetener providing a cool sensation and has attracted attention in recent years as a biomass-derived plastic raw material (Non-Patent Document 1).

On the other hand, hemicellulose is a polymer heteropolysaccharide composed of xylan, mannan, galactan, or the like and is formed from xylose, arabinose, mannose, galactose, or the like. A monosaccharide such as xylose or arabinose or an oligosaccharide such as a xylooligosaccharide can be obtained from hemicellulose. In addition, like glucose, monosaccharides such as xylose can also be used as a raw material for fermentation. Xylitol, which is obtained by reducing xylose, is incorporated into infusions for diabetic patients and into chewing gum and the like as a sweetener less likely to cause tooth decay. Mannitol, which is obtained by reducing mannose, is also used as a sweetener, and a diuretic effect, an effect of lowering intracranial pressure by opening the brain barrier, and an effect of promoting the transport of drugs into the brain have been reported (Non-Patent Document 2).

Further, a pentose such as xylose or arabinose can be converted to a furfural, and a hexose such as glucose or mannose can be converted to 5-hydroxymethylfurfural. These furfurals can be used as intermediates of pharmaceuticals, raw materials for plastics, or raw materials for furfuryl alcohols (raw materials for furan resins). 2,5-furandicarboxylic acid, which is obtained by oxidizing 5-hydroxymethylfurfural, is expected to be used as a polyester monomer as an alternative substance to terephthalic acid. In addition, 2,5-dimethylfuran, which is obtained by the hydrogenolysis of 5-hydroxymethylfurfural, is expected to be used as an alternative fuel to gasoline. The United States Department of Energy cites 12 types of chemical products such as xylitol, sorbitol, and 2,5-furandicarboxylic acid as chemical products that can be developed from biomass resources using bio-processes as key technologies and that are highly likely to be established as an industry (Non-Patent Document 3).

The components constituting a biomass can be decomposed and extracted by subjecting the biomass to pressurized hot water treatment. Pressurized hot water is in a high-temperature, high-pressure liquid state that has a temperature of 100 to 374° C. and is pressurized to saturated steam pressure or higher. The components of the biomass can be separated by utilizing the difference in reactivity of the biomass components with respect to the pressurized hot water. For example, it has been reported that when the temperature of the pressurized hot water is from 100 to 140° C., it is possible to recover intracellular useful components (tannins, terpenes, and organic acids) or water-soluble lignin. In addition, it has been reported that when the temperature of the pressurized hot water is from 140 to 230° C., it is possible to recover oligosaccharides derived from hemicellulose or monosaccharides such as xylose, arabinose, mannose, and galactose (Patent Document 1, Non-Patent Documents 4 to 6).

Of the types of pressurized hot water treatment described above, a pressurized hot water treatment used as a pre-process of a kraft cooking method when producing dissolving pulp is called a prehydrolysis step. In order to produce dissolving pulp from biomass, it is necessary to selectively remove the lignin and hemicellulose in the biomass to enhance the cellulose purity. Prehydrolysis in the production of pulp is performed under conditions under which the decomposition of cellulose is suppressed and only hemicellulose is decomposed. In the prehydrolysis step, simply adding water to the biomass and heating causes the desorption of acetyl groups in hemicellulose and produces acetic acid, which causes the biomass to become acidic and promotes acidic hydrolysis. Mannose, glucose, and galactose which are hexoses, and xylose and arabinose, which are pentoses, are contained as constituent sugars in the hemicellulose.

In the prehydrolysis step, oligosaccharides consisting of the sugars described above are produced when hemicellulose is hydrolyzed. In addition, monosaccharides are produced when the hydrolysis of the oligosaccharides progresses further. Among these sugars, xylose and aribinose, which are pentoses, are converted to furfurals by a dehydration reaction of three molecules of water (Non-Patent Document 7). In the hydrolysate (solid content) after the biomass is subjected to prehydrolysis, the lignin and hemicellulose remaining in the hydrolysate in the kraft cooking process of a subsequent stage are removed, and high-purity cellulose (dissolving pulp) is obtained by further performing bleaching treatment in the next step.

As described above, the primary objective of the prehydrolysis step is to efficiently produce dissolving pulp (cellulose), so prehydrolysis is performed under conditions suitable for the production of dissolving pulp. Water is typically added to the raw material chips (absolute dry weight) at a liquid ratio of approximately 2 to 5 and processed for one to several hours at 150° C. to 180° C. In addition, suitable prehydrolysis conditions are set in accordance with the type of the raw material and the quality of the target dissolving pulp. Accordingly, the ratio of oligosaccharides, monosaccharides, and furfurals contained in the reaction liquid after prehydrolysis is not the target ratio, so there is a problem in that it is not possible to efficiently produce the components of interest. If it were possible to arbitrarily control the production ratio of oligosaccharides, monosaccharides, and furfurals derived from hemicellulose, it would be possible to produce the components in accordance with the demand thereof. When aiming for practical application at an industrial scale, this is advantageous from an economical perspective since it is possible to efficiently produce only the necessary components of interest. Further, if it were possible to improve the production efficiency of the oligosaccharides, monosaccharides, and furfurals derived from hemicellulose in the prehydrolysis conditions used for the dissolving pulp, this would enable the production of dissolving pulp as well as the practical application of the monosaccharides, oligosaccharides and furfurals contained in the hydrolysis solution at an industrial scale.

As techniques for controlling the production volume of products by means of pressurized hot water treatment using biomass as a raw material, a method of controlling the ratio of the production volumes of the hemicellulose degradation product and the cellulose degradation product by changing the amount of pressurized hot water supplied to the biomass (Patent Document 2), a method of primarily decomposing hemicellulose in a first hydrolysis step and primarily decomposing cellulose in the residue of the first step in a second hydrolysis step (Patent Document 3), and a method of decomposing and extracting hemicellulose by subjecting the biomass to pressurized hot water treatment at 140 to 230° C. and then decomposing and extracting cellulose by subjecting the biomass to pressurized hot water treatment at the temperature not less than the temperature described above (Patent Document 4) have been reported. However, there has yet to be disclosed a technique for controlling the production ratio of the respective components of the monosaccharides, oligosaccharides, and furfurals simultaneously obtained when the biomass is hydrolyzed.

In addition, as a method for manufacturing xylose and xylooligosaccharides from a biomass raw material, a method of treating a water-insoluble residue, which is prepared by removing components extracted from a xylane-containing natural product with hot water at a temperature of at least 110° C. and at most 140° C., with hot water at a temperature of at least the above treatment temperature and at most 200° C. (Patent Document 5) has been reported. However, there has yet to be disclosed a report related to a technique for increasing the productivity of the respective components of the monosaccharides, oligosaccharides, and furfurals simultaneously obtained when the biomass is prehydrolyzed. Moreover, there has also yet to be disclosed a report related to a technique for efficiently separating and recovering the monosaccharides, oligosaccharides, and furfurals simultaneously obtained when the biomass is prehydrolyzed.

Hydrolysis methods are typically classified as a batch method or a continuous method. In a batch method, after a mixture of biomass and an aqueous solution is supplied to a hydrolysis device, the lid of the hydrolysis device is sealed and heated to perform hydrolysis. After hydrolysis, the operation of the device is temporarily suspended, and a solution containing the reaction product is separated and recovered. As a method of producing furfurals with a batch method, a method of adding biomass to a digester, sealing the lid of the digester, performing a hydrolysis reaction by heating the digester for 1 to 2 hours at 160 to 170° C., and recovering the furfurals contained in the gaseous phase has been reported. In this method, it has been reported that the furfural concentration in the aqueous solution recovered from the gaseous phase is approximately 3 to 6 wt. % and that purification can be easily performed by distillation (Non-Patent Document 8). However, in the batch method, after the first run, it is necessary to stop the hydrolysis device and then restart the operation, so it is not possible to process large quantities of biomass, which is problematic in that the production efficiency is poor in comparison to a continuous method.

On the other hand, in a continuous method, a mixture of biomass and an aqueous solution is supplied to a heated hydrolysis device, and the reaction products are continuously recovered. In the continuous method, it is possible to process large quantities of biomass in a short period of time, so there is the merit that the production efficiency of reaction products is high in comparison to the batch method. However, the continuous method has a problem in that the furfural concentration in the gaseous phase becomes low since furfurals are dissolved in the aqueous phase. In order to increase the furfural recovery efficiency, it is necessary to increase the furfural concentration in the gaseous phase as much as possible since furfurals can be recovered from the gaseous phase.

In order to achieve the practical application of furfural production from biomass at an industrial scale, a problem of the continuous hydrolysis method is to reduce the production cost by establishing an efficient furfural recovery method. As a system for producing furfurals from lignocellulose raw materials, a method of performing digestion on wood chips with a continuous digestion device using a lower aliphatic alcohol as a solvent and then recovering by-products such as a furfural from a black liquor produced as a by-product of pulp production has been reported (Patent Document 6). In this system, after the black liquor following digestion is transferred to a flash tank and separated into a gaseous phase (fraction containing ethanol) and a liquid phase (fraction containing furfural), the ethanol used as a drug solution for digestion is recovered from the gaseous phase. On the other hand, the furfural concentration in the liquid phase is from 0.2 to 0.8%, and furfural is concentrated in a subsequent step. In order to efficiently produce furfural, it is preferable to increase the furfural concentration (yield) in the preceding step as much as possible. Presently, there is no report of an economically applicable and efficient furfural separation and recovering method related to furfural production using biomass as a raw material. Accordingly, there is a need for the establishment of a continuous method that increases the furfural concentration in the gaseous phase as much as possible. In addition, there is also a need for the development of a method for efficiently recovering the monosaccharides and oligosaccharides contained in the hydrolysis solution at the same time as furfural production.

PRIOR ART DOCUMENTS

Patent Documents

Patent Document 1: Japanese Unexamined Patent Application Publication No. H-10-327900
Patent Document 2: Japanese Unexamined Patent Application Publication No. 2011-144337A
Patent Document 3: Japanese Unexamined Patent Application Publication No. 2010-253348A
Patent Document 4: Japanese Unexamined Patent Application Publication No. 2002-59118A
Patent Document 5: Japanese Unexamined Patent Application Publication No. 2000-236899A
Patent Document 6: Japanese Unexamined Patent Application Publication (Translation of PCT Application) No. H08-500854

Non-Patent Documents

Non-Patent Document 1: Masashi Mochizuki and Kazufumi Oshima, "Forefront of Bioplastic Materials and Techniques", p.p. 114
Non-Patent Document 2: Hiroaki Okada, "Formulation Design and Drug Discovery in an Innovative Drug Delivery System (DDS)", YAKUGAKU ZASSHI, 131, p.p. 1271 (2011)
Non-Patent Document 3: Top Value Added Chemicals from Biomass Volume I-Results of Screening for Potential Candidates from Sugars and Synthesis Gas, DOE, August 2004
Non-Patent Document 4: Masao Shibata, "Toward the Development of Biomass Utilization Techniques—Treatment Technique Using Pressurized Hot Water—", Abstracts of the 2001 Research Lecture Meeting of the Kyushu Center of the National Institute of Advanced Industrial Science and Technology
Non-Patent Document 5: Tsuyoshi Sakaki, "Separation of Biomass Components by Pressurized Hot Water", Vol. 7, p.p. 245-248, Abstracts of the Lecture Meeting of the Japan Institute of Energy, 1998
Non-Patent Document 6: Hiroki Ando and 5 others, "Decomposition Behavior of Wood Biomass Using Pressurized Hot Water", Research Report of the Kagoshima Prefectural Institute of Industrial Technology, No. 14, p.p., 2000
Non-Patent Document 7: Furfural: Hemicellulose/xylosederived biochemical, Ajit Singh Mamman, Biofuels Bioproducts and Biorefining, Volume 2, Issue 5, p.p. 438-454 (2008)
Non-Patent Document 8: Shinzoho, Distillation, Chemical Industries Co. (Ltd.), p.p. 339-345, 1998

SUMMARY OF THE INVENTION

Problem to be Solved by the Invention

The problem of the present invention is to provide a method for efficiently producing monosaccharides, oligosaccharides, and/or furfurals from biomass and manufacturing monosaccharides, oligosaccharides, and/or furfurals at any ratio.

Means to Resolve the Problems

The present inventors completed the inventions described below as a result of conducting dedicated research to solve the aforementioned problem. The present inventors discovered that the production ratio of monosaccharides, oligosaccharides, and furfurals can be controlled by extracting a primary hydrolysis solution containing monosaccharides, oligosaccharides, and furfurals obtained with a continuous primary hydrolysis device for biomass from an intermediate extraction port provided at any position between the supply port and the discharge port of the continuous primary hydrolysis device.

In addition, the present inventors discovered that the yield of monosaccharides, oligosaccharides, and furfurals can be improved by extracting a hydrolysis solution containing monosaccharides, oligosaccharides, and furfurals from a hydrolysis suspension inside the primary hydrolysis device from intermediate extraction ports formed at a total of two or more positions including the position of the aforementioned intermediate extraction port and a position differing from that of the aforementioned intermediate extraction port, and simultaneously supplying an aqueous liquid into the hydrolysis device from an aqueous liquid supply port formed between each of the intermediate extraction ports.

That is, the present inventors discovered that the yield of monosaccharides, oligosaccharides, and/or furfurals can be improved by extracting a primary hydrolysis solution via a solid-liquid separation device from each of the intermediate extraction ports formed at two or more locations at a distance in the vertical direction at intermediate positions between the supply port and the discharge port of the continuous primary hydrolysis device, and simultaneously supplying an aqueous liquid that can maintain the hydrolysis conditions inside the continuous primary hydrolysis device from the aqueous liquid supply port formed in the continuous primary hydrolysis device at a position between each of the intermediate extraction ports.

In addition, the present inventors discovered that it is possible to obtain a secondary hydrolysis solution with an increased content ratio of at least one type of component selected from a monosaccharide component, an oligosaccharide component, and a furfural component contained in a primary hydrolysis solution by separating and extracting a hydrolysis solution (primary hydrolysis solution) from a (primary) hydrolysis suspension at an intermediate position of the continuous (primary) hydrolysis device, feeding the hydrolysis solution to a secondary hydrolysis device, and performing secondary hydrolysis under pressure at 120 to 230° C. for a retention time of 1 to 180 minutes.

Further, the present inventors discovered that a high-concentration furfural concentrate can be obtained with high yield by providing an intermediate extraction port equipped with a solid-liquid separation device at an intermediate part of a (continuous) primary hydrolysis device and, when performing secondary hydrolysis on the primary hydrolysis solution extracted from the (continuous) primary hydrolysis device as a supply solution for a secondary hydrolysis device, controlling the secondary hydrolysis conditions so that the ratio of the total amount of pentoses in the secondary hydrolysis solution discharged from the discharge port of the secondary hydrolysis device with respect to the total amount of pentoses contained in the solution supplied to the secondary hydrolysis device is within a specified numerical range.

The present inventors discovered that a high-concentration solution of furfurals can be produced efficiently by combining steps of separating and extracting a (primary) hydrolysis solution from a (primary) hydrolysis suspension at an intermediate position of a continuous (primary) hydrolysis device and performing secondary hydrolysis with a secondary hydrolysis device to form a furfural-containing vapor phase and a monosaccharide and oligosaccharide-containing liquid phase.

The present inventors discovered that, in a type of biomass hydrolysis method for supplying an aqueous suspension of biomass from the column top of a continuous hydrolysis device (continuous primary hydrolysis device), performing hydrolysis under pressurization and heating conditions under which monosaccharides, oligosaccharides, and furfurals are produced, and discharging the partially hydrolyzed biomass and a (primary) hydrolysis suspension containing monosaccharides, oligosaccharides, and furfurals as hydrolysates from the bottom of the device, it is not only possible to dramatically improve the yield of monosaccharides, oligosaccharides, and furfurals resulting from the partial hydrolysis of a raw material biomass, but it is also possible to obtain a biomass that can be used as a raw material for producing high-quality pulp with reduced hemicellulose component content as a partially hydrolyzed biomass by extracting and recovering a (primary) hydrolysis solution containing monosaccharides, oligosaccharides, and/or furfurals as hydrolysates from the hydrolysis suspension moving through the hydrolysis device and performing additional hydrolysis on the partially hydrolyzed biomass and the water-soluble hydrolysates discharged from the bottom while effectively utilizing the water-soluble hydrolysates contained in the discharged suspension.

The present inventors discovered that separating and extracting a primary hydrolysis solution from a primary hydrolysis suspension at an intermediate position of a continuous primary hydrolysis device, subjecting the primary hydrolysis solution to flash distillation, and obtaining a furfural-containing aqueous solution from the gaseous phase after flash distillation is an efficient method for manufacturing furfural by hydrolyzing biomass.

That is, the present invention encompasses the following inventions.

[1] A method for manufacturing monosaccharides, oligosaccharides, and furfurals by subjecting a biomass to (primary) hydrolysis under pressurization and heating conditions under which monosaccharides, oligosaccharides, and furfurals are produced while continuously supplying an aqueous suspension of the biomass (raw material suspension) from a supply port of a continuous (primary) hydrolysis device and moving the biomass suspension through the device, continuously discharging the (primary) hydrolysis solution from a discharge port of the continuous (primary) hydrolysis device, and continuously extracting the (primary) hydrolysis solution separated from the (primary) hydrolysis suspension in the device from an intermediate extraction port equipped with a solid-liquid separation device provided at any position between the supply port and the discharge port of the continuous (primary) hydrolysis device in a state in which the temperature and pressurization of (primary) hydrolysis are maintained.

[1-2] A method for continuously manufacturing monosaccharides, oligosaccharides, and furfurals according to [1-1], wherein monosaccharides and oligosaccharides of the hydrolysis solution treated with the continuous hydrolysis device are purified using at least one substance selected from activated carbon, ion exchange resins, and adsorption resins.

[2-1] A method for continuously manufacturing monosaccharides, oligosaccharides, and furfurals from biomass by subjecting a biomass to (primary) hydrolysis while maintaining pressurization and heating conditions under which monosaccharides, oligosaccharides, and furfurals are produced and while continuously supplying an aqueous suspension of the biomass (raw material suspension) from a supply port of a continuous (primary) hydrolysis device and moving the biomass suspension through the device, continuously discharging the (primary) hydrolysis suspension from a discharge port of the (continuous primary) hydrolysis device, extracting a (primary) hydrolysis solution containing monosaccharides, oligosaccharides, and furfurals from the (primary) hydrolysis suspension in the (continuous primary) hydrolysis device from intermediate extraction ports equipped with solid-liquid separation devices formed at two or more positions at a distance in the vertical direction provided at intermediate positions (provided at any intermediate positions) between the raw material suspension supply port and the discharge port of the (continuous primary) hydrolysis device, and simultaneously supplying an aqueous liquid into the (continuous primary) hydrolysis device from an aqueous liquid supply port formed between each of the intermediate extraction ports and maintaining the hydrolysis conditions in the (continuous primary) hydrolysis device.

[2-2] The method for continuously manufacturing monosaccharides, oligosaccharides, and furfurals from biomass according to [2-1], wherein the aqueous liquid supplied from the aqueous liquid supply port formed between each of the intermediate extraction ports is supplied to the (continuous primary) hydrolysis device in a liquid volume equivalent to the liquid volume of the (primary) hydrolysis solution extracted from the intermediate extraction port above the aqueous liquid supply port.

[2-3] The method for continuously manufacturing monosaccharides, oligosaccharides, and furfurals from biomass according to [2-1] or [2-2], wherein the aqueous liquid supplied from the aqueous liquid supply port formed between the intermediate extraction ports is an aqueous liquid in a warm water state.

[2-4] The method for continuously manufacturing monosaccharides, oligosaccharides, and furfurals from biomass according to any one of [2-1] to [2-3], wherein a (primary) hydrolysis suspension extraction conduit provided with a solid-liquid separation device is connected to the discharge port at the bottom of the continuous hydrolysis device (continuous primary hydrolysis device), the (primary) hydrolysis suspension extracted from the bottom discharge port is separated into solid and liquid components, and an additional amount of a hydrolysis solution containing monosaccharides, oligosaccharides, and furfurals is recovered.

[2-5] The method for continuously manufacturing monosaccharides, oligosaccharides, and furfurals from biomass according to any one of [2-1] to [2-4], wherein an additional amount of a hydrolysis solution obtained by separating the (primary) hydrolysis solution extracted from the intermediate extraction port of the continuous hydrolysis device (continuous primary hydrolysis device) and the (primary) hydrolysis suspension extracted from the bottom discharge port into solid and liquid components is fed together to a distillation device, and furfurals contained in the entire hydrolysis solution are separated from the sugar-containing liquid phase as a vapor phase.

[2-6] The method for continuously manufacturing monosaccharides, oligosaccharides, and furfurals from biomass according to one of [2-1] to [2-5], wherein the entire hydrolysis solution extracted from the continuous hydrolysis device (continuous primary hydrolysis device) is pooled, and secondary hydrolysis, in which the content ratio of monosaccharides, oligosaccharides, and furfurals contained in the entire hydrolysis solution is changed, is performed to obtain a hydrolysis solution with an increased content ratio of any product components of monosaccharides, oligosaccharides, or furfurals.

[3-1] A method for continuously manufacturing monosaccharides, oligosaccharides, and furfurals from biomass by subjecting a biomass to primary hydrolysis under pressurization and heating conditions under which monosaccharides, oligosaccharides, and furfurals are produced while continuously supplying an aqueous suspension of the biomass (raw material suspension) from a supply port of a continuous primary hydrolysis device and moving the biomass suspension through the device, continuously discharging the (primary) hydrolysis suspension from a discharge port of the (continuous) primary hydrolysis device, continuously extracting a (primary) hydrolysis solution separated from the (primary) hydrolysis suspension in the (continuous primary hydrolysis) device from an intermediate extraction port equipped with a solid-liquid separation device provided at an intermediate position (provided at any intermediate position) between the supply port and the discharge port of the (continuous) primary hydrolysis device in a state in which the temperature and pressure of (primary) hydrolysis are maintained, feeding the solution to a secondary hydrolysis device, and subjecting the solution to secondary hydrolysis under pressure at 120 to 230° C. for a retention time of 1 to 180 minutes to obtain a secondary hydrolysis solution with an increased content ratio of at least one type selected from the monosaccharide component, the oligosaccharide component, and the furfural component contained in the primary hydrolysis solution.

[3-2] The method for continuously manufacturing monosaccharides, oligosaccharides, and furfurals from biomass according to [3-1], wherein the aqueous suspension of the biomass (raw material suspension) is an aqueous suspension prepared by suspending the biomass in one type selected from ion exchange water and an acid aqueous solution.

[3-3] The method for continuously manufacturing monosaccharides, oligosaccharides, and furfurals from biomass according to [3-1] or [3-2], wherein the secondary hydrolysis in the secondary hydrolysis device is performed under conditions selected from ranges of pressurization from 0.35 to 2.8 MPa, a temperature from 140 to 230° C., and a retention time from 5 to 120 minutes.

[3-4] The method for continuously manufacturing monosaccharides, oligosaccharides, and furfurals from biomass according to any one of [3-1] to [3-3], wherein the secondary hydrolysis in the secondary hydrolysis device is a process for increasing the content ratio of the furfural component in the primary hydrolysis solution.

[3-5] The method for continuously manufacturing monosaccharides, oligosaccharides, and furfurals from biomass according to any one of [3-1] to [3-4], wherein a vapor phase containing produced furfural is separated from the liquid phase by feeding the secondary hydrolysis solution obtained from the secondary hydrolysis device to a concentration/separation device and distilling the solution, a furfural-containing aqueous solution is recovered by condensing the separated vapor phase, and monosaccharides and oligosaccharides are recovered from the liquid phase after distillation.

[3-6] The method for continuously manufacturing monosaccharides, oligosaccharides, and furfurals from biomass according to [3-5], wherein the content ratio of the furfural component is increased by circulating at least part of the liquid phase remaining after the vapor phase is separated by the distillation of the secondary hydrolysis solution in the concentration/separation device to the supply port of the secondary hydrolysis device.

[3-7] The method for continuously manufacturing monosaccharides, oligosaccharides, and furfurals from biomass according to [3-5] or [3-6], wherein at least part of the liquid phase remaining after the vapor phase is separated by the distillation of the secondary hydrolysis solution in the concentration/separation device is added to the aqueous suspension of the biomass supplied to the primary hydrolysis device.

[3-8] The method for continuously manufacturing monosaccharides, oligosaccharides, and furfurals from biomass according to any one of [3-5] to [3-7], wherein the concentration/separation device is at least one type of device selected from a flash distillation device and a vacuum distillation device.

[3-9] The method for continuously manufacturing monosaccharides, oligosaccharides, and furfurals from biomass according to one of [3-1] to [3-8], wherein monosaccharides and oligosaccharides of the secondary hydrolysis solution treated with the secondary hydrolysis device are purified using at least one substance selected from activated carbon, ion exchange resins, and adsorption resins.

[3-10] The method for continuously manufacturing monosaccharides, oligosaccharides, and furfurals from biomass according to [3-5], wherein monosaccharides and oligosaccharides in the liquid phase remaining after the vapor phase is separated by the distillation of the secondary hydrolysis solution in the concentration/separation device are purified using at least one substance selected from activated carbons, ion exchange resins and adsorption resins.

[4-1] A method for manufacturing furfurals from biomass by subjecting a biomass to primary hydrolysis under pressurization and heating conditions under which monosaccharides, oligosaccharides, and furfurals are produced while continuously supplying a biomass raw material suspension from a supply port of a continuous primary hydrolysis device (continuous primary hydrolysis device) and moving the biomass suspension through the device, continuously discharging the (primary) hydrolysis suspension from a discharge port of the continuous (primary) hydrolysis device, extracting a primary hydrolysis solution from the (primary) hydrolysis suspension in the device from an intermediate extraction port equipped with a solid-liquid separation device provided at an intermediate point (provided at any intermediate position) between the supply port and the discharge port of the (continuous) primary hydrolysis device and feeding the solution to a secondary hydrolysis device, and, in the secondary hydrolysis device, performing secondary hydrolysis under conditions under which the ratio (%) of the mass of all pentoses in the secondary hydrolysis solution discharged from the discharge port of the secondary hydrolysis device with respect to the mass of all pentoses contained in the solution supplied to the secondary hydrolysis device containing the primary hydrolysis solution [(mass of all pentoses in the secondary hydrolysis solution discharged from the discharge port of the secondary hydrolysis device/mass of all pentoses contained in the solution supplied to the secondary hydrolysis device)×100] is from 1 to 30%, and separating the secondary hydrolysis solution obtained by the secondary hydrolysis device into a vapor phase containing furfurals and a liquid phase containing sugars or the like.

[4-2] The method for manufacturing furfurals from biomass according to [4-1], wherein the ratio of the mass of all pentoses in the secondary hydrolysis solution discharged from the discharge port of the secondary hydrolysis device with respect to the mass of all pentoses contained in the solution supplied to the secondary hydrolysis device containing the primary hydrolysis solution is in a range from 5 to 20%.

[4-3] The method for manufacturing furfurals from biomass according to [4-1] or [4-2], wherein at least part of the liquid phase containing sugars or the like separated from the secondary hydrolysis solution is added to the biomass raw material suspension supplied to the (continuous) primary hydrolysis device.

[5-1] A method for manufacturing furfurals, monosaccharides, and oligosaccharides from biomass by subjecting a biomass to primary hydrolysis under pressurization and heating conditions under which monosaccharides, oligosaccharides, and furfurals are produced while continuously supplying an aqueous suspension of the biomass (raw material suspension) from a supply port of a continuous primary hydrolysis device (continuous primary hydrolysis device) and moving the biomass suspension through the device, continuously discharging the (primary) hydrolysis suspension from a discharge port of the (continuous) primary hydrolysis device, (continuously) extracting a (primary) hydrolysis solution separated from the (primary) hydrolysis suspension in the device (continuous primary hydrolysis device) from an intermediate extraction port equipped with a solid-liquid separation device provided at an intermediate position (provided at any intermediate position) between the supply port and the discharge port of the (continuous) primary hydrolysis device in a state in which the temperature and pressure of (primary) hydrolysis are maintained, feeding the primary hydrolysis solution to a secondary hydrolysis device, subjecting the solution to secondary hydrolysis, separating and extracting a liquid phase containing monosaccharides and oligosaccharides and a vapor phase containing furfurals from the secondary hydrolysate in the secondary hydrolysis device, further feeding the vapor phase to a distillation device, treating the vapor phase, and recovering the solution as a concentrate containing furfurals.

[5-2] The method for manufacturing furfurals, monosaccharides, and oligosaccharides from biomass according to [5-1], wherein at least part of the liquid phase containing monosaccharides and oligosaccharides extracted from the secondary hydrolysis device is circulated to the secondary hydrolysis device and subjected to hydrolysis together with the primary hydrolysis solution.

[5-3] A method for manufacturing furfurals, monosaccharides, and oligosaccharides from biomass by subjecting a biomass to primary hydrolysis under pressurization and heating conditions under which monosaccharides, oligosaccharides, and furfurals are produced while continuously supplying an aqueous suspension of the biomass from a supply port of a continuous primary hydrolysis device and moving the biomass suspension through the device, continuously discharging the hydrolysis suspension from a discharge port of the primary hydrolysis device, extracting a primary hydrolysis solution separated from the hydrolysis suspension in the device from an intermediate extraction port equipped with a solid-liquid separation device provided at an intermediate position between the supply port and the discharge port of the primary hydrolysis device, feeding the primary hydrolysis solution to a secondary hydrolysis device, subjecting the solution to secondary hydrolysis to produce a secondary hydrolysate, separating and extracting a vapor phase containing furfurals from the secondary hydrolysate in the secondary hydrolysis device, distilling the vapor phase, recovering a solution as a concentrate containing furfurals, and extracting a sugar-containing liquid containing monosaccharides and oligosaccharides as a liquid phase after the vapor phase containing furfurals is separated.

[5-4] The method for manufacturing furfurals, monosaccharides, and oligosaccharides from biomass according to [5-3], wherein at least part of the sugar-containing liquid containing monosaccharides and oligosaccharides extracted from the secondary hydrolysate is circulated to the secondary hydrolysis device and subjected to hydrolysis together with the primary hydrolysis solution.

[5-5] The method for manufacturing furfurals, monosaccharides, and oligosaccharides from biomass according to [5-3] or [5-4], wherein the extraction of a vapor phase containing furfurals from the secondary hydrolysate is performed with a method selected from a method of continuously extracting a vapor phase containing furfurals generated during secondary hydrolysis in the secondary hydrolysis device from the secondary hydrolysis device and a method of extracting a vapor phase containing furfurals generated from the secondary hydrolysate after the completion of secondary hydrolysis from the secondary hydrolysis device.

[5-6] The method for manufacturing furfurals, monosaccharides, and oligosaccharides from biomass according to any one of [5-3] to [5-5], wherein before a liquid phase prepared by separating a vapor phase containing furfurals from the secondary hydrolysate is extracted from the secondary hydrolysis device, the liquid phase is subjected to a process for additionally recovering the furfurals remaining in the liquid phase and improving the sugar concentration in the liquid phase by means of at least one type of process selected from a process of generating a vapor containing furfurals from the liquid phase by reducing the pressure in the secondary hydrolysis device, and a process of generating a vapor containing furfurals from the liquid phase by blowing an inert gas or water vapor into the liquid phase in the secondary hydrolysis device.

[5-7] The method for manufacturing furfurals, monosaccharides, and oligosaccharides from biomass according to any one of [5-3] to [5-6], wherein furfurals newly produced in a sugar-containing liquid containing monosaccharides and oligosaccharides consisting of the liquid phase extracted from the secondary hydrolysis device are separated and recovered from the sugar-containing liquid after being extracted from the secondary hydrolysis device, and the liquid is subjected to distillation to improve the sugar concentration in the sugar-containing liquid.

[6-1] A method for continuously manufacturing monosaccharides, oligosaccharides, and furfurals from biomass by continuously supplying a raw material suspension consisting of an aqueous suspension of a biomass from the top of a (continuous primary) hydrolysis device under hydrolysis conditions under which monosaccharides, oligosaccharides, and furfurals are produced from the biomass, extracting a (primary) hydrolysis solution containing the hydrolysate from an intermediate extraction port of the (continuous primary) hydrolysis device (extraction port equipped with a solid-liquid separation device provided at any position between the supply port and the discharge port of the device) while extracting a discharge suspension (primary hydrolysis suspension) containing the hydrolyzed biomass and the hydrolysate from the bottom, transferring the discharge suspension (primary hydrolysis suspension) to a separation device for recovering the hydrolyzed biomass with a discharge suspension transfer conduit, separating the suspension into the hydrolyzed biomass and a hydrolysis solution containing the hydrolysate, recovering the hydrolyzed biomass, extracting the hydrolysis solution from the separation device to a circulation conduit for circulating and combining the hydrolysis solution with the discharge suspension discharged from the bottom of the hydrolysis device, and circulating and combining the remaining part with the discharge suspension discharged from the bottom of the hydrolysis device while recovering part of the suspension as a hydrolysate from an intermediate part of the circulation conduit.

[6-2] The method for continuously manufacturing monosaccharides, oligosaccharides, and furfurals from biomass according to [6-1], wherein a solution is separated from the discharge suspension by a separation device and extracted to a circulation conduit for the hydrolysis solution, and an aqueous liquid is added to the hydrolysis solution of the remaining part recovered as part of the hydrolysis solution containing the hydrolysate in the circulation conduit.

[6-3] The method for continuously manufacturing monosaccharides, oligosaccharides, and furfurals from biomass according to [6-1] or [6-2], wherein an aqueous liquid is supplied to the hydrolysis suspension in the hydrolysis device from an aqueous liquid supply port positioned below an intermediate extraction port provided at an intermediate position of the hydrolysis device.

[6-4] The method for continuously manufacturing monosaccharides, oligosaccharides, and furfurals from biomass according to any one of [6-1] to [6-3], wherein the aqueous liquid supplied from the aqueous liquid supply port of the hydrolysis device and/or the aqueous liquid supplied to the hydrolysis solution extracted to the circulation conduit for the hydrolysis solution from the separation device in the discharge suspension transfer conduit and circulated and combined with the discharge suspension from the bottom of the reaction device are warm aqueous liquids.

[6-5] The method for continuously manufacturing monosaccharides, oligosaccharides, and furfurals from biomass according to any one of [6-1] to [6-4], wherein a second intermediate extraction port is formed at a position even farther below aqueous liquid supply port below the intermediate extraction port of the hydrolysis device, and a hydrolysis solution containing monosaccharides, oligosaccharides, and furfurals is recovered from the hydrolysis suspension moving through the hydrolysis device.

[6-6] The method for continuously manufacturing monosaccharides, oligosaccharides, and furfurals from biomass according to any one of [6-1] to [6-5], wherein a washing solution making contact in a countercurrent manner with the hydrolysis suspension moving through the hydrolysis device moving in the bottom direction is supplied to the bottom of the hydrolysis device.

[6-7] The method for continuously manufacturing monosaccharides, oligosaccharides, and furfurals from biomass according to any one of [6-1] to [6-6], wherein a hydrolysis solution extracted from the intermediate extraction port of the hydrolysis device and a hydrolysis solution separated from the discharge suspension by the separation device and extracted to a transfer conduit for a hydrolysis solution are supplied to a distillation/separation device and separated into a fraction containing furfurals and a fraction containing sugars.

[6-8] The method for continuously manufacturing monosaccharides, oligosaccharides, and furfurals from biomass according to [6-7], wherein the distillation/separation device is a flash distillation device which extracts a vapor fraction containing furfurals from the column top and extracts a hydrolysate-containing liquid fraction containing sugars from the column bottom.

[6-9] The method for continuously manufacturing monosaccharides, oligosaccharides, and furfurals from biomass according to any one of [6-1] to [6-8], wherein the entire hydrolysis solution recovered from the hydrolysis suspension is pooled, and secondary hydrolysis, in which the content ratio of monosaccharides, oligosaccharides, and furfurals contained in the entire hydrolysis solution is changed, is performed to obtain a hydrolysis solution with an increased content ratio of any components of monosaccharides, oligosaccharides, or furfurals.

[7-1] A method for continuously manufacturing furfural from biomass by subjecting a biomass to (primary) hydrolysis under pressurization and heating conditions under which furfurals are produced while continuously supplying an aqueous suspension of the biomass (raw material suspension) from a supply port of a continuous primary hydrolysis device (continuous primary hydrolysis device) and moving the biomass suspension through the device, continuously discharging the (primary) hydrolysis suspension from a discharge port of the (continuous primary) hydrolysis device, continuously extracting a (primary) hydrolysis solution separated from the (primary) hydrolysis suspension in the device (continuous primary hydrolysis device) from an intermediate extraction port equipped with a solid-liquid separation device provided at an intermediate position (provided at any intermediate position) between the supply port and the discharge port of the (continuous primary) hydrolysis device in a state in which the temperature and pressure of (primary) hydrolysis are maintained, feeding the solution to a concentration/separation device, subjecting the solution to flash distillation to separate a vapor phase containing the produced furfural from the liquid phase, and obtaining a furfural-containing aqueous solution by condensing the separated vapor phase.

[7-2] The method for continuously manufacturing furfural from biomass according to [7-1], wherein at least part of the liquid phase remaining after the vapor phase is separated by flash distillation in the concentration/separation device is added to the aqueous suspension of the biomass.

[7-3] The method for continuously manufacturing furfural from biomass according to [7-1] or [7-2], wherein the aqueous suspension of the biomass is an aqueous suspension prepared by suspending the biomass in at least one type selected from ion exchange water and an acid aqueous solution.

[8] Any of the aforementioned methods, wherein an aqueous washing solution is supplied to the (continuous primary) hydrolysis device from the vicinity of the discharge port of the (primary) continuous hydrolysis device and is brought into contact with the (primary) hydrolysis suspension in a countercurrent manner between the intermediate extraction port equipped with a solid-liquid separation device and the discharge port.

[9] Any of the aforementioned methods, wherein the biomass is a wood biomass.

Effects of the Invention

With the present invention, it becomes possible to efficiently manufacture monosaccharides, oligosaccharides, and/or furfurals. In addition, since monosaccharides, oligosaccharides, and/or furfurals can be manufactured at any ratio in accordance with the intended purpose, a method for manufacturing monosaccharides, oligosaccharides, and/or furfurals with high production efficiency is provided.

This specification includes the content described in the specification, the scope of the patent claims, and the drawings of Japanese Patent Application No. 2011-261364, Japanese Patent Application No. 2012-156062, Japanese Patent Application No. 2011-288978, Japanese Patent Application No. 2012-050849, Japanese Patent Application No. 2012-078499, Japanese Patent Application No. 2012-093459, Japanese Patent Application No. 2012-165359, Japanese Patent Application No. 2012-162834, and Japanese Patent Application No. 2012-226726 serving as the basis for the priority rights of this application.

DETAILED DESCRIPTION OF THE INVENTION

The method for manufacturing monosaccharides, oligosaccharides, and/or furfurals of the present invention will be described in further detail hereinafter.

(Biomass Raw Material)

The biomass used in the present invention may be a material containing pentoses as constituent sugars, and examples of wood-based raw materials include chips or bark of trees, forest brushwood, timber from forest thinning, waste wood, or the like, buds sprouting from woody plants, sawdust generated from lumber factories, pruning branches and leaves of street trees, and construction waste wood. Hardwood and softwood can be used as wood-based raw materials. Examples of herb-based raw materials include agricultural waste such as kenaf, rice straw, wheat straw, corn cobs, and bagasse, residues and waste of industrial crops such as oil crops and rubber (for example, EFB: Empty Fruit Branch), and lignocellulosic biomass such as *Erianthus, Miscanthus*, or napier grass serving as herb-based energy crops.

In addition, the biomass can utilize paper derived from wood, waste paper, pulp, pulp sludge, sludge, sewage, food waste, and the like as raw materials. These biomasses can be used alone or as a combination of multiple biomasses. Further, the biomass can be used regardless of whether it is a dry solid, a solid containing water, or a slurry. If the biomass is a dry solid or a solid containing water, it is preferable to supply the biomass to a hydrolysis reaction device after mixing the biomass with water to form a slurry state.

(Continuous Primary Hydrolysis Device)

The continuous primary hydrolysis device used in the method of the present invention is a pressurization/heating hydrolysis device—in particular, a continuous pressurization/heating hydrolysis device having an intermediate extraction port equipped with a solid-liquid separation device—which is cable of continuously hydrolyzing biomass under pressurization/heating conditions and continuously separating and extracting a hydrolysis solution consisting of an aqueous solution containing hydrolysates in a state in which the hydrolysis temperature and pressure are maintained from a hydrolysis suspension consisting of an aqueous solution containing the hydrolyzed biomass and hydrolysates such as monosaccharides, oligosaccharides, furfurals, and other organic acids.

Figure 1:
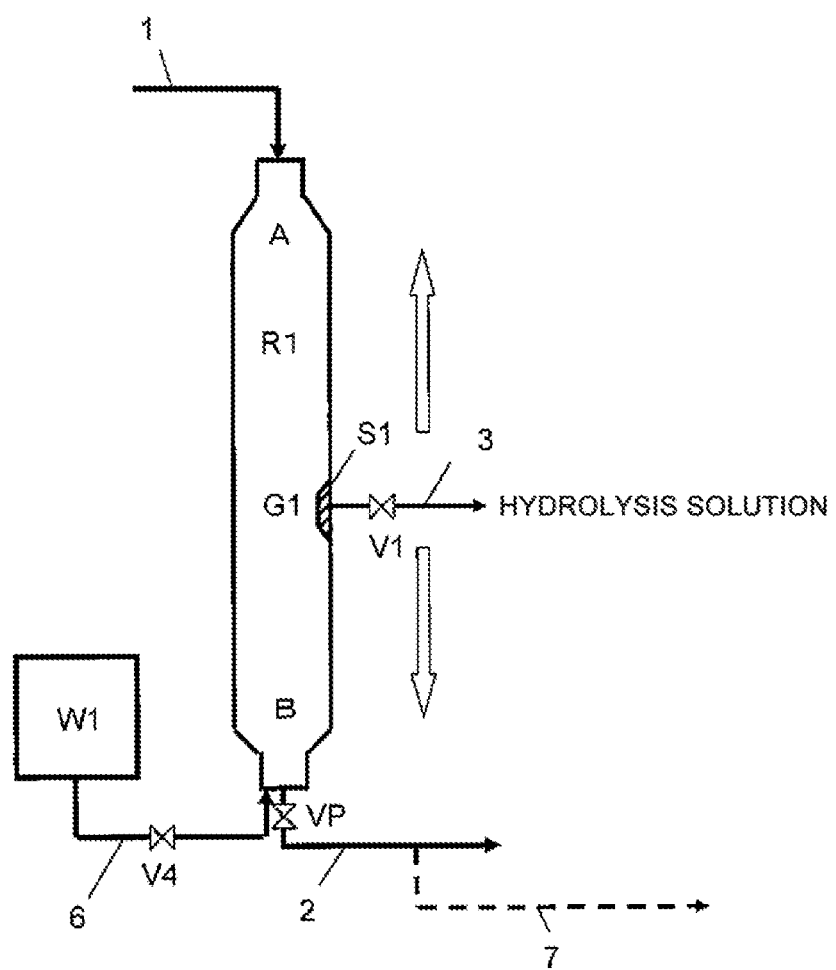
FIG. 1 illustrates the method for manufacturing monosaccharides, oligosaccharides, and/or furfurals with a continuous primary hydrolysis device according to the present invention.

As illustrated in FIG. 1, an example of the continuous primary hydrolysis device described above is a column-type continuous primary hydrolysis device R1 having a supply port A to which a supply conduit 1 for a raw material suspension consisting of the biomass and water (aqueous suspension raw material supply line 1) is connected, a discharge port B to which a hydrolysis suspension discharge conduit 2 containing the hydrolyzed biomass is connected, and an intermediate extraction port G1 equipped with a solid-liquid separation device S1 which is provided at an intermediate point between the supply port A for the raw material suspension and the discharge port B for the hydrolysis suspension so as to enable the continuous separation and extraction of a hydrolysis solution portion consisting of an aqueous solution containing a water-soluble hydrolysate from the hydrolysis suspension resulting from the hydrolysis of the biomass in the suspension under pressure and temperature conditions under which monosaccharides, oligosaccharides, and/or furfurals are formed. In the present invention, conduits and lines are synonymous.

In the device illustrated in FIG. 1, the raw material biomass is continuously supplied to the continuous primary hydrolysis device R1 from the supply port A to which the raw material suspension supply conduit 1 is connected in the state of an aqueous suspension and is moved through the device while being subjected to hydrolysis under pressurization/heating conditions. The solution is continuously discharged as a hydrolysis suspension containing the hydrolyzed biomass from the discharge port B to which the other hydrolysis suspension discharge conduit 2 is connected. A portion of the hydrolysis solution containing water-soluble hydrolysates is separated from the hydrolysis suspension moving through the device by the solid-liquid separation device S1 installed at an intermediate point of the device between the supply port A and the discharge port B. The solution is continuously extracted to a hydrolysis solution extraction conduit 3 (transfer line 3) from the intermediate point of the device while the pressure and temperature of hydrolysis are maintained, and in some cases the solution may be fed to a concentration/separation device F.

The intermediate extraction port G1 of the continuous primary hydrolysis device R1 can be provided at any position as long as the port is between the supply port A to which the raw material suspension supply conduit 1 is connected and the discharge port B to which the hydrolysis suspension discharge conduit 2 containing the hydrolyzed biomass is connected. By extracting the hydrolysis solution from the intermediate extraction port G1 provided at any position, it is possible to control the production ratio of monosaccharides, oligosaccharides, and/or furfurals and also to control the production volume of each component.

As illustrated in FIG. 1, it is possible to supply a washing solution to the bottom of the continuous primary hydrolysis device R1 from a washing solution supply device W1 via a washing solution supply conduit 6 and to bring the washing solution into contact with the hydrolysis suspension moving from the intermediate extraction port G1 of the continuous primary hydrolysis device R1 to the bottom discharge port B in a countercurrent manner. The washing solution from the washing solution supply conduit 6 may be supplied continuously or intermittently. It is preferable to use an aqueous solution containing water or an acid as the washing solution from the washing solution supply conduit 6, but any solution can be used without any particular limitation as long as the solution is an aqueous solution that does not have an adverse effect on the hydrolysis solution extracted from the intermediate extraction port G1 to the conduit 3. The washing solution supplied to the bottom moves from the lower part (bottom) to the upper part in the opposite direction as the movement direction of the hydrolysates or the hydrolysis suspension and is extracted to the conduit 3 in a mixed state with the hydrolysis solution from the extraction port G1 equipped with the solid-liquid separation device S1 at an intermediate point of the device.

By employing the countercurrent washing operation described above, it is possible to move the hydrolysates (monosaccharides, oligosaccharides, and furfurals) in the hydrolysis suspension, which is an aqueous suspension containing the hydrolyzed biomass moving from the upper part to the lower part and from which a portion of the hydrolysis solution is removed by the solid-liquid separation device S1, into the washing solution and to recover the solution as the hydrolysis solution extracted to the conduit 3. Accordingly, there is the merit that the loss of hydrolysates discharged from the conduit 2 together with the hydrolysis suspension at the bottom of the continuous primary hydrolysis device R1 in association with the hydrolyzed biomass is suppressed.

Figure 3:
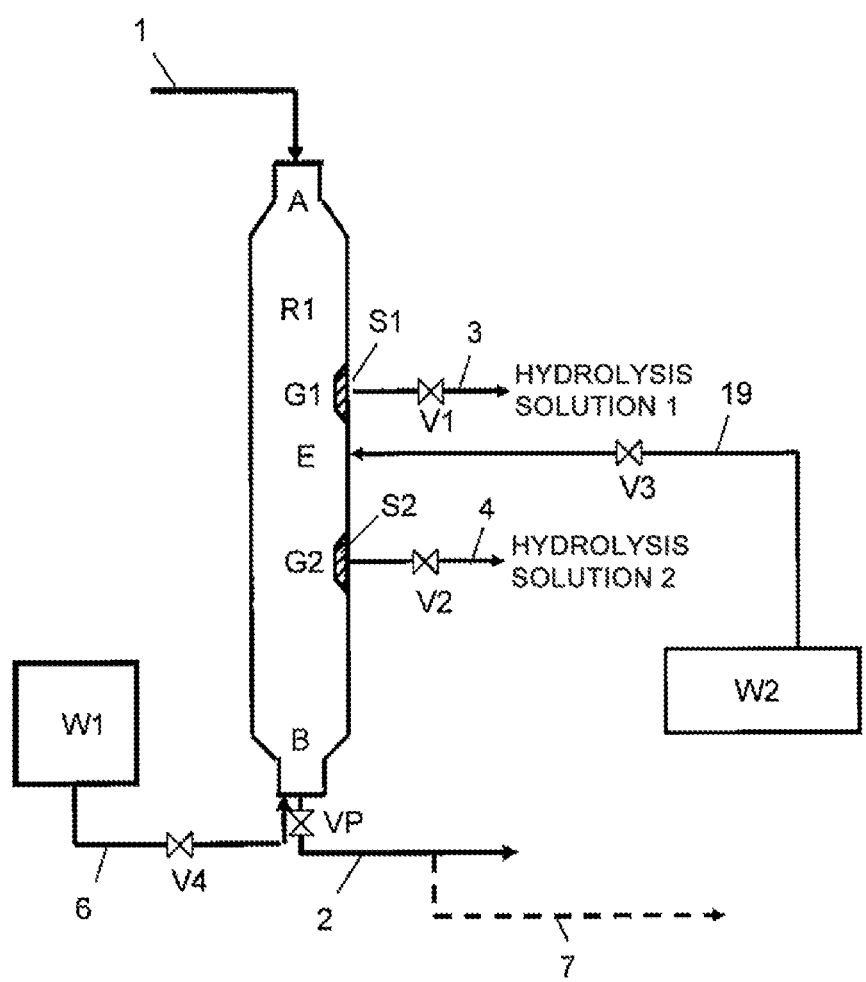
FIG. 3 illustrates a device for implementing the method for continuously manufacturing monosaccharides, oligosaccharides, and/or furfurals from biomass according to the present invention.

In addition, as illustrated in FIG. 3, an example of the continuous primary hydrolysis device R1 is a column-type continuous primary hydrolysis device R1 having a top supply port A to which a raw material suspension supply conduit 1 for supplying a raw material suspension consisting of the biomass and an aqueous liquid is connected, a bottom discharge port B to which a discharge conduit 2 for discharging the hydrolysis suspension containing the hydrolyzed biomass, an intermediate extraction port G1 equipped with a solid-liquid separation device S1 and an intermediate extraction port G2 equipped with a solid-liquid separation device S2, the extraction ports G1 and G2 being provided at an intermediate point between the supply port A and the discharge port B and being respectively connected to a conduit 3 (extraction conduit 3) for a hydrolysis solution 1 and a conduit 4 (extraction conduit 4) for a hydrolysis solution 2 capable of separating only a hydrolysis solution containing water-soluble hydrolysates from the hydrolysis suspension containing the raw material biomass, monosaccharides, oligosaccharides, and furfurals and separating the solution to the outside of the device, an aqueous liquid supply port E for supplying an aqueous liquid to the continuous primary hydrolysis device R1 from the aqueous liquid supply device W2 via an aqueous liquid supply conduit 19 at a point between the intermediate extraction ports G1 and G2, and a washing solution supply device W1 for supplying a countercurrent washing solution to the bottom of the continuous primary hydrolysis device R1 via a washing solution supply conduit 6.

In FIG. 3, the intermediate extraction ports G1 and G2 are installed at two locations distanced from one another vertically on the side surface of the cylindrical part of the continuous primary hydrolysis device R1, but the intermediate extraction ports are not limited to two locations and may be installed at three or more positions. For example, when a third intermediate extraction port (GX) is further installed, it is preferable to provide an aqueous liquid supply port E between the intermediate extraction port G2 and the third intermediate extraction port (GX) as well so that an aqueous liquid can be supplied to the continuous primary hydrolysis device R1 as needed.

Figure 4:
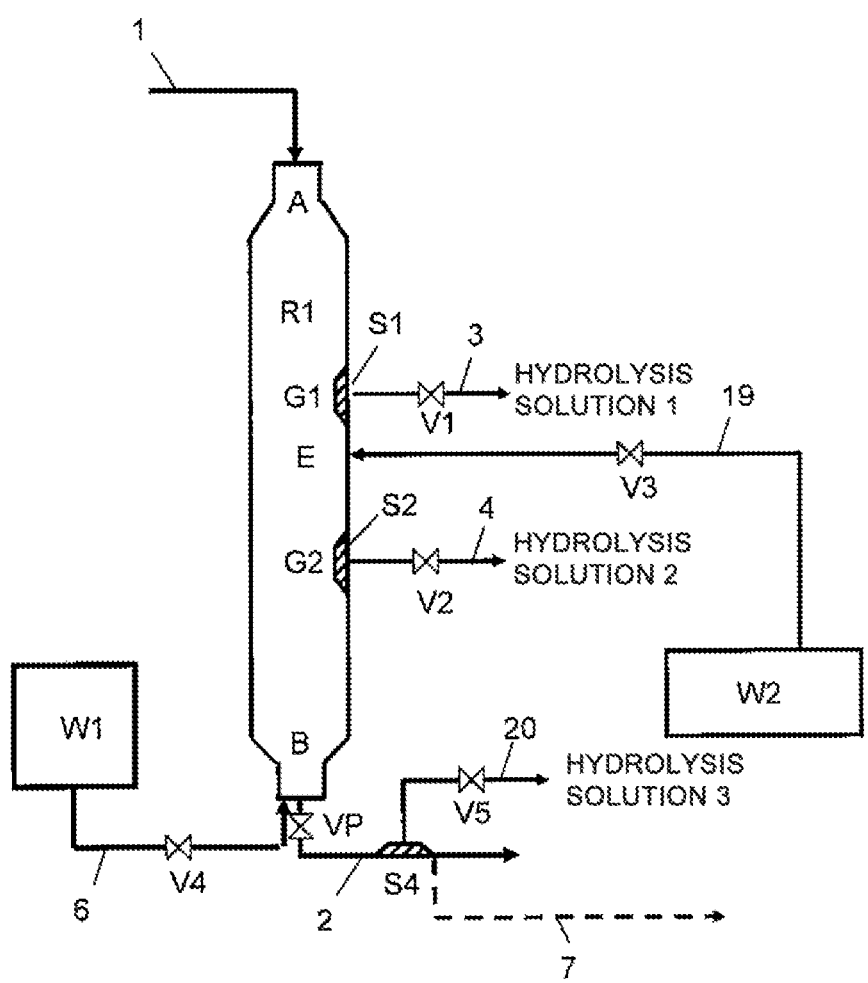
FIG. 4 illustrates a device for implementing the method for continuously manufacturing monosaccharides, oligosaccharides, and/or furfurals from biomass according to the present invention.

In FIG. 3, it is also possible to establish a method for continuously manufacturing monosaccharides, oligosaccharides, and furfurals for the purpose of manufacturing a cellulose component in which the hemicellulose component fed to various manufacturing processes using a cellulose component such as a manufacturing process for pulp, for example, is reduced by connecting a hydrolysis suspension transfer conduit 7 (solid content transfer conduit 7), which is capable of transferring the hydrolysis suspension from the discharge port B in the present state or in a solid state primarily consisting of a cellulose component by dehydrating and condensing the suspension, to the discharge conduit 2 for extracting the hydrolysis suspension from the discharge port B at the bottom of the continuous primary hydrolysis device R1. In order to establish such a method for continuously manufacturing monosaccharides, oligosaccharides, and furfurals for the purpose of manufacturing a cellulose component, as illustrated in FIG. 4, it is possible to use a device in which an extraction port provided with a solid-liquid separation device S4 is disposed on the discharge conduit 2, and the extraction conduit 20 for the hydrolysis solution 3 and the hydrolysis suspension transfer conduit 7 primarily for cellulose consisting of the hydrolyzed biomass are branched from the discharge conduit 2.

In the case of the continuous primary hydrolysis device R1 illustrated in FIG. 3, in which the intermediate extraction ports G1 and G2 are provided at two locations distanced from one another in the vertical direction, a raw material suspension containing 0.5 to 10 parts by mass and preferably 2 to 8 parts by mass of an aqueous liquid per 1 part by mass of the biomass (dry) is typically supplied to the continuous primary hydrolysis device R1 from the supply port A by the raw material suspension supply conduit 1. Among the intermediate extraction ports G1 and G2 provided at two locations, the liquid volume of the hydrolysis solution 1 extracted to the extraction conduit 3 from the first intermediate extraction port G1 is set to a range of 0.5 to 10 parts by mass and preferably 2 to 6 parts by mass per 1 part by mass of the biomass (dry) in the hydrolysis suspension.

The liquid volume of the hydrolysis solution 2 extracted to the extraction conduit 4 from the second intermediate extraction port G2 is not particularly limited and is set appropriately in accordance with the supply volume or the like of the countercurrent washing solution supplied to the bottom of the continuous primary hydrolysis device R1 from the washing solution supply device W1 via the supply conduit 6.

At the same time that the extraction of the hydrolysis solutions from the intermediate extraction ports G1 and G2 begins as described above, an aqueous liquid of roughly the same composition as that of the aqueous liquid used in the raw material suspension is supplied to the aqueous liquid supply port E installed at a position between the intermediate extraction ports G1 and G2 of the continuous primary hydrolysis device R1 from an aqueous liquid supply device W2 via the supply conduit 19. As a result, the concentration of the suspension in the continuous primary hydrolysis device R1 is adjusted and the hydrolysis of the biomass progresses. Accordingly, the aqueous liquid supply port E must be installed between the upper first intermediate extraction port G2 and the lower second intermediate extraction port G2.

When the third intermediate extraction port (GX) is installed at a position below the second intermediate extraction port G2, it is preferable to also install an aqueous liquid supply port E between the second intermediate extraction port G2 and the third intermediate extraction port (GX) so as to ensure that the state of the hydrolysis suspension in the hydrolysis device can be appropriately adjusted to a state in which the desired hydrolysis progresses favorably.

The aqueous liquid supplied from the aqueous liquid supply device W2 via the conduit 19 is not particularly limited in terms of the composition or the like thereof as long as the solution is an aqueous liquid capable of maintaining the hydrolysis conditions such as the concentration, temperature, and pressure of the hydrolysis suspension to the proper ranges after only the hydrolysis solution is extracted from the intermediate extraction port G1. In addition, the supply method that is employed may be, for example, a method of transferring and supplying an aqueous liquid in a warm water state from the aqueous liquid supply device W2 illustrated in FIG. 3 to the continuous primary hydrolysis device R1 with a pump.

The extraction of the hydrolysis solution from the continuous primary hydrolysis device R1 and the supply of the aqueous liquid to the continuous primary hydrolysis device R1 are preferably performed so that the extraction of the hydrolysis solution from the intermediate extraction port and the supply of the aqueous liquid to the aqueous liquid supply port E occur simultaneously and at roughly the same liquid volumes, and these processes may be continuous or intermittent.

The temperature of the aqueous liquid supplied to the continuous primary hydrolysis device R1 is preferably from 90 to 200° C. and more preferably from 150 to 180° C.

In the process described above, by extracting a hydrolysis solution from intermediate extraction ports at two or more locations of the continuous primary hydrolysis device R1 and simultaneously supplying an aqueous liquid to the continuous primary hydrolysis device R1 at a volume equivalent to the liquid volume of the extracted hydrolysis solution, the total amount of monosaccharides, oligosaccharides, and furfurals eluted from the biomass raw material being treated in the continuous primary hydrolysis device R1 increases, which makes it possible to manufacture monosaccharides, oligosaccharides, and furfurals with a higher yield than when a hydrolysis solution is extracted from only the intermediate extraction port G1 at one location of the continuous primary hydrolysis device R1.

As illustrated in FIG. 3, it is possible to supply a washing solution to the bottom of the continuous primary hydrolysis device R1 from the washing solution supply device 1 via the washing solution supply conduit 6 and to bring the washing solution into contact with the hydrolysis suspension moving toward the discharge port B from the position of the second intermediate extraction port G2 on the lower side of the continuous primary hydrolysis device R1 in a countercurrent manner. When the countercurrent washing solution is supplied from the washing solution supply conduit 6 in this way, it is not essential for the aqueous liquid supply port (E) for adjusting the concentration, temperature, pressure, or the like of the hydrolysis suspension at a position farther below the second intermediate extraction port G2 on the lower side to be installed at a position below the second intermediate extraction port G2. However, the aqueous liquid supply port (E) can also be installed below the second intermediate extraction port G2 so as to enable an appropriate response in the event that the state of the biomass in the hydrolysis suspension in the region below the second intermediate extraction port becomes such that it is necessary to further maintain the hydrolysis conditions.

The washing solution from the washing solution supply conduit 6 illustrated in FIGS. 3 and 4 may be supplied continuously or intermittently. It is preferable to use an aqueous solution containing water or an acid as the washing solution from the washing solution supply conduit 6, but any solution can be used without any particular limitation as long as the solution is an aqueous liquid that does not have an adverse effect on the hydrolysis solutions extracted from intermediate extraction ports at two or more locations. In addition, the countercurrent washing solution may also be supplied in a warm water state. The countercurrent washing solution supplied from the bottom of the continuous primary hydrolysis device R1 moves upward from the bottom in the opposite direction as the movement direction of the hydrolysis suspension and is extracted to the conduit 4 in a mixed state primarily with the hydrolysis solution from the second intermediate extraction port G2 equipped with a solid-liquid separation device at an intermediate position.

By employing the countercurrent washing operation described above, it is possible to move water-soluble hydrolysates (monosaccharides, oligosaccharides, furfurals, and the like) in the hydrolysis suspension into the washing solution while the hydrolysis suspension containing the hydrolyzed biomass and the hydrolysis solution moving to the discharge port B from the supply port A of the continuous primary hydrolysis device R1 moves further in the direction of the discharge port B in a state in which a portion of the hydrolysis solution is removed by the intermediate extraction ports G1 and G2 equipped with solid-liquid separation devices, and to recover the solution as the hydrolysis solution 2 extracted to the conduit 4 from the intermediate extraction port G2 on the lower side. Accordingly, the amounts of hydrolysates such as furfurals in the hydrolysis suspension discharged to the discharge conduit 2 from the discharge port B at the bottom of the continuous primary hydrolysis device R1 in association with the hydrolyzed biomass can be kept to very low levels.

In another embodiment, the continuous primary hydrolysis device is a continuous pressurization/heating hydrolysis device which is capable of continuously hydrolyzing biomass in a raw material suspension while maintaining the raw material suspension supplied from the top supply port at the pressurization/heating conditions and moving the suspension through the hydrolysis device and is capable of separating a hydrolysis solution consisting of an aqueous solution containing hydrolysates from a hydrolysis suspension consisting of an aqueous solution containing the partially hydrolyzed biomass and hydrolysates such as monosaccharides, oligosaccharides, furfurals, and other organic acids and extracting the hydrolysis solution from an intermediate point of the hydrolysis device.

Figure 19:
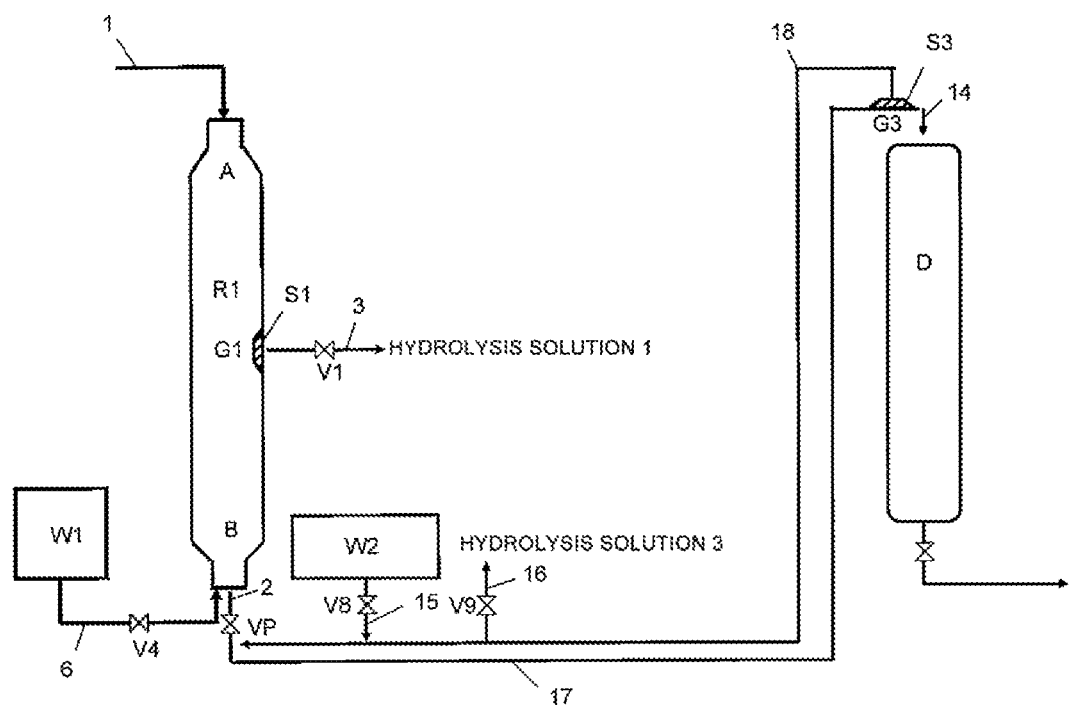
FIG. 19 illustrates a device for implementing the method for continuously manufacturing monosaccharides, oligosaccharides, and/or furfurals from biomass according to the present invention.

As illustrated in FIG. 19, an example of the continuous primary hydrolysis device R1 is a column-type hydrolysis device having a top part A to which a supply conduit 1 for supplying a raw material suspension consisting of the biomass and an aqueous liquid is connected, a bottom part B to which a discharge conduit 2 for a discharge suspension consisting of a hydrolysis suspension containing the hydrolyzed biomass is connected, an intermediate extraction port G1 equipped with a solid-liquid separation device, the extraction port G1 being provided at an intermediate point between the top part A and the bottom part B and being connected to an extraction conduit 3 for a hydrolysis solution (hydrolysis solution 1) capable of separating part of a hydrolysis solution containing aqueous hydrolysates from a hydrolysis suspension containing the partially hydrolyzed biomass and monosaccharides, oligosaccharides, furfurals, and the like, which are hydrolysates, and extracting the solution to the outside of the device. Further, a washing solution supply conduit 6 for supplying a countercurrent washing solution from a washing solution supply device W1 to the bottom part B of the continuous primary hydrolysis device R1 is connected via a valve V4.

In the continuous primary hydrolysis device R1 illustrated in FIGS. 16 and 19, an aqueous liquid supply port E for supplying an aqueous liquid from the aqueous liquid supply device W2 via the aqueous liquid supply conduit 19 having a valve V3 can be provided at a position below the intermediate extraction port G1 in order to resupply an aqueous liquid of the same type as the aqueous liquid used in the raw material suspension to the hydrolysis suspension after part of the hydrolysis solution (hydrolysis solution 1) is extracted from the intermediate extraction port G1.

Figure 16:
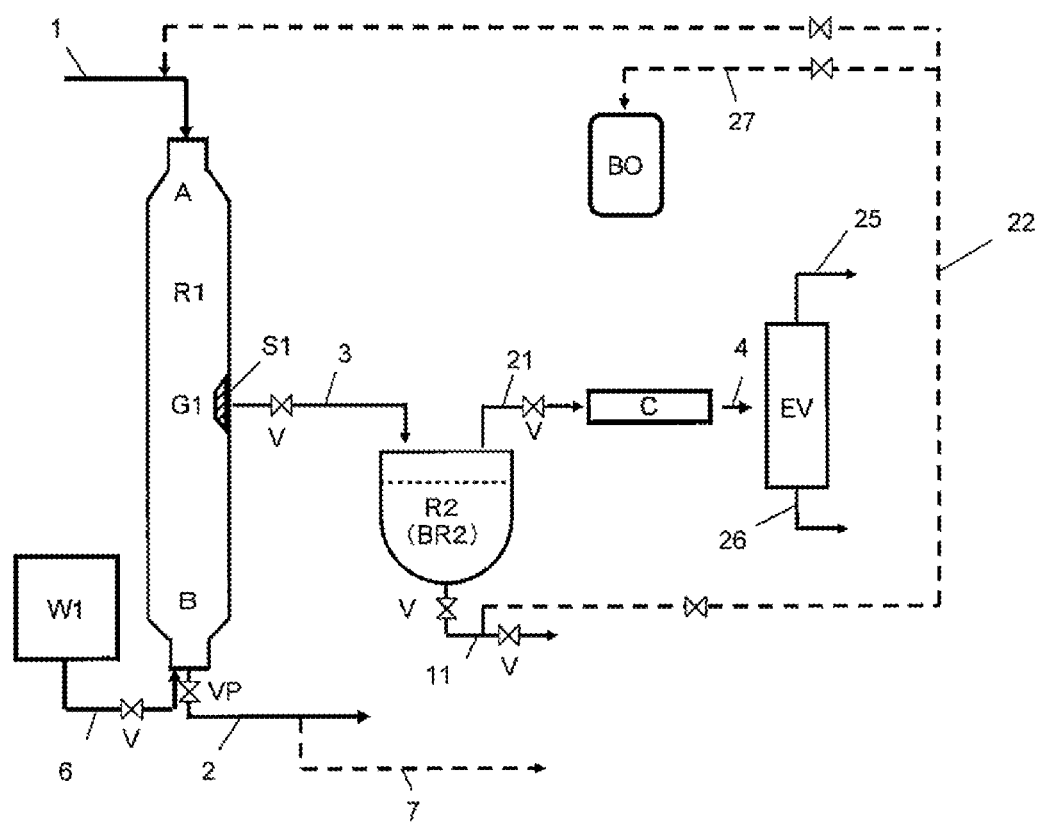
FIG. 16 illustrates an example of a device for implementing the method for manufacturing monosaccharides, oligosaccharides, and/or furfurals from biomass according to the present invention.
Figure 21:
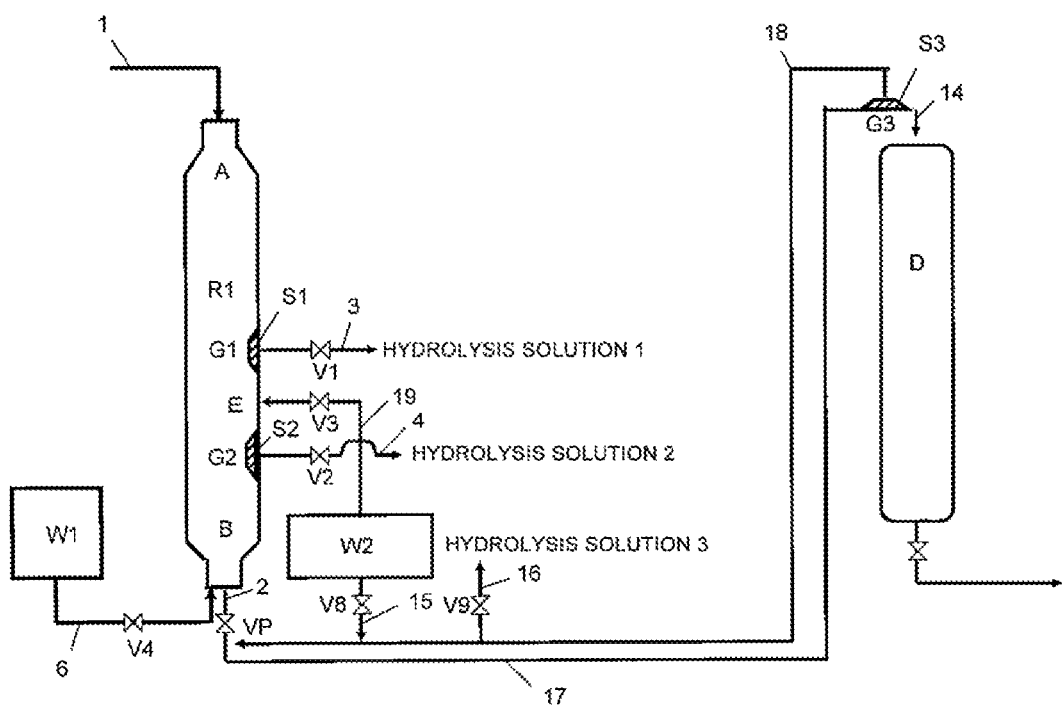
FIG. 21 illustrates a device for implementing the method for continuously manufacturing monosaccharides, oligosaccharides, and/or furfurals from biomass according to the present invention.

In the continuous primary hydrolysis device R1 illustrated in FIGS. 16 and 19, the intermediate extraction port G1 is provided at only one location on the side surface of the cylindrical part of the continuous primary hydrolysis device R1, but this intermediate extraction port is not limited to one location and may be provided at two or more positions. For example, as illustrated in FIG. 21, the hydrolysis device may be such that an intermediate extraction port G2 equipped with a solid-liquid separation device to which an extraction conduit 4 for a hydrolysis solution (hydrolysis solution 2) capable of separating only the hydrolysis solution portion and extracting the solution to the outside is connected is provided at a position below the intermediate extraction port G1.

(Treatment Device for Discharge Suspension from Bottom Part B)

In the device illustrated in FIG. 19, a transfer conduit 17 for the discharge suspension fed as the raw material substance of a digestion device D, or the like, for biomass in a discharge suspension consisting of a hydrolysis suspension containing the partially hydrolyzed biomass extracted to the discharge conduit 2 is connected to the discharge conduit 2 of the bottom part B of the continuous primary hydrolysis device R1 via a decompression valve VP. An extraction port G3 for a hydrolysis solution equipped with a solid-liquid separation device S3 at a position in front of the digestion device D is installed on the transfer conduit 17 for the discharge suspension. A circulation conduit 18 for a hydrolysis solution is connected to the extraction port G3, with one end being connected to the extraction port G3 and the other end being connected to the discharge conduit 2 of the bottom part B.

In addition, a biomass transfer conduit 14 for feeding the partially hydrolyzed biomass separated by the solid-liquid separation device S3 installed on the extraction port G3 to the digestion device D or the like is connected to the transfer conduit 17 for the discharge suspension.

Further, a conduit 16 (extraction conduit 16) capable of appropriately extracting part of the hydrolysis solution in the circulation conduit 18 is connected to an intermediate part of the circulation conduit 18 for a hydrolysis solution via a valve V9, and an aqueous liquid supply conduit 15 for supplying an aqueous liquid to the hydrolysis solution in the transfer conduit 18 from the aqueous liquid supply device W2 is connected to the downstream side of the connection region of the conduit 16 via a valve V8.

Figure 20:
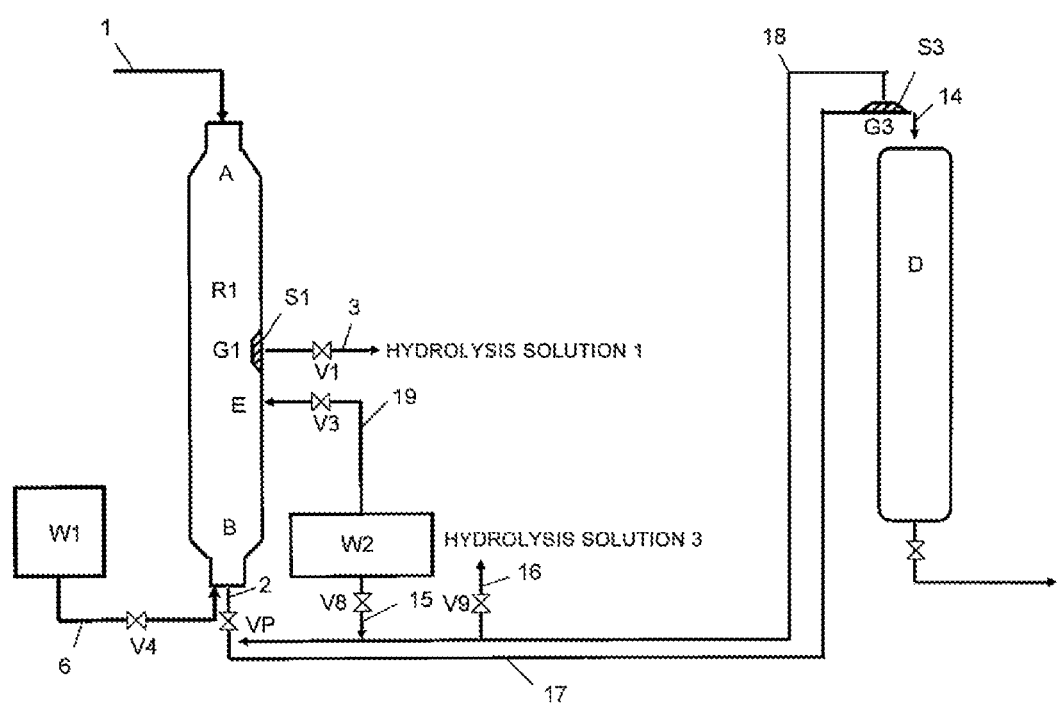
FIG. 20 illustrates a device for implementing the method for continuously manufacturing monosaccharides, oligosaccharides, and/or furfurals from biomass according to the present invention.

As illustrated in FIG. 20, an aqueous liquid supply port E is installed below the conduit 3 (extraction conduit 3) for the hydrolysis solution 1, which makes it possible to appropriately supply an aqueous liquid to the suspension condensed as a result of the hydrolysis solution 1 being extracted from the conduit 3.

In addition, as illustrated in FIG. 21, it is also possible to extract the hydrolysis solution 2 by disposing an extraction conduit 4 for the hydrolysis solution 2 connected to the second intermediate extraction port G2 at a position below the conduit 3. When extracting the hydrolysis solution 2 from the second intermediate extraction port G2 in this way, it is necessary to install an aqueous solution supply port E between the first intermediate extraction port G1 and the second intermediate extraction port G2 and to install an aqueous liquid supply conduit 19. By connecting the aqueous liquid supply conduit 19 between the first and second intermediate extraction ports and supplying an aqueous liquid to the aqueous liquid supply port E from the aqueous liquid supply device W2 at the same time that the extraction of the hydrolysis solution from the first intermediate extraction port G1 begins, it is possible to adjust the concentration of the suspension in the continuous primary hydrolysis device R1 to a state in which further hydrolysis of the biomass will progress smoothly.

The extracted liquid volume of the hydrolysis solution 2 from the extraction conduit 4 connected to the second intermediate extraction port G2 is not particularly limited and can be set appropriately based on the relationship with the volume of the countercurrent washing solution supplied to the bottom part B. In addition, in the case of a continuous primary hydrolysis device R1 having the intermediate extraction ports G1 and G2 at two locations, the countercurrent washing solution supplied from the bottom of the hydrolysis device moves upward from the bottom in the opposite direction as the movement direction of the hydrolysis suspension and is extracted to the extraction conduit 4 in a mixed state primarily with the hydrolysis solution 2 from the second intermediate extraction port G2 equipped with a solid-liquid separation device at an intermediate part of the device.

In the case of a continuous primary hydrolysis device R1 having two intermediate extraction ports G1 and G2 as described above, by extracting the hydrolysis solution 1 from the first intermediate extraction port G1 and simultaneously supplying an aqueous liquid of a liquid volume equivalent to the liquid volume of the extracted hydrolysis solution 1 to the continuous primary hydrolysis device R1, the hydrolysis conditions of the biomass between the first intermediate extraction port and the second intermediate extraction port are maintained favorably, and the amounts of monosaccharides, oligosaccharides, and furfurals extracted from the second intermediate extraction port G2 increase. It is therefore possible to manufacture monosaccharides, oligosaccharides, and furfurals with a higher yield than when extracted from only one intermediate extraction port G1 of the continuous primary hydrolysis device R1.

By employing a countercurrent washing operation based on the supply of a washing solution from the bottom part B, it is possible to move the water-soluble hydrolysates (monosaccharides, oligosaccharides, and furfurals) in the hydrolysis suspension moving to the bottom part B into the washing solution and to recover the solution as a hydrolysis solution extracted from the intermediate extraction port G1 (or G2) (hydrolysis solution 1 or hydrolysis solution 2). Accordingly, it is possible to reduce the amount of hydrolysates such as furfurals lost in association with the partially hydrolyzed biomass that is discharged from the bottom part B, fed to the digestion device D or the like by the transfer conduit 17 for the discharge suspension, and subjected to digestion.

Since at least some of the monosaccharides, oligosaccharides, and furfurals contained in the hydrolysis suspension can be recovered in the interval (the lower of the hydrolysis device) where the hydrolysates are washed in a countercurrent manner with the washing solution in the continuous primary hydrolysis device R1, the yield of the hydrolysates extracted from the extraction conduit increases. When the purpose of the hydrolysis solution extracted from the continuous primary hydrolysis device R1 is to increase the yield of a specific component of the hydrolysates, it is possible to feed the hydrolysis solution extracted to the extraction conduit to a secondary hydrolysis step and perform further hydrolysis in order to increase the content ratio of furfurals and monosaccharides, and it is also possible to feed the solution to a concentration/separation step for separating the furfurals, oligosaccharides, and monosaccharides directly.

(Treatment of Discharge Suspension at Bottom Part B)

By separating the hydrolysis solution from the discharge suspension transferred from the continuous primary hydrolysis device R1 to the digestion device D or the like, circulating the separated hydrolysis solution with the circulation conduit 18, combining the solution with the discharge suspension, and transferring the solution into the transfer conduit 17 in a state mixed with the discharge suspension, the hydrolysis of the biomass progresses during the transfer, and the content of the furfurals, oligosaccharides, and monosaccharides increases. However, the yield of hydrolysates increases further as a result of appropriately extracting a hydrolysis solution 3 containing the increased hydrolysates from the circulation conduit 18 for the hydrolysis solution. In addition, since the amounts of the monosaccharides, oligosaccharides, and furfurals accompanying the hydrolyzed biomass supplied to the digestion device D or the like can be reduced, there is the merit that decreases in the pH of the black liquor can be suppressed when the hydrolyzed biomass is used as a raw material for a digestion step D, which makes it possible to reduce the amount of alkali chemicals required to neutralize the black liquor.

The method for separating the hydrolysis solutions extracted from the continuous primary hydrolysis device R1 (hydrolysis solutions 1, 2, and the like) and furfurals and sugars from the hydrolysis solution (hydrolysis solution 3) subjected to additional hydrolysis in the discharge suspension transfer conduit for the bottom discharge suspension is not particularly limited, but it is preferable to extract each hydrolysis solution in a state in which the temperature and pressure at the time of hydrolysis are maintained, to feed the solution directly to a flash distillation device, and to separate the solution into a column top fraction consisting of a vapor phase containing furfurals and a column bottom fraction consisting of a liquid phase containing sugars or the like.

Since the vapor phase obtained as a column top fraction by the flash distillation device contains furfurals at a much higher concentration than the liquid fraction at the column bottom, it is possible to recover furfurals as a high-concentration furfural aqueous solution by simply cooling the vapor phase with a cooling device such as a condenser. An aqueous solution containing sugars consisting of oligosaccharides or monosaccharides, which are water-soluble hydrolysates, and organic acids such as acetic acid can be recovered from the liquid phase serving as a column bottom fraction of the flash distillation device.

Strainers or filters with a mesh (net) in the range of 10 µm to 5 cm are used as the solid-liquid separation devices (S1, S2, S3, and S4). The strainer that is used is preferably a strainer in the range of 40 to 5000 µm-40 to 500 µm, for example—in order to avoid clogging trouble and to avoid the accompaniment of suspended substances in the separated aqueous solution as much as possible.

(Continuous Primary Hydrolysis Conditions)

In the method of the present invention, the hydrolysis in the continuous primary hydrolysis device R1 may be performed using a method such as hot water treatment under pressure, acid treatment or alkali treatment, but a treatment using water or an acid aqueous solution in a pressurized and heated state is preferable in order to efficiently recover the monosaccharides, oligosaccharides, and furfurals that are produced. In the case of treatment using water in a pressurized and heated state, the biomass is mixed with water and hydrolyzed by pressurizing and heating. As a method of acid aqueous solution treatment, it is possible to mix the biomass with water containing an acid and to hydrolyze the solution by pressurizing and heating. The acid used in acid aqueous solution treatment is not particularly limited, and sulfuric acid, hydrochloric acid, nitric acid, phosphoric acid, acetic acid, oxalic acid, and the like can be used.

The pH of the aqueous suspension containing the biomass used for primary hydrolysis is preferably in the range of 0.5 to 5.0.

Although primary hydrolysis can be performed at a temperature of 120 to 250° C., the temperature is preferably from 140 to 230° C., more preferably from 150 to 190° C., and even more preferably from 150 to 180° C.

The pressure of primary hydrolysis is preferably from 0.35 MPa to 2.8 MPa.

The mass ratio of the aqueous liquid mixed with the biomass and the biomass (aqueous liquid/biomass) is preferably in the range of 2 to 8. An aqueous suspension raw material is prepared by mixing the biomass and the aqueous liquid, and the solution is then supplied to the primary hydrolysis device and hydrolyzed at a prescribed temperature and pressure in the primary hydrolysis device.

The hydrolysis time of the biomass is selected appropriately in accordance with the type of the biomass or the temperature or the like inside the continuous primary hydrolysis device R1. For example, when hydrolysis is performed at 140 to 230° C., the hydrolysis time is selected appropriately within the range of 0.5 to 180 minutes.

As a result of hydrolysis under the conditions described above, a hydrolysis suspension consisting of a hydrolysis solution containing the hydrolyzed biomass primarily consisting of cellulose, furfural, which is a hydrolysate of hemicellulose in the biomass, and various oligosaccharides and monosaccharides, which are hydrolysates of hemicellulose and cellulose, is obtained. In addition, a hydrolysis suspension containing a hydrolysis solution containing a hydrolyzed solid biomass and furfurals and pentoses (monosaccharides and oligosaccharides), which are hydrolysates of hemicelluloses and the like in the raw material biomass, is obtained.

Examples of the furfurals that are produced include furfural and 5-hydroxymethyl furfural. Examples of the oligosaccharides that are produced include xylooligosaccharides, cellooligosaccharides, and galactooligosaccharides, and these examples also include oligosaccharides in which arabinose, mannose, glucose, xylose, glucuronic acid, 4-o-methylglucuronic acid, or the like is added to the oligosaccharides described above as a side chain. Examples of the monosaccharides that are produced include xylose, arabinose, glucose, galactose, and mannose. Examples of monosaccharides in the pentoses that are produced include xylose and arabinose.

After part of the hydrolysis solution consisting of an aqueous solution containing water-soluble hydrolysates is separated from the hydrolysis suspension containing the biomass that is hydrolyzed in the continuous primary hydrolysis device R1 by the solid-liquid separation device installed at an intermediate position of the continuous primary hydrolysis device R1 and extracted to the conduit 3 (transfer line 3), the solution is discharged to the outside of the device from the hydrolysis suspension discharge conduit 2 (hydrolysis suspension recovery line 2) connected to the discharge port B of the continuous primary hydrolysis device R1 as a suspension (for example, a suspension containing the hydrolyzed biomass primarily consisting of cellulose). The hydrolysis solution containing the hydrolyzed biomass moving to the discharge port B from the solid-liquid separation device provided at an intermediate position of the continuous primary hydrolysis device R1 may also be washed by bringing the solution into contact with the washing solution supplied to the continuous primary hydrolysis device R1 from the washing solution supply device W1 via the washing solution supply conduit 6 in a countercurrent manner and then discharged from the discharge port B.

When performing continuous primary hydrolysis (prehydrolysis) with the continuous primary hydrolysis device R1 in order to manufacture dissolving pulp, continuous hydrolysis is performed under conditions suited to the manufacture of dissolving pulp (conditions under which the over-decomposition of cellulose is prevented), so there is a problem in that the furfurals, oligosaccharides, and monosaccharides obtained as by-products cannot be produced efficiently by primary hydrolysis alone.

However, by changing the position of the intermediate extraction port G1 provided on the side surface of the cylindrical part of the continuous primary hydrolysis device R1, as illustrated in FIG. 1, it is possible to control the production ratio of monosaccharides, oligosaccharides, and furfurals and the production volume of each component.

In addition, since the hydrolysis solution obtained with the continuous primary hydrolysis device R1 contains a sufficient amount of pentoses (monosaccharides and oligosaccharides), which are precursors of furfurals, it is possible to supply the solution to a secondary hydrolysis device and use the solution as a raw material for the manufacture of furfurals.

Further, by subjecting the hydrolysis solution obtained with the continuous primary hydrolysis device R1 to secondary hydrolysis, it is possible to efficiently produce furfurals, oligosaccharides, and monosaccharides concurrently with pulp production.

Alternatively, by performing hydrolysis under conditions under which the over-decomposition of cellulose can be avoided and subjecting the hydrolysis solution containing the resulting aqueous hydrolysates to additional hydrolysis so as to enable a change in the component ratio of each hydrolysate in the hydrolysis solution, it is possible to establish a method for concurrently producing specific hydrolysates such as furfurals, for example.

The furfural concentration in the hydrolysis solution immediately after being extracted to the conduit 3 from the intermediate extraction port G1 of the continuous primary hydrolysis device R1 illustrated in FIG. 1 is less than 3 mass %, and the concentration of SS (suspended substances) is at most 1 mass %.

In the present invention, as illustrated in FIG. 4, the hydrolysis suspension discharged to the discharge conduit 2 from the bottom discharge port B of the continuous primary hydrolysis device R1 contains useful components derived from biomass—in particular, a component primarily consisting of cellulose—as solid content. Accordingly, solid-liquid separation may be performed by installing a solid-liquid separation device S4 on the discharge conduit 2, and the hydrolysis solution portion may be fed to a recovery device for water-soluble hydrolysates via a discharge conduit 20. Via solid content transfer conduit 7, the solid content primarily consisting of cellulose can be used directly as a raw material for the manufacture of pulp or as a raw material for the manufacture of dissolving pulp, for example.

Since the solid content separated with the solid-liquid separation device S4 on the discharge conduit 2 connected to the bottom discharge port B is solid content primarily consisting of cellulose, it is also possible to establish a method for simultaneously manufacturing solid content primarily consisting of cellulose in a state that can be used as a raw material for the manufacture of paper pulp or a raw material for the manufacture of dissolving pulp as well as furfurals, oligosaccharides, and monosaccharides. When using the method primarily for the purpose of manufacturing such solid content primarily consisting of cellulose, the conditions suitable for the manufacture of paper pulp or dissolving pulp (conditions under which the over-decomposition of cellulose can be prevented) are not the optimal hydrolysis conditions for obtaining furfurals or monosaccharides. Therefore, in this case, it is possible to establish a method which makes it possible to concurrently produce a pulp raw material as well as furfurals and monosaccharides by subjecting the resulting hydrolysis solution to secondary hydrolysis to improve the content of furfurals and monosaccharides in the hydrolysis solution.

The hydrolysis solution extracted from the continuous primary hydrolysis device R1 can be further transferred to the next step such as a secondary hydrolysis step for controlling the production ratio of furfurals, oligosaccharides, and monosaccharides (for example, increasing the production ratio of each component) or a concentration/separation step for separating furfurals, oligosaccharides, and monosaccharides.

In this way, by further subjecting the resulting hydrolysis solution (primary hydrolysis solution) to secondary hydrolysis, it is possible to efficiently produce furfurals, oligosaccharides, and monosaccharides concurrently with pulp production.

Figure 12:
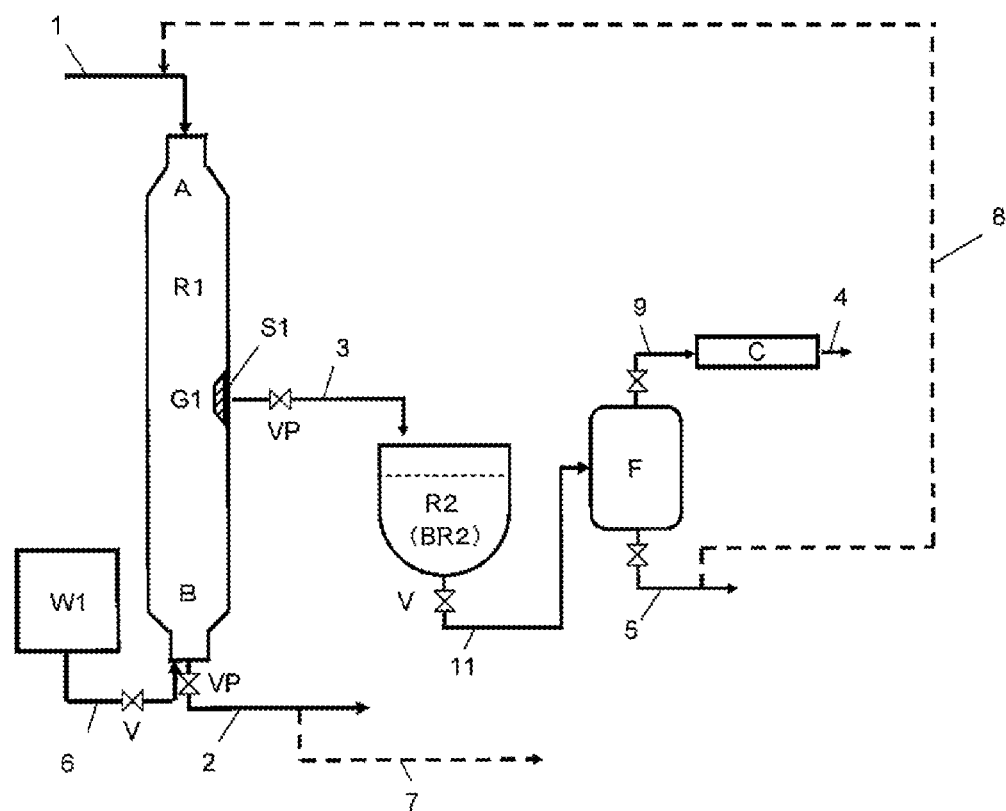
FIG. 12 illustrates an example of a device for implementing the method for manufacturing monosaccharides, oligosaccharides, and/or furfurals from biomass according to the present invention.

For example, as illustrated in FIG. 12, the primary hydrolysis solution extracted by the conduit 3 from the intermediate extraction port G of the continuous primary hydrolysis device R1 can be supplied to a secondary hydrolysis device R2 for producing furfurals by hydrolyzing pentoses including monosaccharides and oligosaccharides.

When performing secondary hydrolysis, the primary hydrolysis solution extracted from the intermediate extraction port of the continuous primary hydrolysis device R1 can be supplied directly to the secondary hydrolysis device, or the primary hydrolysis solution can be supplied to the secondary hydrolysis device after being concentrated using a concentration device such as a vacuum concentration device.

The hydrolysis solution extracted from the continuous primary hydrolysis device R1 can be transferred to a concentration/separation step and subjected to flash distillation by a concentration/separation device. A flash tank, a flash cyclone, or the like is used as the flash distillation device.

The vapor phase separated by flash distillation contains furfural at a higher content than the liquid phase, and the gaseous phase separated from this liquid phase can be cooled with a cooling device such as a condenser and recovered as a high-concentration furfural aqueous solution. An aqueous solution containing sugars consisting of oligosaccharides or monosaccharides, which are water-soluble hydrolysates, and organic acids such as acetic acid can be recovered from the bottom of the flash distillation device.

The solid content consisting of the biomass in the hydrolysis suspension discharged to the conduit 2 from the continuous primary hydrolysis device R1 (for example, solid content consisting of a biomass primarily made of cellulose) can be reused as a raw material for the manufacture of useful components derived from the biomass. In addition, since the solid content can be fed to a digestion step by the conduit 7 and used as a raw material for the manufacture of pulp, the hydrolysis method of the present invention can also be used as a prehydrolysis step serving as the step prior to kraft digestion in the dissolving pulp manufacturing process.

(Secondary Hydrolysis Device)

The secondary hydrolysis device used in the present invention is a continuous or batch hydrolysis device capable of continuously or intermittently hydrolyzing a primary hydrolysis solution under pressurization/heating conditions. The form of the secondary hydrolysis device is not particularly limited, but examples include a continuous secondary hydrolysis device R2 such as that illustrated in FIG. 6, the device comprising a temperature adjusting device T1 for adjusting the temperature of the primary hydrolysis device, and a constant temperature device T2 for maintaining the temperature at a constant level. The hydrolysis solution may be cooled by installing a cooling device CL for cooling the hydrolysis solution after hydrolysis behind the secondary hydrolysis device R2.

Figure 8:
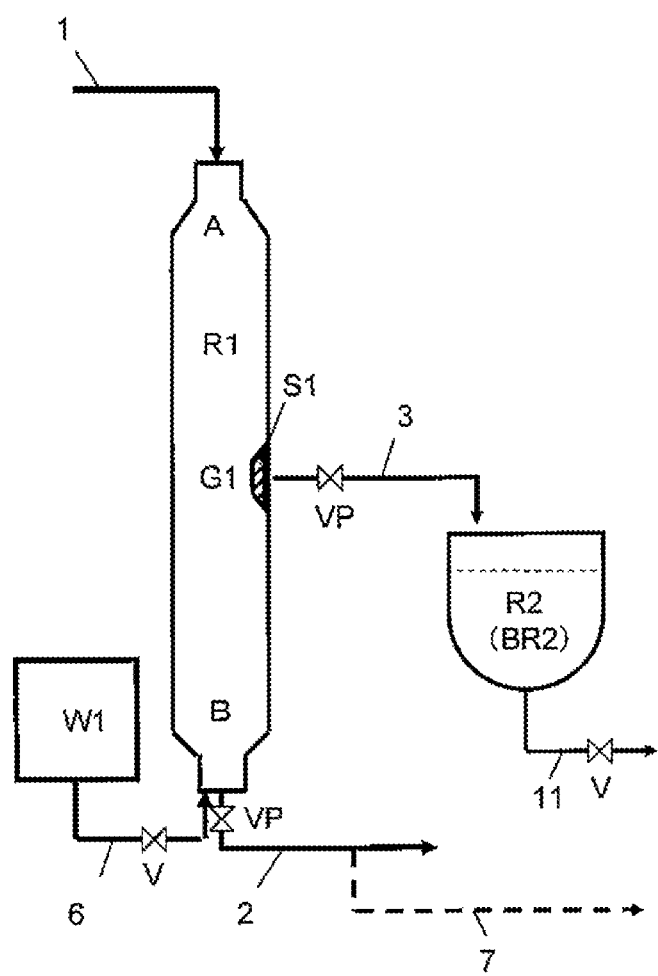
FIG. 8 illustrates an example of a device for implementing the method for continuously manufacturing monosaccharides, oligosaccharides, and/or furfurals from biomass according to the present invention.

Another example of the secondary hydrolysis device is a secondary reaction vessel BR2 such as that illustrated in FIGS. 8, 12, and 16.

A plurality of secondary hydrolysis devices R2 may also be installed in parallel or in series. Primary hydrolysis solutions may also be treated simultaneously with a plurality of secondary hydrolysis device R2.

Figure 6:
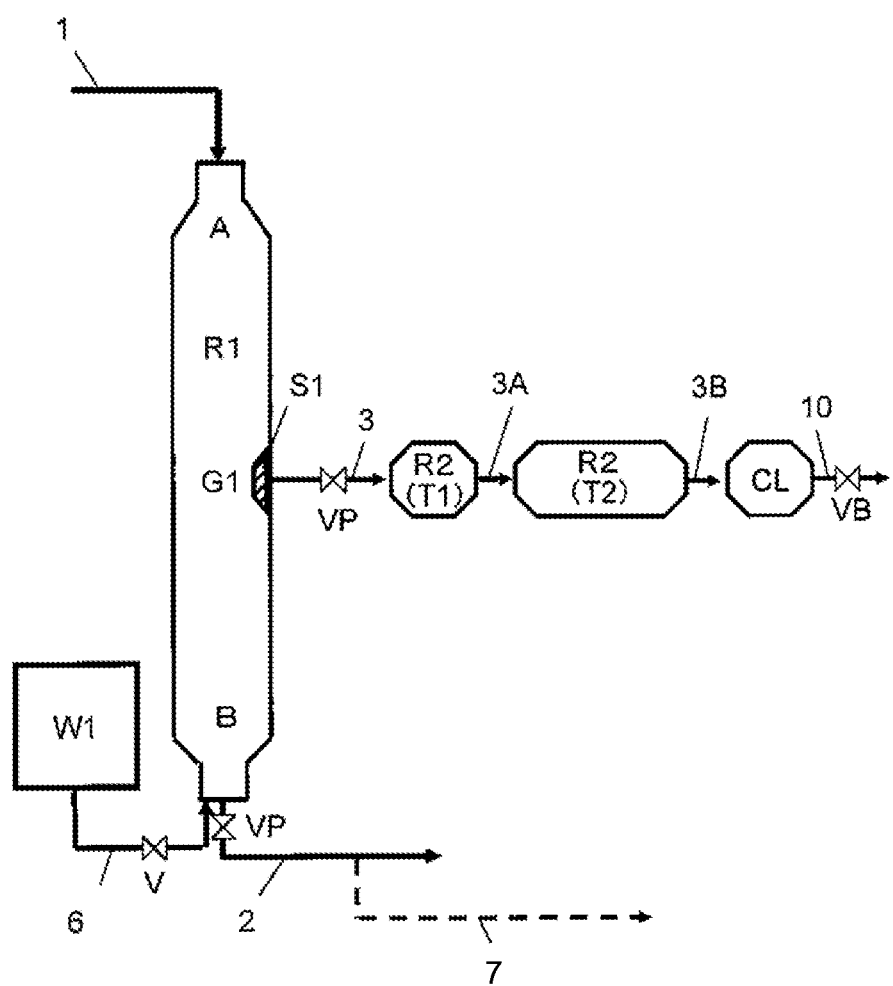
FIG. 6 illustrates an example of a device for implementing the method for continuously manufacturing monosaccharides, oligosaccharides, and/or furfurals from biomass according to the present invention.

In the device illustrated in FIG. 6, the primary hydrolysis solution is continuously supplied from the intermediate extraction port G1 of the continuous primary hydrolysis device R1 to which the conduit 3 (primary hydrolysis solution transfer conduit 3) is connected to the secondary hydrolysis device R2 (T1-T2), where hydrolysis is performed under pressure/heating in the state of an aqueous solution. The solution is moved through the device while being subjected to hydrolysis by T2 and is continuously discharged from a discharge port to which another secondary hydrolysis solution transfer conduit 10 is connected.

In the device illustrated in FIG. 8, the primary hydrolysis solution is continuously or intermittently supplied from the intermediate extraction port G1 of the continuous primary hydrolysis device R1 to which the conduit 3 is connected to the secondary reaction vessel BR, where hydrolysis is performed under pressure/heating in the state of an aqueous solution. The solution is then moved through the device while being subjected to hydrolysis in the reaction vessel BR and is discharged from a discharge port to which another secondary hydrolysis solution transfer conduit 11 is connected. A plurality of the aforementioned secondary hydrolysis devices can be installed in parallel, and primary hydrolysis solutions may also be treated simultaneously with a plurality of secondary hydrolysis devices.

When the pressure inside the continuous primary hydrolysis device R1 is higher than the pressure inside the secondary hydrolysis device R2, the primary hydrolysis solution is transferred to the secondary hydrolysis device by a decompression valve VP. On the other hand, when the pressure inside the continuous primary hydrolysis device R1 is lower than the pressure inside the secondary hydrolysis device R2, the primary hydrolysis solution is transferred to the secondary hydrolysis device by a valve V using a pump (not illustrated). The secondary hydrolysis solution can be discharged after being cooled by the cooling device CL or can be discharged to the outside of the system by a back pressure valve VB without being cooled. A device capable of supplying an acid or alkali solution for adjusting the pH of the primary hydrolysis solution before the primary hydrolysis solution is supplied to the secondary hydrolysis device R2 may be connected to the conduit 3. The secondary hydrolysis solution may be continuously fed to the next step, such as a concentration/recovery step for the produced furfural, and may also be stored in a tank or the like.

In the device illustrated in FIG. 12, the raw material biomass is continuously supplied to the continuous primary hydrolysis device R1 from the supply port A to which the raw material suspension supply conduit 1 is connected in the state of an aqueous suspension and is moved through the device while being subjected to hydrolysis under pressurization/heating conditions. The solution is continuously discharged as a hydrolysis suspension containing the hydrolyzed biomass from the discharge port B to which the hydrolysis suspension discharge conduit 2 is connected. A hydrolysis solution containing water-soluble hydrolysates separated from the hydrolysis suspension moving through the device is extracted from the intermediate extraction port G1 equipped with a solid-liquid separation device installed at an intermediate point of the device between the supply port A and the discharge port B while maintaining the pressure and temperature of hydrolysis, and the solution is then fed to the secondary hydrolysis device R2 (secondary reaction vessel BR2).

In the continuous primary hydrolysis device R1 illustrated in FIG. 12, an aqueous liquid supply port E for supplying an aqueous liquid can be provided at a position below the intermediate extraction port G1 in order to resupply an aqueous liquid of the same type as the aqueous liquid used in the raw material suspension to the hydrolysis suspension in the device after a portion of the hydrolysis solution is extracted from the intermediate extraction port G1.

In the continuous primary hydrolysis device R1 illustrated in FIG. 12, the intermediate extraction port G1 is provided at only one location on the side surface of the cylindrical part of the continuous primary hydrolysis device R1, but this intermediate extraction port G1 is not limited to one location and may be provided at two or more positions. For example, the hydrolysis device may be configured so that a second intermediate extraction port G, capable of separating only the hydrolysis solution portion and extracting the solution to the outside of the device, is provided at a position below the intermediate extraction port G1. In addition, when a third intermediate extraction port G is further provided, an aqueous liquid supply port may also be provided between the second intermediate extraction port and the third intermediate extraction port, which makes it possible to supply an aqueous liquid to the continuous primary hydrolysis device R1 as necessary.

In the device illustrated in FIG. 12, the primary hydrolysis solution is extracted to the primary hydrolysis solution extraction conduit 3 from the intermediate extraction port G1 of the continuous primary hydrolysis device R1 in the state of an aqueous solution and is then supplied to the secondary reaction vessel BR2 (R2), where pentoses are hydrolyzed under pressure/heating.

In the device illustrated in FIG. 16, the primary hydrolysis solution is extracted from the intermediate extraction port G1 of the continuous primary hydrolysis device R1, to which the extraction conduit 3 is connected, in the state of an aqueous solution and is then supplied to the secondary reaction vessel BR2, where hydrolysis is performed under pressure/heating.

The supply of the primary hydrolysis solution to the secondary reaction vessel BR2 may be continuous or intermittent.

(Secondary Hydrolysis Conditions)

In the method of the present invention, the hydrolysis in the secondary hydrolysis device R2 may be performed using a method such as hot water treatment under pressure, acid treatment or alkali treatment, but a treatment using water or an acid aqueous solution in a pressurized and heated state is preferable in order to efficiently recover the monosaccharides, oligosaccharides, and furfurals that are produced. In the case of treatment using water in a pressurized and heated state, the biomass is mixed with water and hydrolyzed by pressurizing and heating. As a method of acid aqueous solution treatment, it is possible to mix the biomass with water containing an acid and to hydrolyze the solution by pressurizing and heating. Alternatively, water containing an acid may be mixed with the primary hydrolysis solution, and the solution may be hydrolyzed by pressurizing and heating the solution. The acid used in acid aqueous solution treatment is not particularly limited, and sulfuric acid, hydrochloric acid, nitric acid, phosphoric acid, acetic acid, oxalic acid, and the like can be used.

The pH of the primary hydrolysis solution used for secondary hydrolysis is preferably in the range of 0.5 to 5.0.

Although hydrolysis can be performed at a temperature of 120 to 250° C., the temperature is preferably from 140 to 230° C., more preferably from 160 to 200° C., and even more preferably from 170 to 200° C. When the temperature exceeds 230° C., furfural polymerizes and the loss of furfural tends to progress, which is not preferable. The pressure is preferably from 0.35 to 2.8 MPa.

The retention time of the primary hydrolysis solution supplied to the secondary hydrolysis device R2 illustrated in FIG. 6 (the time required to pass through the T2 portion, which maintains the temperature of the secondary hydrolysis device at a constant level) is preferably from 1 to 180 minutes and more preferably from 5 to 120 minutes. The primary hydrolysis solution supplied to the secondary hydrolysis device is treated at a prescribed temperature for a prescribed amount of time in the secondary hydrolysis device so that a hydrolysis solution containing monosaccharides, oligosaccharides, and furfurals at the desired ratio is obtained.

The secondary hydrolysis in the secondary hydrolysis device illustrated in FIG. 12 must be performed under conditions under which pentoses are left behind in the hydrolysis solution discharged from the secondary hydrolysis device at a ratio of at least 1% with respect to the mass of all pentoses contained in the solution prior to secondary hydrolysis, including the primary hydrolysis solution supplied to the secondary hydrolysis device. Secondary hydrolysis must be performed so that the ratio of the mass of all pentoses contained in the hydrolysis solution after secondary hydrolysis with respect to the mass of all pentoses contained in the supplied solution prior to secondary hydrolysis is in the range of 1 to 30% as a numerical value calculated in accordance with the following formula. In particular, secondary hydrolysis is preferably performed so that the ratio is in the range of 5 to 30% and more preferably performed so that the ratio is in the range of 5 to 20%.

Ratio(%)="(mass of all pentoses in the secondary hydrolysis solution discharged from the discharge port of the secondary hydrolysis device/mass of all pentoses contained in the solution supplied to the secondary hydrolysis device)× 100 <Formula>

When a batch-type secondary hydrolysis device is used, it is preferable to perform secondary hydrolysis so that the ratio of the mass of all pentoses contained in the hydrolysis solution at the point when secondary hydrolysis is completed with respect to the mass of all pentoses contained in the hydrolysis solution before secondary hydrolysis is begun is in the range of 5 to 30%, and it is even more preferable to perform secondary hydrolysis so that the ratio is in the range of 5 to 20%.

When a continuous-type secondary hydrolysis device is used, in FIG. 12, it is necessary to perform secondary hydrolysis so that the ratio of the mass of all pentoses contained in the hydrolysis solution (conduit 11) discharged from the secondary hydrolysis device (secondary reaction vessel BR2) with respect to the mass of all pentoses contained in the hydrolysis solution (conduit 3) supplied to the secondary hydrolysis device (secondary hydrolysis kettle BR2) is in the range of 5 to 30%. It is preferable to perform secondary hydrolysis so that the ratio is in the range of 5 to 20%, and it is even more preferable to perform secondary hydrolysis so that the ratio is in the range of 5 to 20%.

By performing secondary hydrolysis so that the ratio of the mass of all pentoses contained in the hydrolysis solution after secondary hydrolysis with respect to the mass of all pentoses contained in the solution supplied to the secondary hydrolysis device, including the primary hydrolysis solution prior to secondary hydrolysis, is in the range of 5 to 30%, it is possible to suppress side reactions of the sugars and furfurals contained in the hydrolysis solution and thus improve the production efficiency of furfurals.

The secondary hydrolysis solution extracted from the secondary hydrolysis device is transferred to the concentration/separation device, and the hydrolysis solution is separated into a vapor phase and a liquid phase by the concentration/separation device so that the furfurals contained in the vapor phase can be recovered.

When secondary hydrolysis is performed with a batch method using the device illustrated in FIG. 16, the valve V (vapor phase transfer conduit 21) above the secondary hydrolysis device (secondary reaction vessel BR2) is opened after secondary hydrolysis. The vapor phase is extracted and transferred to a distillation device EV, and a furfural concentrate is separated by the distillation device EV. On the other hand, when performed with a continuous method, the vapor phase is extracted by opening a decompression valve, while performing secondary hydrolysis, using a decompression valve instead of the valve V (vapor phase transfer conduit 21) above the secondary hydrolysis device (secondary reaction vessel BR2). The vapor phase is transferred to the distillation device EV, and a concentrate containing furfurals is separated by the distillation device EV. The vapor phase extracted from the secondary hydrolysis device (batch or continuous) may be condensed with a condenser C (condenser) prior to being transferred to the distillation device EV. The distillation device EV for distilling and concentrating the vapor phase containing furfurals is a device formed by installing a plurality of devices in series or in parallel. The method for distilling the vapor phase extracted from the secondary hydrolysis device with the distillation device makes it possible to reduce the time required for distillation since the liquid volume to be distilled can be reduced in comparison to a method of distilling the secondary hydrolysis solution (liquid phase) directly with a distillation device, and the energy required for distillation can also be reduced, which yields the merit that the productivity of furfurals, monosaccharides, and oligosaccharides increases.

The liquid phase from which the vapor phase is separated in the secondary hydrolysis device primarily contains monosaccharides or oligosaccharides. The liquid phase from which the vapor phase is removed can be extracted to the liquid phase extraction conduit 11 and transferred to a step for separating/purifying oligosaccharides or monosaccharides, and the liquid phase may also be stored in a tank or the like. When stored in a tank or the like, a cooling device for cooling an aqueous solution containing sugars or the like extracted as a liquid phase may be installed behind the secondary hydrolysis device.

In addition, when furfurals are produced from oligosaccharides or monosaccharides in a transfer conduit or the like after being extracted to the liquid phase extraction conduit 11, it is also possible to transfer the solution to the concentration/separation device or the distillation device and to separate and recover the furfurals. A flash tank, a flash cyclone, or the like is used as the concentration/separation device.

Since the liquid phase from which the vapor phase is removed contains organic acids such as acetic acid, which promote biomass hydrolysis, in addition to sugars consisting of oligosaccharides or monosaccharides as the primary components, it is also possible to circulate and mix the solution into the raw material suspension in the raw material suspension supply conduit 1 at the top of the continuous primary hydrolysis device R1 via a circulation conduit 22 for an aqueous solution containing sugars or the like, as illustrated in FIG. 16.

When a liquid phase consisting of an aqueous solution containing sugars or the like from which the vapor phase is removed is circulated and supplied to the primary hydrolysis device, the oligosaccharides or monosaccharides contained in the liquid phase are decomposed into furfurals. In addition, the hydrolysis of monosaccharides and oligosaccharides is accelerated by primary hydrolysis with an organic acid, which improves the yield of furfural.

Figure 18:
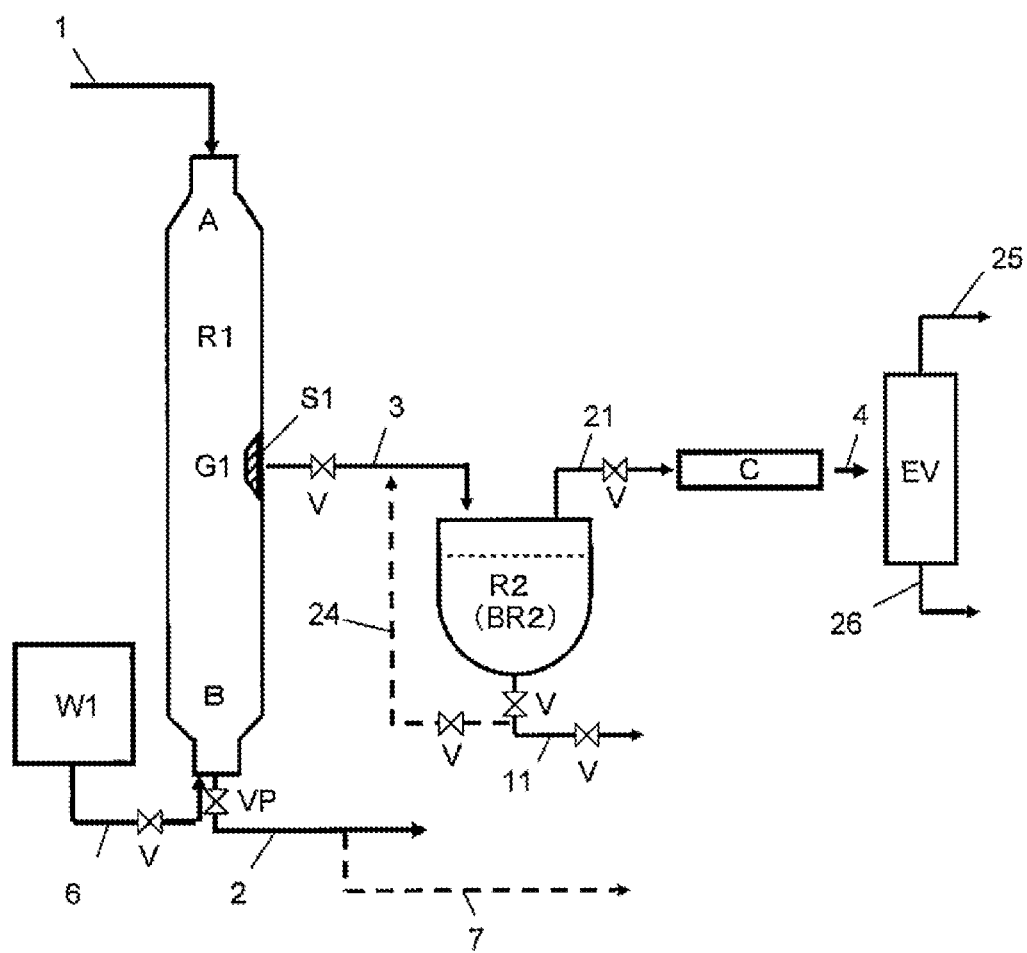
FIG. 18 illustrates an example for implementing the method for manufacturing monosaccharides, oligosaccharides, and/or furfurals from biomass according to the present invention.

As illustrated in FIG. 18, it is also possible to circulate and supply an aqueous solution containing sugars or the like extracted as a liquid phase from which the vapor phase is removed to the supply conduit (primary hydrolysis solution extraction conduit 3) of the secondary hydrolysis device via a circulation conduit 24 for an aqueous solution containing sugars or the like. By supplying the liquid phase from which the vapor phase is removed (aqueous solution containing sugars or the like) to the primary hydrolysis solution supplied to the secondary hydrolysis device, the oligosaccharides or monosaccharides are decomposed into furfurals. In addition, the hydrolysis of monosaccharides and oligosaccharides is accelerated by secondary hydrolysis with an organic acid, which improves the yield of furfural.

As illustrated in FIG. 16, the liquid phase from which the vapor phase is removed (aqueous solution containing sugars or the like) can be transferred to a boiler (recovery boiler BO) for recovering energy with a transfer conduit 27 for an aqueous solution containing sugars or the like branching from the circulation conduit 22 for an aqueous solution containing sugars or the like and then recovered as energy. An example of a boiler in a pulp manufacturing process is a black liquor recovery boiler. The aqueous solution containing sugars or the like from the secondary hydrolysis device may be concentrated by a decompression/concentration device or the like prior to being transferred to the boiler.

The energy recovered by the recovery boiler can be utilized in the manufacturing process for furfurals, monosaccharides, and oligosaccharides.

In order to recover furfurals remaining in the liquid phase from which the vapor phase is removed by the secondary hydrolysis device (aqueous solution containing sugars or the like) and furfurals that may be newly produced during the process, it is possible to transfer the aqueous solution containing sugars or the like to a step for recovering an additional amount of furfurals and to then treat the solution.

The hydrolysis solution extracted from the continuous primary hydrolysis device R1 or the secondary hydrolysis solution obtained by secondary hydrolysis can be transferred to a step for continuously separating and recovering monosaccharides, oligosaccharides, and furfurals with a concentration/separation device or the like or may also be stored in a tank or the like.

(Concentration/Separation Device)

When separating furfurals and sugars from the hydrolysis solution extracted from the continuous primary hydrolysis device R1 and the hydrolysis solution obtained by secondary hydrolysis, it is preferable to extract each hydrolysis solution in a state in which the temperature and pressure at the time of hydrolysis are maintained, to feed the solution directly to a flash distillation device, and to separate the solution into a vapor phase containing furfurals and a liquid phase containing sugars.

Figure 5:
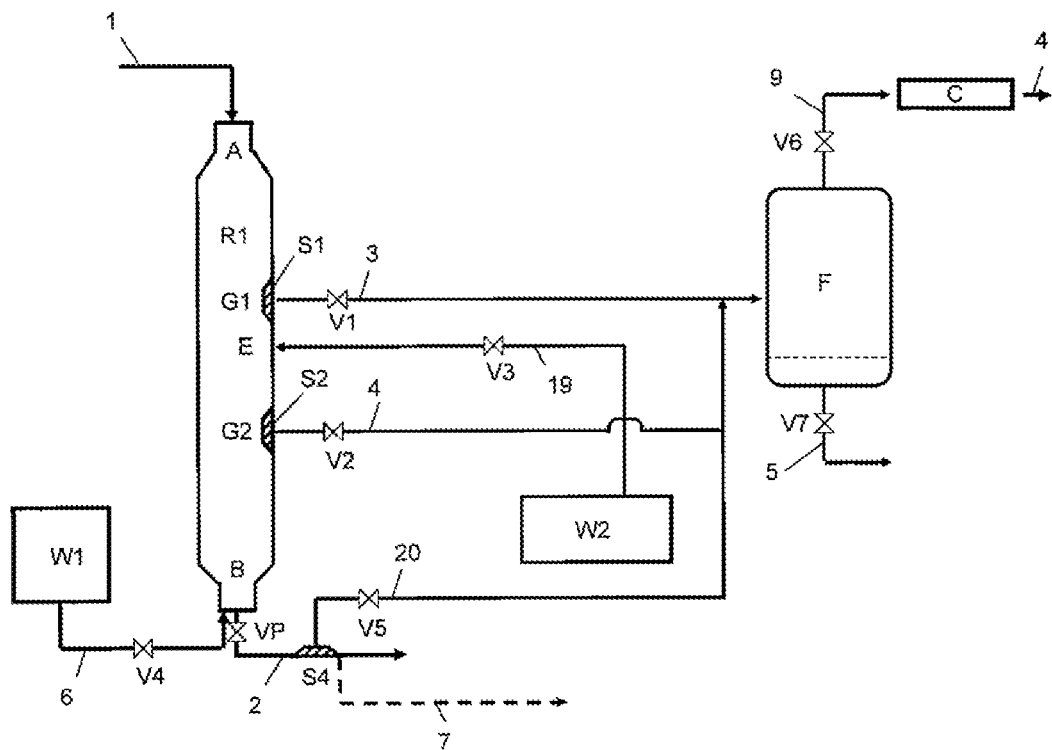
FIG. 5 illustrates a device for implementing the method for continuously manufacturing monosaccharides, oligosaccharides, and/or furfurals from biomass according to an embodiment of the present invention.

For example, in the "method for continuously manufacturing monosaccharides, oligosaccharides, and furfurals from biomass" of the present invention using the continuous primary hydrolysis device R1 illustrated in FIGS. 3 and 4, the hydrolysis solution 1 extracted to the extraction conduit 3 from the intermediate extraction port G1 of the continuous primary hydrolysis device R1, the hydrolysis solution 2 extracted to the extraction conduit 4 from the intermediate extraction port G2, and the hydrolysis solution 3 extracted to the extraction conduit 20 after the hydrolysis suspension extracted to the discharge conduit 2 from the bottom discharge port B illustrated in FIG. 4 is separated into solids and liquids by the solid-liquid separation device S4 are pooled together as illustrated in FIG. 5 so that the solutions can be fed to a concentration/separation device F (flash tank) or a distillation device.

The vapor phase is then fed to a condenser C by a vapor phase transfer conduit 9 after distillation in the flash tank or the like, and the vapor phase is condensed and liquefied. After the vapor phase is extracted by a furfural aqueous solution extraction conduit 4 as a high-concentration furfural aqueous solution, the furfurals are recovered, and sugars such as monosaccharides and oligosaccharides are extracted to a sugar solution extraction conduit 5 from the bottom of the tank and recovered.

Figure 7:
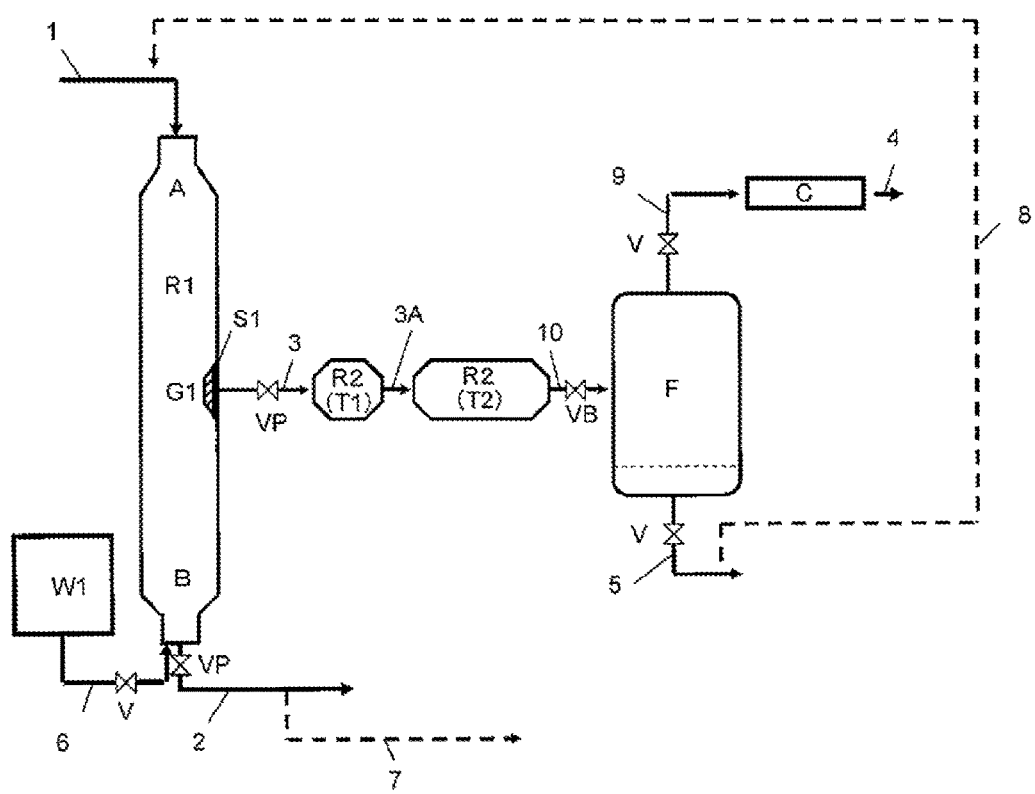
FIG. 7 illustrates another example of a device for implementing the method for continuously manufacturing monosaccharides, oligosaccharides, and/or furfurals from biomass according to the present invention.
Figure 9:
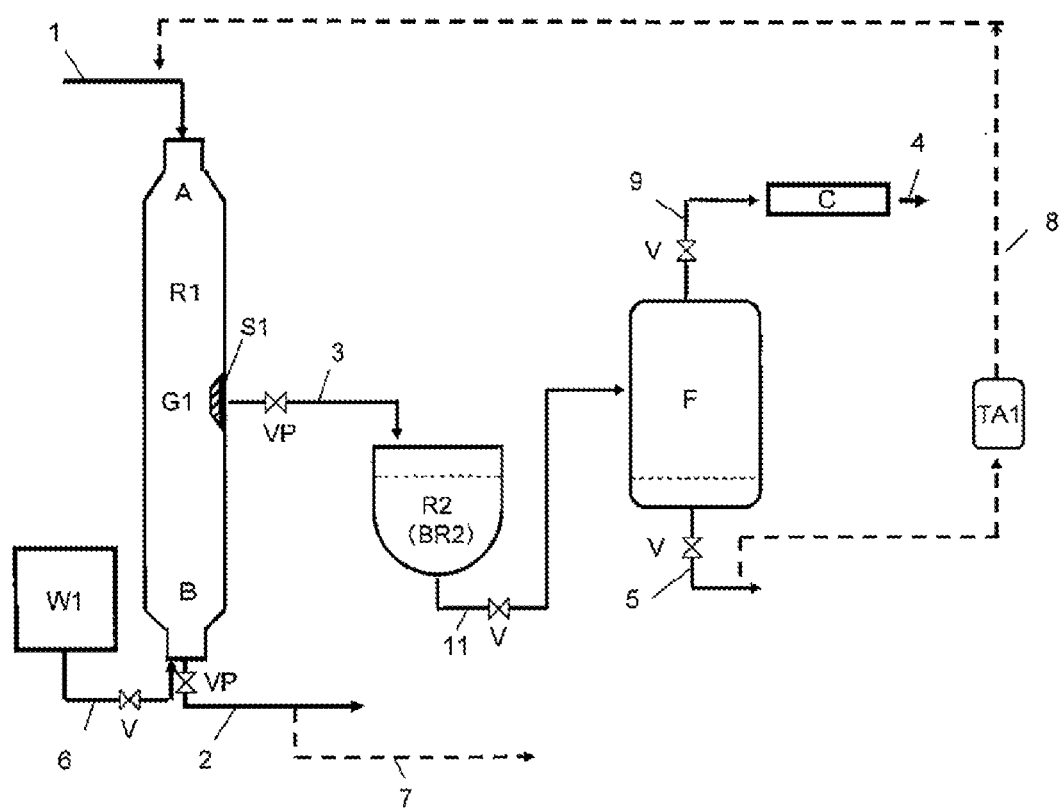
FIG. 9 illustrates another example of a device for implementing the method for continuously manufacturing monosaccharides, oligosaccharides, and/or furfurals from biomass according to the present invention.

The devices illustrated in FIGS. 7 and 9 are equipped with a concentration/separation device for the furfural contained in the secondary hydrolysis solution. The secondary hydrolysis solution from the secondary hydrolysis device R2 (T2) is fed directly to the concentration/separation device F by the transfer conduit 10 without being cooled by the cooling device CL, and the solution is subjected to flash distillation therein. The device of FIG. 9 illustrates an example in which the secondary hydrolysis solution fed from the secondary reaction vessel BR is fed directly to the concentration/separation device by the transfer conduit 11 without being cooled, and the solution is subjected to flash distillation therein.

As illustrated in FIG. 12, the secondary hydrolysis solution extracted to the secondary hydrolysis solution extraction conduit 11 from the bottom of the secondary hydrolysis device BR2 is transferred to the concentration/separation device F (flash tank or the like) and is separated into a vapor phase and a liquid phase by flash distillation or the like in the concentration/separation device. The vapor phase extracted to the vapor phase extraction conduit 9 from the top of the concentration/separation device F is condensed by the condenser C (condenser), and an aqueous solution containing furfural is recovered by the condensate extraction conduit 4. An aqueous solution containing sugars such as oligosaccharides or monosaccharides in the secondary hydrolysate or organic acids such as acetic acid is recovered from the liquid phase extraction conduit 5 at the bottom of the concentration/separation device F.

The aqueous solution containing sugars or the like recovered from the conduit 5 at the bottom of the concentration/separation device F may also be fed to a step for separating/purifying oligosaccharides and monosaccharides and then treated. In addition, as illustrated in FIG. 12, it is also possible to circulate at least part of the aqueous solution containing sugars or the like recovered from the liquid phase extraction conduit 5 at the bottom of the concentration/separation device F to the raw material suspension supply conduit 1 as an aqueous solution for preparing a biomass raw material suspension using the circulation conduit 8 for an aqueous solution containing sugars or the like, and to then use the solution as part of an aqueous liquid for preparing a raw material suspension. The yield of furfural can be improved by circulating the aforementioned aqueous solution containing sugars or the like.

Figure 22:
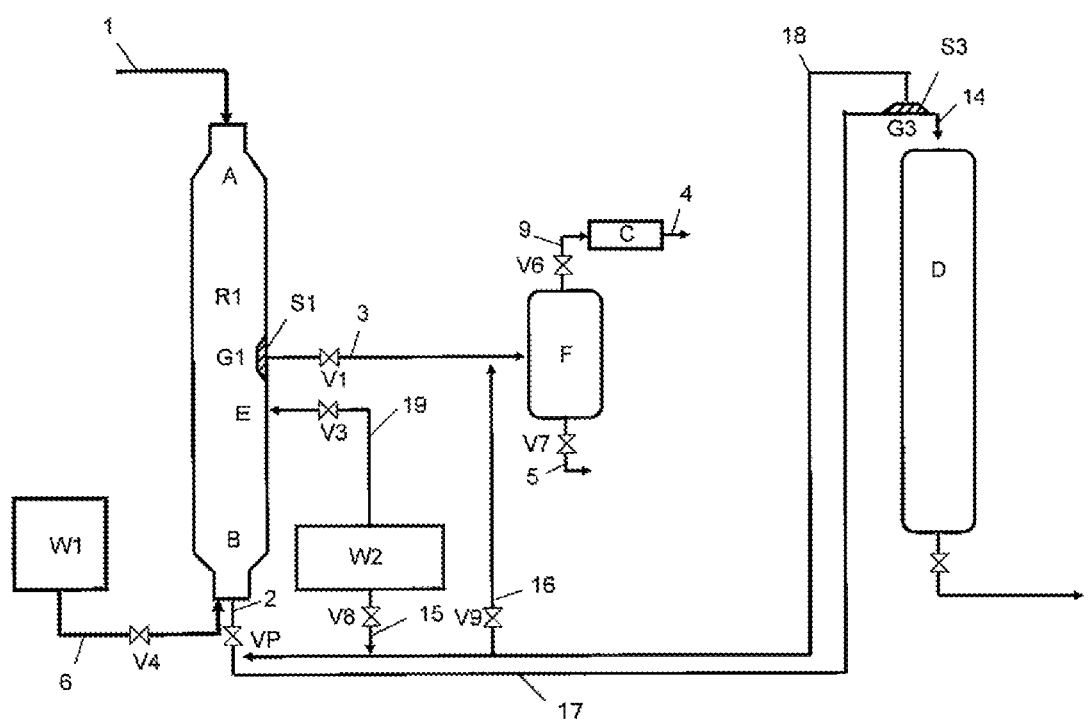
FIG. 22 illustrates a device for implementing the method for continuously manufacturing monosaccharides, oligosaccharides, and/or furfurals from biomass according to the present invention.
Figure 23:
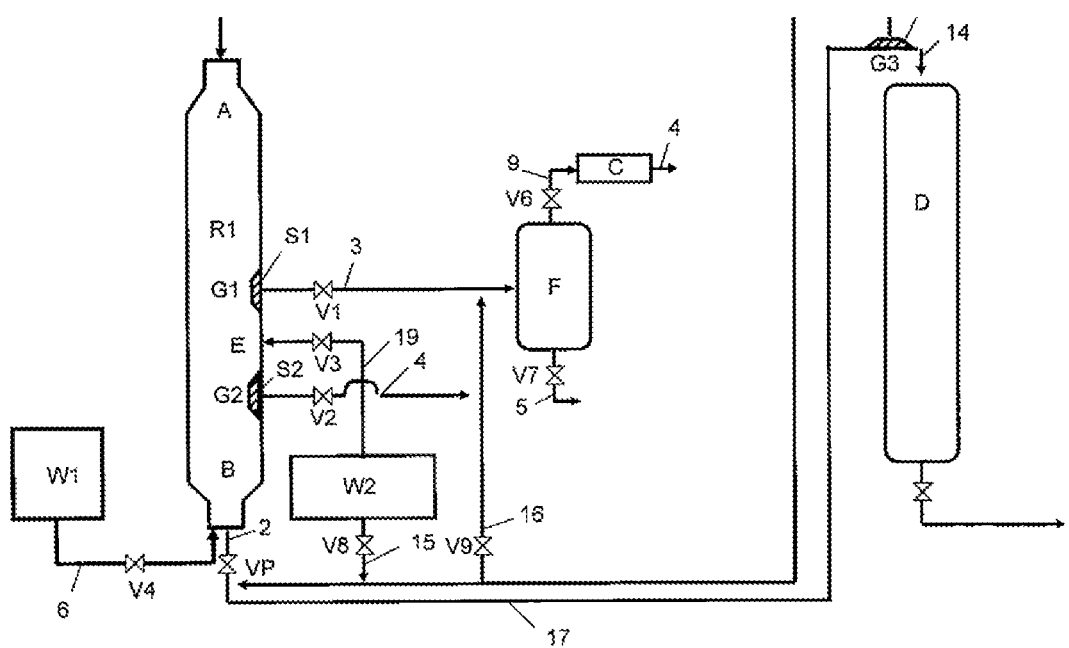
FIG. 23 illustrates a device for implementing the method for continuously manufacturing monosaccharides, oligosaccharides, and/or furfurals from biomass according to the present invention.

In the devices illustrated in FIGS. 22 and 23, the hydrolysis solutions (hydrolysis solutions 1 and 2) extracted by the conduit 3 and/or the conduit 4 connected to the continuous primary hydrolysis device R1 and the hydrolysis solution (hydrolysis solution 3) extracted from the extraction conduit 16, which is further connected to the circulation conduit 18 for the hydrolysis solution connected to the discharge suspension transfer conduit 17, are preferably fed to the concentration/separation device F (distillation device F) in a mixed state.

The concentration/separation device F consists of a flash tank, for example. A condenser C for condensing the vapor fraction is connected to the top part thereof via a transfer conduit 9 for the vapor fraction having a valve V6, and an extraction conduit 4 for the condensate is connected to the condenser C. In addition, an extraction conduit 5 for the liquid fraction which extracts the liquid fraction in the distillation device and has a valve V7 is connected to the bottom of the concentration/separation device F. The concentration/separation device F is not limited to a flash tank, and any device may be used without any particular limitation as long as the device is a distillation device capable of efficiently separating each component contained in the hydrolysis solution.

The method for continuously manufacturing sugars and furfurals from biomass with the continuous primary hydrolysis device R1 illustrated in FIGS. 19 to 23 and a hydrolysate recover device integrally linked to the hydrolysis device will be described hereinafter.

In FIG. 19, a raw material suspension prepared by suspending biomass in an aqueous liquid is continuously supplied to the top part A of the continuous primary hydrolysis device R1 by the supply conduit 1 for the raw material suspension. The solution is hydrolyzed while moving through the device in the direction of the bottom part B in a state in which temperature and pressure conditions enabling the hydrolysis of the biomass are maintained, and the solution is extracted from the bottom part B by an extraction conduit 2 having a decompression valve VP as a discharge suspension consisting of a hydrolysis suspension containing the partially hydrolyzed biomass and aqueous hydrolysates. The raw material suspension prepared by suspending the biomass in the aqueous liquid is supplied as a suspension containing 0.5 to 10 parts by mass of the aqueous liquid per 1 part by mass of the biomass (dry).

At the intermediate extraction port G1 having a solid-liquid separation device S1 formed at an intermediate point between the top part A and the bottom part B of the continuous primary hydrolysis device R1, the valve V1 of the extraction conduit 3 is opened so that the hydrolysis solution 1 in which the hydrolysates are dissolved is extracted from the hydrolysis suspension moving through the device in a state in which the hydrolysis of the biomass has progressed, and the valve V4 of the washing solution supply conduit 6 is simultaneously opened so that a washing solution is supplied to the bottom part B from the washing solution supply device W1. The washing solution that is supplied makes contact in a countercurrent manner with the hydrolysis suspension traveling downward through the hydrolysis device, and at least some of the hydrolysates in the hydrolysis suspension are captured and extracted by the extraction conduit 3 in a state in which the hydrolysates are contained in the hydrolysis solution from the intermediate extraction port G1.

The liquid volume of the hydrolysis solution 1 extracted from the continuous primary hydrolysis reaction device R1 by the intermediate extraction port G1 is typically from 0.5 to 10 parts by mass and preferably in the range of 2 to 6 parts by mass per 1 part by mass of the biomass (dry) in the hydrolysis suspension. The supply volume of the countercurrent washing solution is not particularly limited, but the supply volume is set appropriately within a range in which the concentration of the hydrolysis solution 1 extracted from the extraction conduit 3 does not become excessively diluted. The solution used as a concurrent washing solution may be an aqueous liquid of the same type as the aqueous liquid used in the raw material suspension, an acidic aqueous solution containing an organic acid, a weak alkaline aqueous solution, warm water, or the like, and solutions heated in advance are preferable. The washing solution from the washing solution supply conduit 6 may be supplied continuously or intermittently.

Figure 24:
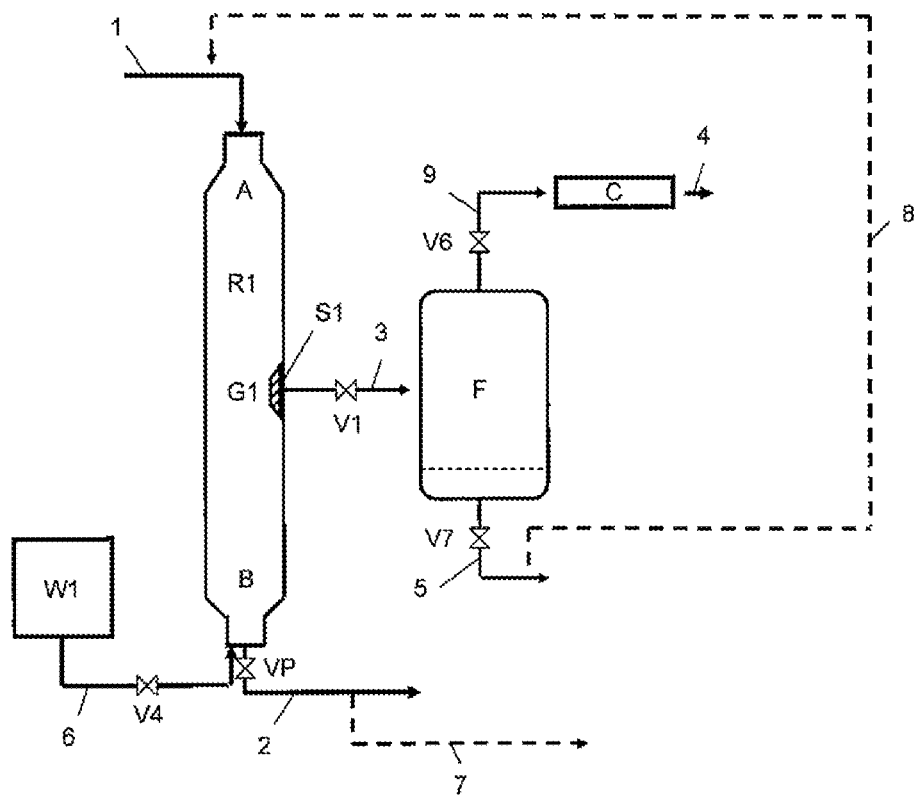
FIG. 24 illustrates a device for implementing the method for continuously manufacturing monosaccharides, oligosaccharides, and/or furfurals from biomass according to the present invention.

In the method illustrated in FIG. 24, the primary hydrolysis solution is fed to the concentration/separation device F by the conduit 3 and separated into furfurals (gaseous phase) and sugars (liquid phase). The sugars primarily include oligosaccharides and monosaccharides.

A flash tank, a flash cyclone, a distillation column, an evaporator, or the like is used as the concentration/separation device F (for example, a flash distillation device). A flash tank or a flash cyclone is preferable for concentrating the solution by utilizing the energy from the secondary hydrolysis device. In a flash tank, a hydrolysis solution consisting of an aqueous solution containing hydrolysates fed while maintaining the pressure and temperature inside the primary hydrolysis device or the secondary hydrolysis device is separated into a gas and a liquid by flash distillation. The vapor phase extracted from the top of the tank to the vapor phase transfer conduit 9 (vapor line 9) is condensed by the condenser C, and an aqueous solution containing furfural is recovered by the condensate extraction conduit 4 (furfural aqueous solution recovery line 4). An aqueous solution containing sugars consisting of oligosaccharides or monosaccharides, which are hydrolysates, or organic acids such as acetic acid is recovered from the liquid phase extraction conduit 5 (recovery line 5 for an aqueous solution containing sugars or the like) at the bottom of the concentration/separation device F.

The vapor phase separated by flash distillation contains furfural at a higher content than the liquid phase, and the gaseous phase separated from this liquid phase can be cooled with a cooling device such as a condenser and recovered as a high-concentration furfural aqueous solution.

The aqueous solution containing sugars or the like recovered from the bottom of the concentration/separation device F (for example, a flash tank) is an aqueous solution containing sugars consisting of oligosaccharides or monosaccharides, which are water-soluble hydrolysates, or organic acids such as acetic acid (and inorganic acids such as sulfuric acid). The acetic acid, sulfuric acid, or the like contained in this aqueous solution is a substance which accelerates the hydrolysis reaction of the biomass, and pentoses and the like which produce furfural under the hydrolysis reaction conditions are also included in the sugars. Therefore, in order to use the solution as part of an aqueous liquid for preparing an aqueous suspension of the biomass raw material, it is possible to circulate the solution to the raw material suspension supply conduit 1 with the circulation conduit 8 illustrated in FIGS. 7, 9, 11, 12, and 24 and use the solution as a part of the aqueous liquid for preparing a suspension.

Figure 10:
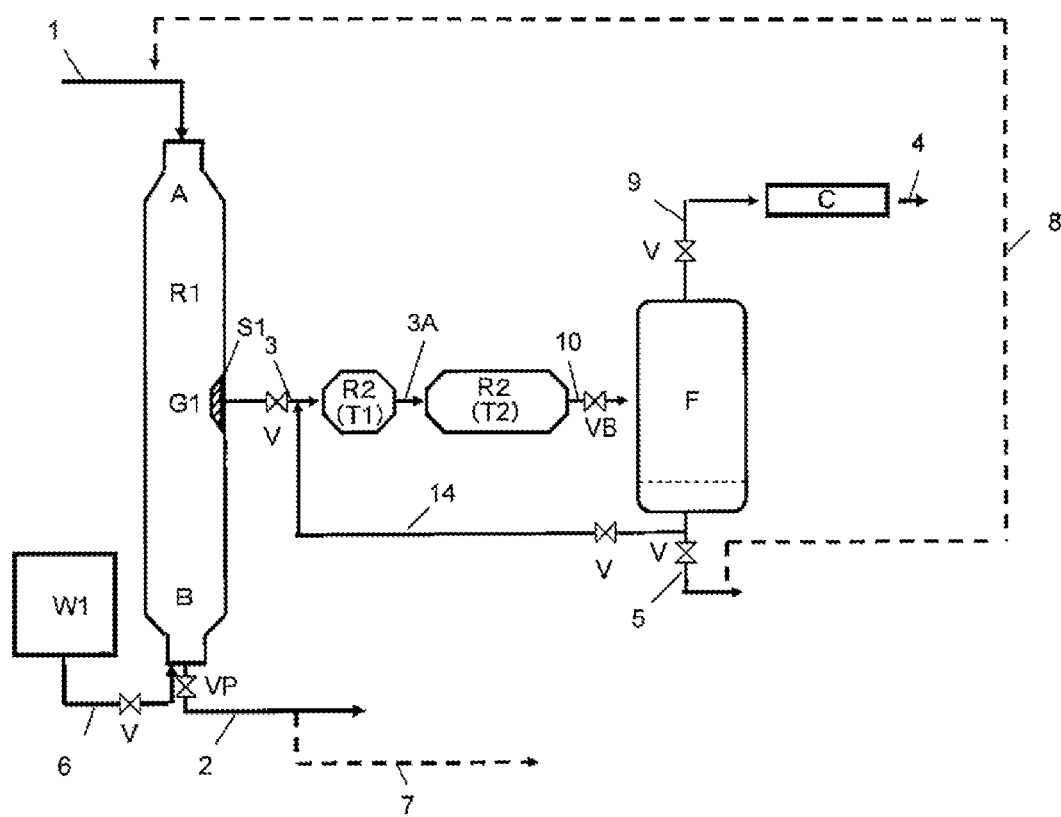
FIG. 10 illustrates an example of a device for implementing the method for continuously manufacturing monosaccharides, oligosaccharides, and/or furfurals from biomass according to the present invention.
Figure 11:
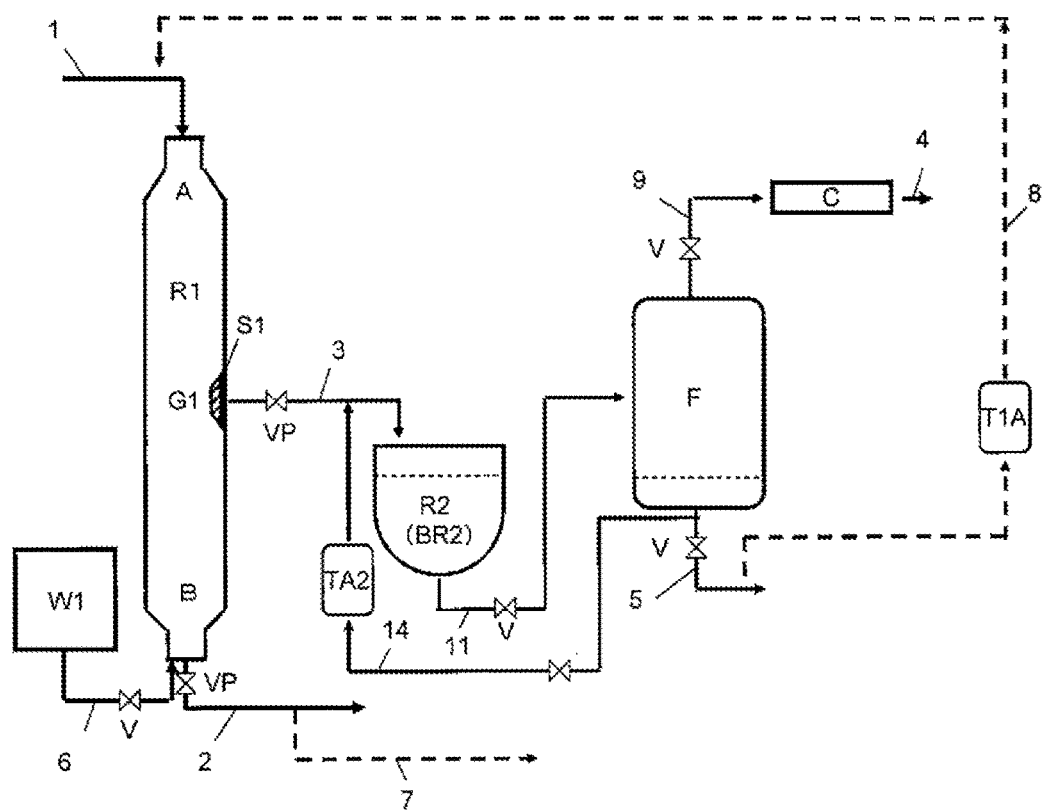
FIG. 11 illustrates another example of a device for implementing the method for continuously manufacturing monosaccharides, oligosaccharides, and/or furfurals from biomass according to the present invention.

As illustrated in FIG. 10 or 11, all or part of the aqueous solution containing sugars or the like recovered from the conduit 5 at the bottom of the concentration/separation device F is continuously supplied to the supply port (conduit 3) of the secondary hydrolysis device via a circulation conduit 14 for the aqueous solution containing sugars or the like, and the solution is subjected to secondary hydrolysis by the secondary hydrolysis device. In order to efficiently produce furfural, it is preferable to supply the entire volume of the aqueous solution containing sugars or the like recovered from the conduit 5 to the secondary hydrolysis device. The aqueous solution containing oligosaccharides and monosaccharides from which furfural has been removed by the flash tank is continuously circulated to the secondary hydrolysis device so that furfural is newly produced from the oligosaccharides and monosaccharides, which makes it possible to increase the production efficiently of furfural.

An aqueous solution storage tank TA2 for storing the aqueous solution containing sugars or the like recovered from the conduit 5 may also be installed on the circulation conduit 14. The aqueous liquid stored in the tank TA2 can be supplied to the supply port (conduit 3) of the secondary hydrolysis device as necessary.

When a plurality of secondary hydrolysis devices is installed in parallel, it is possible to install the conduit 14 independently for each of the secondary hydrolysis devices.

In order to efficiently produce furfural alone, it is preferable to set secondary hydrolysis conditions so that the conversion efficiency from xylose to furfural is high in secondary hydrolysis. In order to increase the conversion efficiency from xylose to furfural, it is preferable to set the temperature of secondary hydrolysis to 160 to 200° C. and to set the retention time of the primary hydrolysis solution supplied to the secondary hydrolysis device to 1 to 40 minutes. The production efficiency of furfural can be increased by performing secondary hydrolysis under conditions with a high conversion efficiency from xylose to furfural and circulating an aqueous solution (liquid phase) formed by removing the vapor phase from the resulting secondary hydrolysis solution with the concentration/separation device F to the secondary hydrolysis device.

The aqueous solution containing sugars or the like recovered from the bottom of the concentration/separation device F (for example, a flash tank) is an aqueous solution containing sugars consisting of oligosaccharides or monosaccharides, which are water-soluble hydrolysates, or organic acids such as acetic acid. The acetic acid contained in this aqueous solution is a substance which accelerates the hydrolysis reaction of the biomass, and pentoses and the like which produce furfural under the hydrolysis reaction conditions are also included in the sugars. Therefore, as illustrated in FIGS. 7 and 9, it is possible to circulate part of an aqueous liquid for preparing the aqueous suspension of the biomass raw material to the raw material suspension supply conduit 1 (aqueous liquid raw material supply conduit 1) with the circulation conduit 8 and use the solution as a part of the aqueous liquid for preparing a suspension. An aqueous solution storage tank TA1 for storing the aqueous liquid may also be installed on the circulation conduit 8. The aqueous liquid stored in the tank TA1 can be supplied to the raw material suspension supply conduit 1 as necessary.

When a plurality of secondary hydrolysis devices are installed in parallel, it is possible to install the conduit 8 independently for each of the secondary hydrolysis devices.

Figure 31:
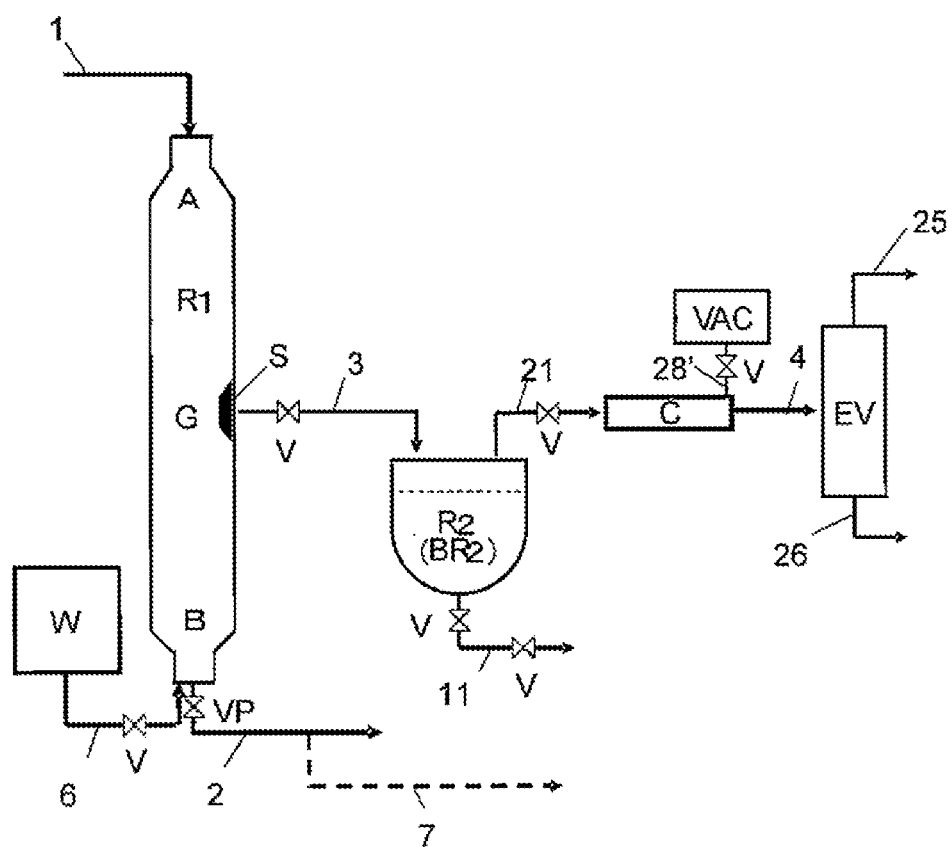
FIG. 31 illustrates an example for implementing the method for manufacturing monosaccharides, oligosaccharides, and/or furfurals from biomass according to the present invention.

As illustrated in FIG. 31, by decompressing the inside of the secondary hydrolysis device R2 using a decompression device VAC, it is possible to further recover furfurals remaining in the liquid phase after the vapor phase is removed by the secondary hydrolysis device. In addition, furfurals can also be recovered from the liquid phase by blowing air or vapor onto the liquid phase after the vapor phase is removed by the secondary hydrolysis device. The operation described above yields the merit that fractions containing furfurals and fractions containing sugars can be separated easily. In addition, furfurals can be recovered efficiently in a state with reduced energy cost.

(Oligosaccharide and Monosaccharide Separation Step)

The monosaccharides and oligosaccharides contained in the primary hydrolysis solution extracted from the primary hydrolysis device, the secondary hydrolysis solution, the aqueous solution after being separated by the concentration/separation device, or the aqueous solution (liquid phase) can be separated and purified with a method typically used in a sugar purification process. An evaporator or the like can be used as the concentration device for the sugar solution containing monosaccharides or oligosaccharides. In addition, the oligosaccharides may be concentrated or the oligosaccharides and monosaccharides may be separated using a UF membrane (ultrafiltration membrane), an RO membrane (reverse osmosis membrane), an NF membrane (nanofiltration), molecular sieve chromatography, simulated moving bed chromatography, or the like. Coloring components or impurities such as salts contained in the sugar solution can be removed using activated carbon, ion exchange resins (cation exchange resins, anion exchange resins, and the like), adsorption resins, or the like. The aqueous solution containing the purified monosaccharides can be purified by means of crystallization. In addition, the purified sugar solution can also be powderized using a spray dryer, a lyophilization device, or the like.

The primary hydrolysis solution, the secondary hydrolysis solution, or the aqueous solution (liquid phase) after being separated by the concentration/separation device can be concentrated by a concentration device prior to sugar purification. Furfurals or organic acids are contained in the primary hydrolysis solution and the secondary hydrolysis solution, and these components can be recovered as valuable resources from the evaporated fraction by means of a concentration step. In addition, since these components become a purification load when purifying sugars, it is possible to reduce the load in the sugar purification step by means of concentration. The sugar solution is preferably concentrated so that the concentration of the sugar solution is in the range of 5 to 60 mass % and more preferably in the range of 20 to 50 mass %.

When the primary hydrolysis solution, the secondary hydrolysis solution, or the aqueous solution (liquid phase), after being separated by the concentration/separation device, is acidic, the solution can be neutralized by adding an alkali. The alkali that is used may be calcium hydroxide, sodium hydroxide, potassium hydroxide, or the like. When the solution is treated using sulfuric acid in the secondary hydrolysis step, a neutralization method using calcium hydroxide, which can form insoluble salts, is preferable since there is the merit that the solution is easier to separate from the sugar solution (aqueous solution) than when a water-soluble salt such as sodium hydroxide is used. In this way, the load of the sugar purification step can be reduced by removing ions as insoluble salts.

Since the aqueous solution concentrated by the concentration device or the neutralized aqueous solution contains insoluble suspended matter, it is preferable to remove the insoluble suspended matter using a filtration/dewatering device. By removing insoluble suspended matter in advance, it is possible to reduce clogging inside the column in a subsequent sugar purification step (activated carbon, ion exchange resins, adsorption resins, or the like) and to stably maintain the flow rate of the aqueous solution passing into the column. Examples of devices that can be used as the filtration/dehydration device include vacuum filtration/dewatering devices such as an Oliver filter, a belt filter, a precoat filter, a disc filter, or a horizontal belt filter, a sealed pressure filtration device, a filter press device, a belt press device, a screw press device, a basket or decanter-type centrifugation filtration/dewatering device, a rotary pressure dewatering device, a multiple disc dehydration device, a hollow fiber membrane filtration device, and a cross-flow filtration device. In order to reduce the load in the subsequent purification step, a filtration device with which a filtrate having higher clarity can be obtained is preferable. It is preferable to use a precoat filter a disc filter, a hollow fiber membrane filtration device, or a cross-flow filtration device as such a filtration device, and it is more preferable to use a hollow fiber membrane filtration device or a cross-flow filtration device which requires a small installation area, uses no filter aids, and yields minimal waste such as cake after filtration. The pore size of the filtration aid or membrane that is used is preferably from 0.01 µm to 100 µm and more preferably from 0.1 to 10 µm. The types of filter aids that are used include diatomaceous earth, perlite, and mixtures thereof at any ratio. Examples of the materials of the membrane that is used include cellulose acetate, aromatic polyamide, polyvinyl alcohol, polysulfone, polyvinylidene fluoride, polyethylene, polyacrylonitrile, ceramic, polypropylene, polycarbonate, and polytetrafluoroethylene. Cellulose acetate, aromatic polyamide, and ceramic are preferable due to their high durability against washing chemicals, and even more preferable is ceramic having excellent physical stability.

Any activated carbon such as particulate coal or powdered coal can be used without any particular limitation as long as the substance has the ability to reduce the content of impurities such as colorants in the sugar solution. The average pore size of the activated carbon that is used is preferably from 0.1 to 5 nm and more preferably from 1.5 to 3 nm. In addition, the pore size distribution is preferably broad in the range of 0.1 to 100 nm. The colorants in the sugar solution can be removed efficiently by using an activated carbon having the pore size described above. Further, using a particulate activated carbon is preferable to using a powdered activated carbon from an operational standpoint in that it is easier to separate from the aqueous solution, which makes it easier to implement chemical regeneration or firing regeneration.

When an ion exchange resin is used, a cation exchange resin or an anion exchange resin may be used alone, or a cation exchange resin and an anion exchange resin may be linked in series and used. When a cation exchange resin and an anion exchange resin are linked in series, the order of the cation exchange resin and the anion exchange resin is not particularly limited. A cation exchange resin and an anion exchange resin may also be mixed together and used.

Examples of adsorption resins include phenol-formaldehyde resins (manufactured by Ajinomoto Fine Chemical Co., Ltd., trade names: "Hokuetsu HS" and "Hokuetsu KS") and styrene-divinylbenzene-based resins (manufactured by Mitsubishi Chemical Corporation, trade names: "Diaion HP20" and "Diaion HP21").

The activated carbon, ion exchange resin, or adsorption resin described above may be packed into a column or used in a batch mode. When packed into a column, the sugar solution may be passed through the column once or may be passed through the column multiple times repeatedly.

In the present invention, the monosaccharides and oligosaccharides in the hydrolysis solution treated by the continuous hydrolysis device or the aqueous solution (liquid phase) after being separated by the concentration/separation device can be purified using at least one type selected from activated carbon, ion exchange resins, and adsorption resins. When at least two activated carbons, ion exchange resins, or adsorption resins are used, the order thereof is not particularly limited, but in order to minimize the load of the ion exchange resin, it is preferable to perform treatment with an ion exchange resin after performing treatment with activated carbon or an adsorption resin.

The activated carbon, ion exchange resins, and adsorption resins described above may also be provided in parallel so as to purify the sugars simultaneously in parallel. When provided in parallel performing continuous treatment, washing and purification can be implemented simultaneously without stopping the continuous treatment, even if it becomes necessary to wash or replace the resin.

The hydrolysis solution treated by the continuous hydrolysis device may be supplied to the activated carbon, the ion exchange resin, or the adsorption resin after impurities are removed by a cross-flow filtration device, or the solution may be supplied to the activated carbon, the ion exchange resin, or the adsorption resin after being concentrated by a concentration device. However, it is preferable for the solution to be supplied to the activated carbon, the ion exchange resin, or the adsorption resin after being concentrated by a concentration device in that it becomes possible to miniaturize the activated carbon, ion exchange resin, or adsorption resin processing device.

By using the activated carbon, ion exchange resin, or adsorption resin described above, it is possible to efficiently remove impurities contained in the hydrolysis solution and to efficiently purify sugars (monosaccharides and oligosaccharides).

The separation of specific components from one another, such as the separation of glucose and xylose or the separation of galactose and xylose, may also be realized using molecular sieve chromatography, ion exchange chromatography, or a reverse osmosis membrane filtration device. When molecular sieve chromatography or ion exchange chromatography is used, it is preferable to use a simulated moving bed-type chromatographic separation device capable of continuous treatment. By crystallizing the purified sugar solution or the sugar solution at an intermediate stage of the purification step, it is also possible to obtain crystals of high-purity sugar.

The aqueous solution containing the purified monosaccharides may be concentrated to form liquid sugar or a syrup or may be powderized with a spray dryer. In addition, the purified sugar solution can also be powderized using a spray dryer, a freeze dehydration device, or the like.

In the present invention, the monosaccharides of the hydrolysis solution or the aqueous solution containing monosaccharides such as the sugar solution at an intermediate stage of the purification step or the purified sugar solution may be consumed using a fermenting microorganism (a microorganism containing a yeast such as *Saccharomyces cerevisiae*) so as to increase the content ratio of oligosaccharides. Similarly, it is also possible to increase the content ratio of pentoses by consuming hexoses alone from a mixture of pentoses and hexoses using the differences in the assimilation properties of sugar depending on the microorganism.

The xylose of the resulting aqueous solution containing xylose or the purified xylose can be converted to xylitol by a method such as hydrogenation. It is also possible to convert xylose to xylitol using a xylitol producing bacteria such as *Candida magnolia*.

EXAMPLES

Next, the present invention will be described in further detail using practical examples, but the present invention is not limited by these examples.

Production Example 1

Ion exchange water was mixed at a ratio of 5 kg per 1 kg (dry weight) of *Eucalyptus pellita* chips (2 mm thick), and the mixture was used as a raw material (raw material suspension). The raw material was continuously supplied from the raw material suspension supply conduit 1 connected to the top supply port A of the continuous primary hydrolysis device R1, illustrated in FIG. 1, at a rate of 400 parts by mass/hour. The solution was subjected to primary hydrolysis by the continuous primary hydrolysis device R1 at 150° C. and 0.48 MPa, and the hydrolyzed raw material was continuously discharged from the discharge port B of the continuous primary hydrolysis device R1. The time (retention time) from when the raw material was supplied from the supply port A of the continuous primary hydrolysis device R1 until the raw material was discharged from the discharge port B was set to 100 minutes.

Three hours after the supply of the raw material was begun (after a steady state was established), a hydrolysis solution (130 parts by mass/hour) was extracted from an intermediate extraction port G1 at a position corresponding to a hydrolysis time of 20 minutes of the continuous primary hydrolysis device R1 by opening the valve 1 in a state in which the temperature and pressure inside the continuous primary hydrolysis device R1 were maintained. The content of total sugar, monosaccharides, and furfural in the extracted hydrolysis solution was measured with the method describe below, and the yield of each component with respect to the raw material (dry weight) was calculated from the quantitative values in the solution. The results are shown in Table 1.

<Sugar Analysis>

Sugar analysis was performed using a sugar analysis system (ICS5000) manufactured by DIONEX. Using a CArBopAk PA-1 (20×250 mm) as a column and a 20 mM NaOH solution as an eluant, monosaccharides were eluted at a flow rate of 0.25 ml/min. A pulsed amperometric detector was used for detection. Glucose, galactose, mannose, arabinose, and xylose were used as a standard monosaccharide preparation. A calibration curve was created for each of these components, and the content of each monosaccharide in the sample was determined.

<Analysis of Total Sugar Amount>

Sulfuric acid was added to the sample solution so that the final concentration was 4 mass %. After hydrolysis was performed for one hour at 120° C., sugar analysis was performed to find the content of each monosaccharide in the sample, and the total value was used as the total amount of sugar.

<Calculation of Oligosaccharide Content>

A value determined by subtracting the content of each monosaccharide in the sample prior to hydrolysis with 4 mass % sulfuric acid from the total amount of sugar in the sample was used as the oligosaccharide content.

<Quantitative Determination of Furfurals>

An HPLC manufactured by Agilent was used for the quantitative determination of furfurals. Using an Aminex HPX87P (7.8×300 mm) manufactured by Bio-Rad as a column and a 5 mM sulfuric acid solution as an eluant, furfurals were eluted at a flow rate of 1 ml/min. A UV-Vis detector was used for detection. Furfural was used as a standard furfural preparation, and a calibration curve was created to determine the content in the sample.

Production Example 2

Hydrolysis was performed with the same method as that of Production Example 1 with the exception of extracting a hydrolysis solution from an intermediate extraction port at a position corresponding to a hydrolysis time of 30 minutes in Production Example 1. The results are shown in Table 1.

Production Example 3

Hydrolysis was performed with the same method as in Production Example 1 with the exception of extracting a hydrolysis solution from an intermediate extraction port at a position corresponding to a hydrolysis time of 40 minutes in Production Example 1. The results are shown in Table 1.

Production Example 4

Hydrolysis was performed with the same method as in Production Example 1 with the exception of extracting a hydrolysis solution from an intermediate extraction port at a position corresponding to a hydrolysis time of 50 minutes in Production Example 1. The results are shown in Table 1.

Production Example 5

Hydrolysis was performed with the same method as in Production Example 1 with the exception of extracting a hydrolysis solution from an intermediate extraction port at a position corresponding to a hydrolysis time of 60 minutes in Production Example 1. The results are shown in Table 1.

Production Example 6

Hydrolysis was performed with the same method as in Production Example 1 with the exception of extracting a hydrolysis solution from an intermediate extraction port at a position corresponding to a hydrolysis time of 70 minutes in Production Example 1. The results are shown in Table 1.

Production Example 7

Hydrolysis was performed with the same method as in Production Example 1 with the exception of extracting a hydrolysis solution from an intermediate extraction port at a position corresponding to a hydrolysis time of 80 minutes in Production Example 1. The results are shown in Table 1.

TABLE 1

|  |  | Yield (%: relative to raw material) |
|---|---|---|
| (Production Example 1) 150° C. Extraction of the hydrolysis solution from a position corresponding to a raw material treatment time of 20 minutes | Total sugar Monosaccharides Oligosaccharides Furfurals | 4.8 1.2 3.6 0.2 |
| Production Example 2 150° C. Extraction of the hydrolysis solution from a position corresponding to a raw material treatment time of 30 minutes | Total sugar Monosaccharides Oligosaccharides Furfurals | 6.3 2.2 4.1 0.3 |
| Production Example 3 150° C. Extraction of the hydrolysis solution from a position corresponding to a raw material treatment time of 40 minutes | Total sugar Monosaccharides Oligosaccharides Furfurals | 7.3 3.0 4.3 0.4 |
| Production Example 4 150° C. Extraction of the hydrolysis solution from a position corresponding to a raw material treatment time of 50 minutes | Total sugar Monosaccharides Oligosaccharides Furfurals | 7.9 3.4 4.5 0.9 |
| Production Example 5 150° C. Extraction of the hydrolysis solution from a position corresponding to a raw material treatment time of 60 minutes | Total sugar Monosaccharides Oligosaccharides Furfurals | 9.8 4.8 5.0 1.2 |
| Production Example 6 150° C. Extraction of the hydrolysis solution from a position corresponding to a raw material treatment time of 70 minutes | Total sugar Monosaccharides Oligosaccharides Furfurals | 10.8 6.5 4.3 2.5 |
| Production Example 7 150° C. Extraction of the hydrolysis solution from a position corresponding to a raw material treatment time of 80 minutes | Total sugar Monosaccharides Oligosaccharides Furfurals | 7.5 6.3 1.2 2.7 |

As illustrated in Table 1, in the production examples in which continuous primary hydrolysis was performed at 150° C., hydrolysis solutions with differing production ratios of monosaccharides, oligosaccharides, and furfurals and differing production volumes of each of the components were obtained by changing the position of the intermediate extraction port of the continuous primary hydrolysis device.

The yield of monosaccharides was highest in the hydrolysis solution extracted from the intermediate extraction port at the 70-minute position (Production Example 6). The yield of oligosaccharides was highest in the hydrolysis solution extracted from the intermediate extraction port at the 60-minute position (Production Example 5). The yield of furfurals was highest in the hydrolysis solution extracted from the intermediate extraction port at the 80-minute position (Production Example 7).

In addition, the ratios of sugars (monosaccharides+oligosaccharides) with respect to furfurals were high in the hydrolysis solutions extracted from the intermediate extraction ports at the 20-minute position (Production Example 1), the 30-minute position (Production Example 2), and the 40-minute position (Production Example 3).

Production Example 8

Hydrolysis was performed with the same method as in Production Example 1 with the exception of performing hydrolysis at 170° C. and 0.80 MPa using the continuous primary hydrolysis device R1 in Production Example 1. A hydrolysis solution was extracted from an intermediate extraction port at a position corresponding to a hydrolysis time of 20 minutes. The results are shown in Table 2 and FIG. 2.

Production Example 9

Hydrolysis was performed with the same method as in Production Example 1 with the exception of performing hydrolysis at 170° C. and 0.80 MPa using the continuous primary hydrolysis device R1. A hydrolysis solution was extracted from an intermediate extraction port at a position corresponding to a hydrolysis time of 30 minutes. The results are shown in Table 2 and FIG. 2.

Production Example 10

Hydrolysis was performed with the same method as in Production Example 1 with the exception of performing hydrolysis at 170° C. and 0.80 MPa using the continuous primary hydrolysis device R1. A hydrolysis solution was extracted from an intermediate extraction port at a position corresponding to a hydrolysis time of 40 minutes. The results are shown in Table 2 and FIG. 2.

Production Example 11

Hydrolysis was performed with the same method as in Production Example 1 with the exception of performing hydrolysis at 170° C. and 0.80 MPa using the continuous primary hydrolysis device R1. A hydrolysis solution was extracted from an intermediate extraction port at a position corresponding to a hydrolysis time of 50 minutes. The results are shown in Table 2 and FIG. 2.

Production Example 12

Hydrolysis was performed with the same method as in Production Example 1 with the exception of performing hydrolysis at 170° C. and 0.80 MPa using the continuous primary hydrolysis device R1. A hydrolysis solution was extracted from an intermediate extraction port at a position corresponding to a hydrolysis time of 60 minutes. The results are shown in Table 2 and FIG. 2.

Production Example 13

Hydrolysis was performed with the same method as in Production Example 1 with the exception of performing hydrolysis at 170° C. and 0.80 MPa using the continuous primary hydrolysis device R1. A hydrolysis solution was extracted from an intermediate extraction port at a position corresponding to a hydrolysis time of 70 minutes. The results are shown in Table 2 and FIG. 2.

Production Example 14

Hydrolysis was performed with the same method as in Production Example 1 with the exception of performing hydrolysis at 170° C. and 0.80 MPa using the continuous primary hydrolysis device R1. A hydrolysis solution was extracted from an intermediate extraction port at a position corresponding to a hydrolysis time of 80 minutes. The results are shown in Table 2 and FIG. 2.

TABLE 2

|  |  | Yield (%: relative to raw material) |
|---|---|---|
| Production Example 8 170° C. | Total sugar Monosaccharides | 2.9 1.4 |

TABLE 2-continued

| | | Yield (%: relative to raw material) |
|---|---|---|
| Extraction of the hydrolysis solution from a position corresponding to a raw material treatment time of 20 minutes | Oligosaccharides<br>Furfurals | 1.5<br>0.5 |
| Production Example 9<br>170° C.<br>Extraction of the hydrolysis solution from a position corresponding to a raw material treatment time of 30 minutes | Total sugar<br>Monosaccharides<br>Oligosaccharides<br>Furfurals | 5.4<br>2.8<br>2.6<br>0.5 |
| Production Example 10<br>170° C.<br>Extraction of the hydrolysis solution from a position corresponding to a raw material treatment time of 40 minutes | Total sugar<br>Monosaccharides<br>Oligosaccharides<br>Furfurals | 7.6<br>3.1<br>4.5<br>0.8 |
| Production Example 11<br>170° C.<br>Extraction of the hydrolysis solution from a position corresponding to a raw material treatment time of 50 minutes | Total sugar<br>Monosaccharides<br>Oligosaccharides<br>Furfurals | 7.2<br>3.7<br>3.5<br>1.5 |
| Production Example 12<br>170° C.<br>Extraction of the hydrolysis solution from a position corresponding to a raw material treatment time of 60 minutes | Total sugar<br>Monosaccharides<br>Oligosaccharides<br>Furfurals | 8.7<br>6.1<br>2.6<br>2.1 |
| Production Example 13<br>170° C.<br>Extraction of the hydrolysis solution from a position corresponding to a raw material treatment time of 70 minutes | Total sugar<br>Monosaccharides<br>Oligosaccharides<br>Furfurals | 6.7<br>5.8<br>0.9<br>3.4 |
| Production Example 14<br>170° C.<br>Extraction of the hydrolysis solution from a position corresponding to a raw material treatment time of 80 minutes | Total sugar<br>Monosaccharides<br>Oligosaccharides<br>Furfurals | 6.0<br>5.4<br>0.6<br>2.8 |

Figure 2:
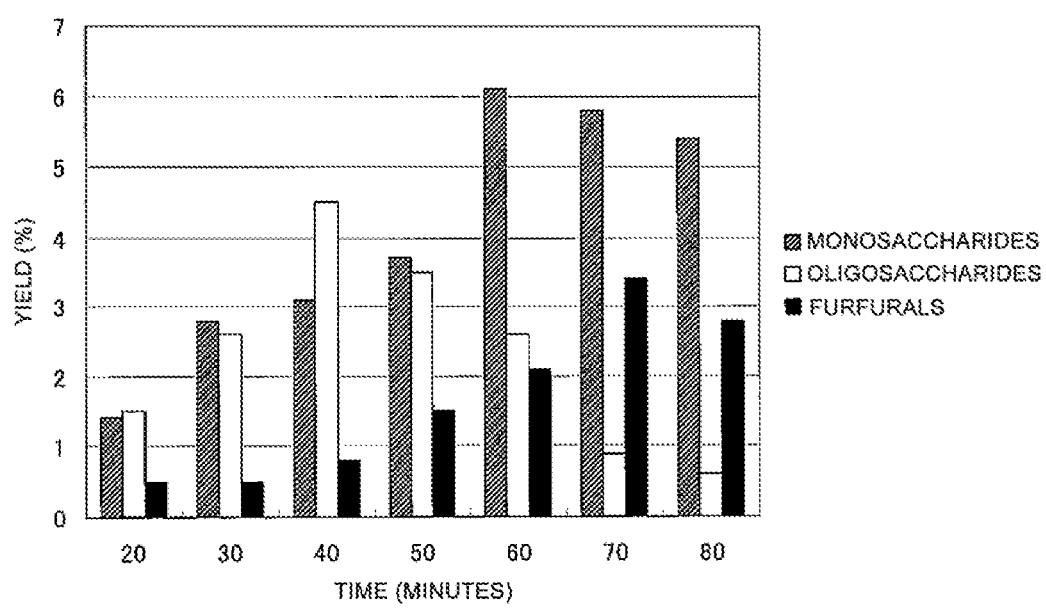
FIG. 2 illustrates changes in the yield of monosaccharides, oligosaccharides, and/or furfurals over time due to continuous primary hydrolysis.

As illustrated in Table 2 and FIG. 2, in the tests in which continuous primary hydrolysis was performed at 170° C., hydrolysis solutions with differing production ratios of monosaccharides, oligosaccharides, and furfurals and differing production volumes of each of the components were obtained by changing the position of the intermediate extraction port of the continuous primary hydrolysis device R1.

The yield of monosaccharides was highest in the hydrolysis solution extracted from the intermediate extraction port at the 60-minute position (Production Example 12). The yield of oligosaccharides was highest in the hydrolysis solution extracted from the intermediate extraction port at the 40-minute position (Production Example 10). The yield of furfurals was highest in the hydrolysis solution extracted from the intermediate extraction port at the 70-minute position (Production Example 13).

Production Example 15

Hydrolysis was performed with the same method as in Production Example 1 with the exception of performing hydrolysis at 190° C. and 1.26 MPa using the continuous primary hydrolysis device R1 in Production Example 1. A hydrolysis solution was extracted from an intermediate extraction port at a position corresponding to a hydrolysis time of 20 minutes. The results are shown in Table 3.

Production Example 16

Hydrolysis was performed with the same method as in Production Example 1 with the exception of performing hydrolysis at 190° C. and 1.26 MPa using the continuous primary hydrolysis device R1 in Production Example 1. A hydrolysis solution was extracted from an intermediate extraction port at a position corresponding to a hydrolysis time of 30 minutes. The results are shown in Table 3.

Production Example 17

Hydrolysis was performed with the same method as in Production Example 1 with the exception of performing hydrolysis at 190° C. and 1.26 MPa using the continuous primary hydrolysis device R1 in Production Example 1. A hydrolysis solution was extracted from an intermediate extraction port at a position corresponding to a hydrolysis time of 40 minutes. The results are shown in Table 3.

Production Example 18

Hydrolysis was performed with the same method as in Production Example 1 with the exception of performing hydrolysis at 190° C. and 1.26 MPa using the continuous primary hydrolysis device R1 in Production Example 1. A hydrolysis solution was extracted from an intermediate extraction port at a position corresponding to a hydrolysis time of 50 minutes. The results are shown in Table 3.

Production Example 19

Hydrolysis was performed with the same method as in Production Example 1 with the exception of performing hydrolysis at 190° C. and 1.26 MPa using the continuous primary hydrolysis device R1 in Production Example 1. A hydrolysis solution was extracted from an intermediate extraction port at a position corresponding to a hydrolysis time of 60 minutes. The results are shown in Table 3.

Production Example 20

Hydrolysis was performed with the same method as in Production Example 1 with the exception of performing hydrolysis at 190° C. and 1.26 MPa using the continuous primary hydrolysis device R1 in Production Example 1. A hydrolysis solution was extracted from an intermediate extraction port at a position corresponding to a hydrolysis time of 70 minutes. The results are shown in Table 3.

Production Example 21

Hydrolysis was performed with the same method as in Production Example 1 with the exception of performing hydrolysis at 190° C. and 1.26 MPa using the continuous primary hydrolysis device R1 in Production Example 1. A hydrolysis solution was extracted from an intermediate extraction port at a position corresponding to a hydrolysis time of 80 minutes. The results are shown in Table 3.

TABLE 3

| | | Yield (%: relative to raw material) |
|---|---|---|
| Production Example 15<br>190° C.<br>Extraction of the hydrolysis solution from a position corresponding to a raw material treatment time of 20 minutes | Total sugar<br>Monosaccharides<br>Oligosaccharides<br>Furfurals | 5.3<br>2.1<br>3.2<br>0.4 |
| Production Example 16<br>190° C.<br>Extraction of the hydrolysis solution from a position corresponding to a raw material treatment time of 30 minutes | Total sugar<br>Monosaccharides<br>Oligosaccharides<br>Furfurals | 7.6<br>3.0<br>4.6<br>0.4 |

TABLE 3-continued

| | | Yield (%: relative to raw material) |
|---|---|---|
| Production Example 17<br>190° C.<br>Extraction of the hydrolysis solution from a position corresponding to a raw material treatment time of 40 minutes | Total sugar<br>Monosaccharides<br>Oligosaccharides<br>Furfurals | 8.9<br>4.9<br>4.0<br>1.5 |
| Production Example 18<br>190° C.<br>Extraction of the hydrolysis solution from a position corresponding to a raw material treatment time of 50 minutes | Total sugar<br>Monosaccharides<br>Oligosaccharides<br>Furfurals | 9.9<br>6.4<br>3.5<br>2.7 |
| Production Example 19<br>190° C.<br>Extraction of the hydrolysis solution from a position corresponding to a raw material treatment time of 60 minutes | Total sugar<br>Monosaccharides<br>Oligosaccharides<br>Furfurals | 8.0<br>5.3<br>2.7<br>3.5 |
| Production Example 20<br>190° C.<br>Extraction of the hydrolysis solution from a position corresponding to a raw material treatment time of 70 minutes | Total sugar<br>Monosaccharides<br>Oligosaccharides<br>Furfurals | 5.2<br>4.5<br>0.7<br>2.9 |
| Production Example 21<br>190° C.<br>Extraction of the hydrolysis solution from a position corresponding to a raw material treatment time of 80 minutes | Total sugar<br>Monosaccharides<br>Oligosaccharides<br>Furfurals | 4.1<br>3.7<br>0.4<br>2.0 |

As illustrated in Table 3, in the tests in which continuous primary hydrolysis was performed at 190° C. as well, hydrolysis solutions with differing production ratios of monosaccharides, oligosaccharides, and furfurals and differing production volumes of each of the components were obtained by changing the position of the intermediate extraction port of the continuous primary hydrolysis device.

The yield of monosaccharides was highest in the hydrolysis solution extracted from the intermediate extraction port at the 50-minute position (Production Example 18). The yield of oligosaccharides was highest in the hydrolysis solution extracted from the intermediate extraction port at the 30-minute position (Production Example 16). The yield of furfurals was highest in the hydrolysis solution extracted from the intermediate extraction port at the 60-minute position (Production Example 19).

It was ascertained from the results of the aforementioned Production Examples 1 to 21 (Tables 1 to 3) that at 150 to 190° C., it is possible to control the production ratios and production volumes of oligosaccharides, monosaccharides, and furfurals in accordance with the intended purpose by changing the position of the intermediate extraction port of the continuous primary hydrolysis device R1.

Production Example 22

In the continuous primary hydrolysis device R1 illustrated in FIG. 1, continuous hydrolysis was performed with the same method as in Production Example 8 (hydrolysis temperature: 170° C.) with the exception of supplying washing water at a rate of 400 parts by mass/hour from a washing solution supply device W1 at the bottom of the device via a washing water supply conduit 6 and bringing the solution into contact, in a countercurrent manner, with a hydrolysis suspension moving downward from the intermediate extraction port G1 of the continuous primary hydrolysis device R1 provided with a stainless steel metal mesh having an opening size of 80 μm (solid-liquid separation device S1).

Three hours after the supply of the raw material was begun (after a steady state was established), a hydrolysis solution (130 parts by mass/hour) was extracted from an intermediate extraction port at a position corresponding to a hydrolysis time of 20 minutes of the hydrolysis device by opening the valve 1 in a state in which the temperature and pressure inside the hydrolysis device were maintained. The content of total sugar, monosaccharides, and furfural in the extracted hydrolysis solution was measured, and the yield of each component with respect to the raw material (dry weight) was calculated from the quantitative values in the solution. The results are shown in Table 4.

Production Example 23

Continuous hydrolysis was performed with the same method as that of Production Example 22 with the exception of extracting a hydrolysis solution from an intermediate extraction port at a position corresponding to a hydrolysis time of 30 minutes in Production Example 22. The results are shown in Table 4.

Production Example 24

Continuous hydrolysis was performed with the same method as that of Production Example 22 with the exception of extracting a hydrolysis solution from an intermediate extraction port at a position corresponding to a hydrolysis time of 40 minutes in Production Example 22. The results are shown in Table 4.

The results are shown in Table 4.

Production Example 25

Continuous hydrolysis was performed with the same method as that of Production Example 22 with the exception of extracting a hydrolysis solution from an intermediate extraction port at a position corresponding to a hydrolysis time of 50 minutes in Production Example 22. The results are shown in Table 4.

Production Example 26

Continuous hydrolysis was performed with the same method as that of Production Example 22 with the exception of extracting a hydrolysis solution from an intermediate extraction port at a position corresponding to a hydrolysis time of 60 minutes in Production Example 22. The results are shown in Table 4.

Production Example 27

Continuous hydrolysis was performed with the same method as that of Production Example 22 with the exception of extracting a hydrolysis solution from an intermediate extraction port at a position corresponding to a hydrolysis time of 70 minutes in Production Example 22. The results are shown in Table 4.

Production Example 28

Continuous hydrolysis was performed with the same method as that of Production Example 22 with the exception of extracting a hydrolysis solution from an intermediate extraction port at a position corresponding to a hydrolysis time of 80 minutes in Production Example 22. The results are shown in Table 4.

TABLE 4

| | | Yield (%: relative to raw material) |
|---|---|---|
| Production Example 22 | Total sugar | 3.3 |
| 170° C. | Monosaccharides | 1.6 |
| Extraction of the hydrolysis solution from a | Oligosaccharides | 1.7 |
| position corresponding to a raw material | Furfurals | 0.4 |
| treatment time of 20 minutes | | |
| Production Example 23 | Total sugar | 5.8 |
| 170° C. | Monosaccharides | 3.0 |
| Extraction of the hydrolysis solution from a | Oligosaccharides | 2.8 |
| position corresponding to a raw material | Furfurals | 0.5 |
| treatment time of 30 minutes | | |
| Production Example 24 | Total sugar | 8.1 |
| 170° C. | Monosaccharides | 3.4 |
| Extraction of the hydrolysis solution from a | Oligosaccharides | 4.7 |
| position corresponding to a raw material | Furfurals | 0.7 |
| treatment time of 40 minutes | | |
| Production Example 25 | Total sugar | 7.7 |
| 170° C. | Monosaccharides | 3.9 |
| Extraction of the hydrolysis solution from a | Oligosaccharides | 3.8 |
| position corresponding to a raw material | Furfurals | 2.5 |
| treatment time of 50 minutes | | |
| Production Example 26 | Total sugar | 9.2 |
| 170° C. | Monosaccharides | 6.4 |
| Extraction of the hydrolysis solution from a | Oligosaccharides | 2.8 |
| position corresponding to a raw material | Furfurals | 1.5 |
| treatment time of 60 minutes | | |
| Production Example 27 | Total sugar | 7.2 |
| 170° C. | Monosaccharides | 6.1 |
| Extraction of the hydrolysis solution from a | Oligosaccharides | 1.1 |
| position corresponding to a raw material | Furfurals | 3.0 |
| treatment time of 70 minutes | | |
| Production Example 28 | Total sugar | 6.5 |
| 170° C. | Monosaccharides | 5.7 |
| Extraction of the hydrolysis solution from a | Oligosaccharides | 0.8 |
| position corresponding to a raw material | Furfurals | 3.1 |
| treatment time of 80 minutes | | |

With the systems in which a washing solution was supplied to the continuous primary hydrolysis device illustrated in FIG. 1 (Production Examples 22 to 28), the yield of monosaccharides, oligosaccharides, and furfurals contained in the hydrolysis solution after secondary hydrolysis improved in comparison to the systems in which the washing solution of FIG. 1 was not supplied (Production Examples 8 to 14).

Production Example 29

Continuous hydrolysis was performed with the same method as in Production Example 8 with the exception of performing continuous primary hydrolysis (170° C.) using cedar (2 mm thick) as a raw material and extracting a hydrolysis solution from an intermediate extraction port at a position corresponding to a hydrolysis time of 20 minutes in Production Example 8. The results are shown in Table 5.

Production Example 30

Continuous hydrolysis was performed with the same method as in Production Example 9 with the exception of performing continuous primary hydrolysis (170° C.) using cedar (2 mm thick) as a raw material and extracting a hydrolysis solution from an intermediate extraction port at a position corresponding to a hydrolysis time of 30 minutes in Production Example 9. The results are shown in Table 5.

Production Example 31

Continuous hydrolysis was performed with the same method as in Production Example 10 with the exception of performing continuous primary hydrolysis (170° C.) using cedar (2 mm thick) as a raw material and extracting a hydrolysis solution from an intermediate extraction port at a position corresponding to a hydrolysis time of 40 minutes in Production Example 10. The results are shown in Table 5.

Production Example 32

Hydrolysis was performed with the same method as in Production Example 11 with the exception of performing continuous primary hydrolysis (170° C.) using cedar (2 mm thick) as a raw material and extracting a hydrolysis solution from an intermediate extraction port at a position corresponding to a hydrolysis time of 50 minutes in Production Example 11. The results are shown in Table 5.

Production Example 33

Hydrolysis was performed with the same method as in Production Example 12 with the exception of performing continuous primary hydrolysis (170° C.) using cedar (2 mm thick) as a raw material and extracting a hydrolysis solution from an intermediate extraction port at a position corresponding to a hydrolysis time of 60 minutes in Production Example 12. The results are shown in Table 5.

Production Example 34

Hydrolysis was performed with the same method as in Production Example 13 with the exception of performing continuous primary hydrolysis (170° C.) using cedar (2 mm thick) as a raw material and extracting a hydrolysis solution from an intermediate extraction port at a position corresponding to a hydrolysis time of 70 minutes in Production Example 13. The results are shown in Table 5.

Production Example 35

Hydrolysis was performed with the same method as in Production Example 14 with the exception of performing continuous primary hydrolysis (170° C.) using cedar (2 mm thick) as a raw material and extracting a hydrolysis solution from an intermediate extraction port at a position corresponding to a hydrolysis time of 80 minutes in Production Example 14. The results are shown in Table 5.

TABLE 5

| | | Yield (%: relative to raw material) |
|---|---|---|
| Production Example 29 | Total sugar | 2.4 |
| 170° C. | Monosaccharides | 1.1 |
| Extraction of the hydrolysis solution from a | Oligosaccharides | 1.3 |
| position corresponding to a raw material | Furfurals | 0.3 |
| treatment time of 20 minutes | | |
| Production Example 30 | Total sugar | 4.7 |
| 170° C. | Monosaccharides | 2.4 |
| Extraction of the hydrolysis solution from a | Oligosaccharides | 2.3 |
| position corresponding to a raw material | Furfurals | 0.4 |
| treatment time of 30 minutes | | |
| Production Example 31 | Total sugar | 6.5 |
| 170° C. | Monosaccharides | 2.7 |
| Extraction of the hydrolysis solution from a | Oligosaccharides | 3.8 |
| position corresponding to a raw material | Furfurals | 0.7 |
| treatment time of 40 minutes | | |
| Production Example 32 | Total sugar | 6.5 |
| 170° C. | Monosaccharides | 3.1 |
| Extraction of the hydrolysis solution from a | Oligosaccharides | 3.4 |
| position corresponding to a raw material | Furfurals | 1.7 |
| treatment time of 50 minutes | | |

TABLE 5-continued

|  | Yield (%: relative to raw material) |  |
|---|---|---|
| Production Example 33<br>170° C.<br>Extraction of the hydrolysis solution from a position corresponding to a raw material treatment time of 60 minutes | Total sugar<br>Monosaccharides<br>Oligosaccharides<br>Furfurals | 8.5<br>5.7<br>2.8<br>2.5 |
| Production Example 34<br>170° C.<br>Extraction of the hydrolysis solution from a position corresponding to a raw material treatment time of 70 minutes | Total sugar<br>Monosaccharides<br>Oligosaccharides<br>Furfurals | 6.9<br>5.5<br>1.4<br>3.1 |
| Production Example 35<br>170° C.<br>Extraction of the hydrolysis solution from a position corresponding to a raw material treatment time of 80 minutes | Total sugar<br>Monosaccharides<br>Oligosaccharides<br>Furfurals | 6.1<br>5.0<br>1.1<br>2.2 |

As illustrated in Table 5, in the tests in which cedar was used as a raw material (continuous hydrolysis at 170° C.) as well, hydrolysis solutions with differing production ratios of monosaccharides, oligosaccharides, and furfurals and differing production volumes of each of the components were obtained by changing the position of the intermediate extraction port of the continuous primary hydrolysis device.

The yield of monosaccharides was highest in the hydrolysis solution extracted from the intermediate extraction port at the 60-minute position (Production Example 33). The yield of oligosaccharides was highest in the hydrolysis solution extracted from the intermediate extraction port at the 40-minute position (Production Example 31). The yield of furfurals was highest in the hydrolysis solution extracted from the intermediate extraction port at the 70-minute position (Production Example 34).

It was confirmed from the above results that in tests using eucalyptus and cedar, it is possible to control the production ratios and production volumes of monosaccharides, oligosaccharides, and furfurals in accordance with the intended purpose by changing the position of the intermediate extraction port of the continuous primary hydrolysis device.

Production Example 36

A raw material suspension containing a raw material biomass was prepared by mixing *Eucalyptus pellita* chips (2 mm thick) and ion exchange water at a ratio of 5 parts by mass of ion exchange water per 1 part by mass of the chips (dry).

The raw material suspension was continuously supplied from the raw material suspension supply conduit 1 connected to the top supply port A of the continuous primary hydrolysis device R1 illustrated in FIG. 3 at a rate of 300 parts by mass/hour. The solution was hydrolyzed in the hydrolysis device at 165° C. and 0.70 MPa, and the hydrolyzed hydrolysis suspension was discharged to the discharge conduit 2 from the bottom discharge port B of the hydrolysis device by opening the decompression valve VP. The retention time in the hydrolysis device was set to 100 minutes.

On the other hand, washing water was supplied from the washing solution supply device W1 to the bottom of the primary hydrolysis device at a rate of 100 parts by mass/hour by opening the valve V4 of the washing solution supply conduit 6, and the solution was brought into contact, in a countercurrent manner, with a hydrolysis suspension moving downward through intermediate extraction ports G1 and G2 at two locations in the center of the primary hydrolysis device R1 provided with a stainless steel metal mesh having an opening size of 300 μm.

Three hours after the supply of the raw material was begun (after steady state operation was begun), a hydrolysis solution (100 parts by mass/hour) was extracted from the intermediate extraction port G1 on the upper side of the hydrolysis state (at a position corresponding to a hydrolysis time of 40 minutes) by opening the valve V1 of the hydrolysis solution extraction conduit 3 in a state in which the temperature and pressure inside the hydrolysis device were maintained, and the hydrolysis solution (100 parts by mass/hour) was extracted from the intermediate extraction port G2 for the hydrolysis solution at the lower part of the hydrolysis device (at a position corresponding to a hydrolysis time of 60 minutes) by opening the valve V2 of the hydrolysis solution extraction conduit 4. Warm water at 95° C. (100 parts by mass/hour) was extracted from the aqueous liquid supply device W2 by opening the valve V3 of an aqueous liquid supply conduit 19 at the same time that the extraction of the hydrolysis solution was begun, and the solution was supplied to the primary hydrolysis device from an aqueous liquid supply port E between the intermediate extraction ports G1 and G2 for the hydrolysis solution.

The content of the monosaccharides, oligosaccharides, and furfurals contained in the hydrolysis solution 1 extracted from the hydrolysis solution extraction conduit 3 and the hydrolysis solution 2 extracted from the hydrolysis solution extraction conduit 4 was measured with the same method as in Production Example 1, and the yield of each component with respect to the raw material (dry mass) was calculated. The results are shown in Table 6.

Production Example 37

Hydrolysis was performed with the same method as in Production Example 36 with the exception of closing the valve V1 of the hydrolysis solution extraction conduit 3 so that the hydrolysis solution 1 is not extracted and closing the valve V3 of the aqueous liquid supply conduit so as to stop the supply of warm water in Production Example 36. The results are shown in Table 6.

TABLE 6

|  | Yield (%: relative to raw material) | | | | |
|---|---|---|---|---|---|
|  | Hydrolysis solution 1 | | Hydrolysis solution 2 | | Total |
| Production Example 36 | Monosaccharides<br>Oligosaccharides<br>Furfurals | 3.1<br>4.50<br>0.81 | Monosaccharides<br>Oligosaccharides<br>Furfurals | 1.78<br>2.36<br>0.46 | 4.88<br>6.86<br>1.27 |
| Production Example 37 | Monosaccharides<br>Oligosaccharides<br>Furfurals | —<br>—<br>— | Monosaccharides<br>Oligosaccharides<br>Furfurals | 1.87<br>2.82<br>1.02 | 1.87<br>2.82<br>1.02 |

As shown in Table 6, when the hydrolysis solution was extracted from the intermediate extraction ports G1 and G2 (upper and lower) at two locations of the hydrolysis device (Production Examples 36), the yield of monosaccharides, oligosaccharides, and furfurals was higher than when the hydrolysis solution was extracted from only the intermediate extraction port G2 (lower) at one location of the hydrolysis device (Production Example 37).

It can be inferred from the above results that the yield of monosaccharides, oligosaccharides, and furfurals improved as a result of the monosaccharides, oligosaccharides, and furfurals becoming more soluble in the aqueous solution from the raw material in the hydrolysis device after extracting the hydrolysis solution from intermediate extraction ports at two or more locations of the hydrolysis device and simultaneously supplying an aqueous liquid (warm water) at the same volume as the extracted volume.

Production Example 38

Hydrolysis was performed with the device illustrated in FIG. 4. The hydrolysis conditions in the primary hydrolysis device were the same as those in Production Example 36. However, in Production Example 38, not only were the hydrolysis solutions 1 and 2 extracted, but a hydrolysis solution 3 (250 parts by mass/hour) was also extracted by a strainer with an opening size of 300 μm installed on the discharge conduit 2 from the hydrolysis suspension discharged to the discharge conduit 2 from the bottom discharge port B, and the solution was recovered via the extraction conduit 20 by opening the valve V5. The content of the monosaccharides, oligosaccharides, and furfurals contained in the hydrolysis solutions 1 to 3 extracted from the extraction conduits 3, 4, and 20 was measured with the same method as in Production Example 36, and the yield of each component with respect to the raw material (dry mass) was calculated. The results are shown in Table 7.

TABLE 7

| | Yield (%: relative to raw material) | | | | | | |
|---|---|---|---|---|---|---|---|
| | Hydrolysis solution 1 | | Hydrolysis solution 2 | | Hydrolysis solution 3 | | Total |
| Production Example 38 | Monosaccharides | 3.02 | Monosaccharides | 1.77 | Monosaccharides | 0.75 | 5.54 |
| | Oligosaccharides | 2.30 | Oligosaccharides | 2.32 | Oligosaccharides | 0.84 | 5.46 |
| | Furfurals | 0.75 | Furfurals | 0.48 | Furfurals | 0.20 | 1.43 |

As shown in Table 7, when the hydrolysis solution 3 extracted from the discharge conduit 2 branching from the discharge port B at the bottom of the hydrolysis device was also recovered in addition to the hydrolysis solutions 1 and 2 extracted from the two locations G1 and G2 (upper and lower) of intermediate extraction ports of the hydrolysis device (Production Example 38), the yield of monosaccharides, oligosaccharides, and furfurals improved in comparison to when the hydrolysis solutions were extracted from the intermediate extraction ports G1 and G2 at two locations of the hydrolysis device (Production Example 36).

It can be concluded from the above results that the recovery of the monosaccharides, oligosaccharides, and furfurals remaining in the hydrolysis suspension discharged to the discharge conduit 2 via the interval leading to the intermediate extraction port G2 on the lower side where the hydrolysis suspension is washed with a washing solution and the discharge port at the bottom of the hydrolysis device contributed to the improvement in the yield of monosaccharides, oligosaccharides, and furfurals.

Production Example 39

Hydrolysis was performed with the device illustrated in FIG. 5. The hydrolysis conditions in the hydrolysis device were the same as those in Production Example 38. Using the same method as in Production Example 38, hydrolysis solutions 1 and 2 extracted from the intermediate extraction ports G1 and G2 at two locations of the hydrolysis device and a hydrolysis solution 3 extracted to the extraction conduit 20 from the hydrolysis suspension discharged to the discharge conduit 2 from the bottom discharge port B were pooled and transferred to a flash tank [manufactured by Shin-Ei Giken (Ltd.), volume: 4 L]. A vapor phase separated by the flash tank (concentration/separation device F) was fed to the condenser C by opening the valve V6 of the vapor phase transfer conduit 9, and after the solution was cooled, a furfural aqueous solution (45 parts by mass/hour) was extracted by the extraction conduit 4. In addition, an aqueous solution containing sugars or the like (405 parts by mass/hour) as a liquid phase in the flash tank was extracted by opening the valve V7 of the extraction conduit 5.

The content of total sugar, monosaccharides, oligosaccharides, and furfurals contained in each aqueous solution obtained from the flash tank was measured, and the yield of each component with respect to the raw material (dry mass) was calculated. The results are shown in Table 8.

TABLE 8

| | | | | Yield (%: relative to raw material) |
|---|---|---|---|---|
| Production Example 39 | Flash tank | Gas phase | Monosaccharides | 0 |
| | | | Oligosaccharides | 0 |
| | | | Furfurals | 2.11 |
| | | Liquid phase | Monosaccharides | 5.51 |
| | | | Oligosaccharides | 5.43 |
| | | | Furfurals | 0.2 |

As shown in Table 8, with the method of Production Example 39, most of the furfural from among the various hydrolysates produced by the continuous hydrolysis of the raw material suspension in the hydrolysis reaction device was extracted from the flash tank while contained in the vapor phase by means of flash distillation in the flash tank. As a result, it was possible to continuously obtain a high-concentration aqueous solution of the furfural that was produced. On the other hand, the liquid phase discharged from the inside of the flash tank after flash distillation contained only a very small amount of furfurals and contained oligosaccharides and monosaccharides at high concentrations. It was thus possible to recover an aqueous solution containing monosaccharides and oligosaccharides at high concentrations from the liquid phase.

Production Examples 40 to 47

*Eucalyptus pellita* chips (2 mm thick) were pulverized using a Wiley mill [manufactured by Tozai Seiki (Ltd.)], and the resulting homogenate was treated with a stainless steel sieve to obtain a wood powder with a particle size of 100 to 120 μm. An aqueous suspension raw material (raw material suspension) containing the raw material biomass was prepared by mixing the resulting wood powder and ion exchange water at a ratio of 5 parts by mass of ion exchange water per 1 part by mass of the wood chips (dry).

The raw material suspension was continuously supplied from the raw material suspension supply conduit 1 connected to the top supply port A of the continuous primary hydrolysis device R1 illustrated in FIG. 6 (made by Kimura Kakoki) at a rate of 400 parts by mass/hour. The solution was hydrolyzed in the continuous primary hydrolysis device R1 at 170° C. and 0.79 MPa, and the hydrolyzed raw material suspension was continuously discharged to the discharge conduit 2 from the bottom discharge port B of the hydrolysis device by opening the decompression valve VP. The retention time in the hydrolysis device was set to three hours. Three hours after supply was begun, the primary hydrolysis solution (130 parts by mass/hour) was extracted from the hydrolysis suspension via the intermediate extraction port G1 (at a position corresponding to a hydrolysis time of 1.5 hours) provided with a stainless steel metal mesh with an opening size of 80 μm in the center of the hydrolysis device in a state in which the temperature and pressure in the hydrolysis device were maintained by opening the decompression valve VP of the discharge conduit 3, and this primary hydrolysis solution was used as the treatment solution of Production Example 40. However, in an experimental example in which the pressure inside the primary hydrolysis device was lower than the pressure inside the secondary hydrolysis device, the primary hydrolysis solution was extracted by opening the valve P using a pump instead of the decompression valve VP (not illustrated).

Next, the primary hydrolysis solution of Production Example 40 was transferred to the secondary hydrolysis device R2 (T1, T2). After the temperature was adjusted in T1, the solution was supplied to the constant-temperature device T2 from a conduit 3A. Hydrolysis was performed in T2 while changing the temperature conditions as follows with a retention time of 10 minutes, and the respective secondary hydrolysis solutions of Production Example 41 (250° C.), Production Example 42 (230° C.), Production Example 43 (200° C.), Production Example 44 (180° C.), Production Example 45 (160° C.), Production Example 46 (140° C.), and Production Example 47 (120° C.) were obtained. The pressure inside the constant-temperature device T2 in each production example was 4.03 MPa (250° C.), 2.85 MPa (230° C.), 1.61 MPa (200° C.), 1.05 MPa (180° C.), 0.67 MPa (160° C.), 0.40 MPa (140° C.), and 0.25 MPa (120° C.). The content of total sugar, monosaccharides, oligosaccharides, and furfurals contained in the hydrolysis solutions (130 parts by mass/hour) of Production Examples 40 to 47 was measured with the same method as in Production Example 1, and the yield of each component with respect to the raw material (dry mass) was calculated. The results are shown in Table 9.

TABLE 9

| | | Yield (%: relative to raw material) |
|---|---|---|
| Production Example 40 (Primary hydrolysis solution) | Total sugar | 7.2 |
| | Monosaccharides | 4.8 |
| | Oligosaccharides | 2.4 |
| | Furfurals | 2.4 |
| Production Example 41 (Secondary hydrolysis solution) 250° C., retention time: 10 minutes | Total sugar | 0.4 |
| | Monosaccharides | 0.4 |
| | Oligosaccharides | 0 |
| | Furfurals | 0 |

TABLE 9-continued

| | | Yield (%: relative to raw material) |
|---|---|---|
| Production Example 42 (Secondary hydrolysis solution) 230° C., retention time: 10 minutes | Total sugar | 3.6 |
| | Monosaccharides | 3.2 |
| | Oligosaccharides | 0.4 |
| | Furfurals | 3.8 |
| Production Example 43 (Secondary hydrolysis solution) 200° C., retention time: 10 minutes | Total sugar | 7.6 |
| | Monosaccharides | 6.0 |
| | Oligosaccharides | 1.6 |
| | Furfurals | 3.1 |
| Production Example 44 (Secondary hydrolysis solution) 180° C., retention time: 10 minutes | Total sugar | 9.6 |
| | Monosaccharides | 6.4 |
| | Oligosaccharides | 3.2 |
| | Furfurals | 3.0 |
| Production Example 45 (Secondary hydrolysis solution) 160° C., retention time: 10 minutes | Total sugar | 10.0 |
| | Monosaccharides | 7.2 |
| | Oligosaccharides | 2.8 |
| | Furfurals | 2.8 |
| Production Example 46 (Secondary hydrolysis solution) 140° C., retention time: 10 minutes | Total sugar | 7.6 |
| | Monosaccharides | 5.2 |
| | Oligosaccharides | 2.4 |
| | Furfurals | 2.7 |
| Production Example 47 (Secondary hydrolysis solution) 120° C., retention time: 10 minutes | Total sugar | 6.8 |
| | Monosaccharides | 4.4 |
| | Oligosaccharides | 2.4 |
| | Furfurals | 2.3 |

As a result of subjecting the primary hydrolysis solution to secondary hydrolysis (hot water treatment, retention time: 10 minutes), the ratios of total sugar, monosaccharides, oligosaccharides, and furfurals contained in the hydrolysis solutions after secondary hydrolysis (Production Examples 41 to 47) changed markedly in comparison to the primary hydrolysis solution (Production Example 40). The yield of furfurals was highest at 230° C. (Production Example 42) and next highest at 200° C. (Production Example 43). The yield of monosaccharides was highest at 160° C. (Production Example 45) and next highest at 180° C. (Production Example 44). The yield of oligosaccharides was highest at 180° C. (Production Example 44) and next highest at 160° C. (Production Example 45). It was ascertained from the above results that when the retention time of the secondary hydrolysis device is 10 minutes, it is possible to control the production ratios of monosaccharides, oligosaccharides, and furfurals by controlling the temperature of secondary hydrolysis. In addition, at 250° C. (Production Example 41), the furfural yield was 0% as a result of changes in furfural due to polymerization.

Production Examples 48 to 54

The primary hydrolysis solution of Production Example 40 was subjected to secondary hydrolysis by setting the retention time of the hydrolysis solution in the secondary hydrolysis device R2 (constant-temperature device T2) to 30 minutes and respectively setting the temperature of the constant-temperature device T2 to 250° C. (Production Example 48), 230° C. (Production Example 49), 200° C. (Production Example 50), 180° C. (Production Example 51), 160° C. (Production Example 52), 140° C. (Production Example 53), and 120° C. (Production Example 54). The pressure inside the constant-temperature device T2 in each production example was, sequentially from Production Example 48, 4.03 MPa (250° C.), 2.85 MPa (230° C.), 1.61 MPa (200° C.), 1.05 MPa (180° C.), 0.67 MPa (160° C.), 0.40 MPa (140° C.), and 0.25 MPa (120° C.).

The hydrolysis solution (130 parts by mass/hour) after secondary hydrolysis was extracted from the secondary hydrolysis solution treatment conduit 10. The content of the total sugar, monosaccharides, oligosaccharides, and furfurals contained in the secondary hydrolysis solution was measured, and the yield of each component with respect to the raw material (dry mass) was calculated. The results are shown in Table 10.

TABLE 10

|  |  | Yield (%: relative to raw material) |
|---|---|---|
| Production Example 40 | Total sugar | 7.2 |
| (Primary hydrolysis solution) | Monosaccharides | 4.8 |
|  | Oligosaccharides | 2.4 |
|  | Furfurals | 2.4 |
| Production Example 48 | Total sugar | 0.3 |
| (Secondary hydrolysis solution) | Monosaccharides | 0.3 |
| 250° C., retention time: 30 minutes | Oligosaccharides | 0 |
|  | Furfurals | 0 |
| Production Example 49 | Total sugar | 3.1 |
| (Secondary hydrolysis solution) | Monosaccharides | 2.8 |
| 230° C., retention time: 30 minutes | Oligosaccharides | 0.3 |
|  | Furfurals | 3.8 |
| Production Example 50 | Total sugar | 5.7 |
| (Secondary hydrolysis solution) | Monosaccharides | 4.5 |
| 200° C., retention time: 30 minutes | Oligosaccharides | 1.2 |
|  | Furfurals | 4.1 |
| Production Example 51 | Total sugar | 8.6 |
| (Secondary hydrolysis solution) | Monosaccharides | 5.6 |
| 180° C., retention time: 30 minutes | Oligosaccharides | 3.0 |
|  | Furfurals | 4.2 |
| Production Example 52 | Total sugar | 10.0 |
| (Secondary hydrolysis solution) | Monosaccharides | 6.7 |
| 160° C., retention time: 30 minutes | Oligosaccharides | 3.3 |
|  | Furfurals | 3.1 |
| Production Example 53 | Total sugar | 7.3 |
| (Secondary hydrolysis solution) | Monosaccharides | 4.1 |
| 140° C., retention time: 30 minutes | Oligosaccharides | 3.2 |
|  | Furfurals | 2.8 |
| Production Example 54 | Total sugar | 6.6 |
| (Secondary hydrolysis solution) | Monosaccharides | 4.2 |
| 120° C., retention time: 30 minutes | Oligosaccharides | 2.4 |
|  | Furfurals | 2.3 |

As a result of subjecting the primary hydrolysis solution to secondary hydrolysis (hot water treatment, retention time: 30 minutes), the ratios of total sugar, monosaccharides, oligosaccharides, and furfurals contained in the hydrolysis solutions after secondary hydrolysis (Production Examples 48 to 54) changed markedly in comparison to the primary hydrolysis solution (Production Example 40). The yield of furfurals was highest at 180° C. (Production Example 51) and next highest at 200° C. (Production Example 50). The yield of monosaccharides was highest at 160° C. (Production Example 52) and next highest at 180° C. (Production Example 51). The yield of oligosaccharides was highest at 160° C. (Production Example 52) and next highest at 140° C. (Production Example 53). In addition, at 250° C. (Production Example 48), the furfural yield was 0% as a result of changes in furfural due to polymerization.

Production Examples 55 to 61

The primary hydrolysis solution of Production Example 40 was subjected to secondary hydrolysis by setting the retention time of the hydrolysis solution in the secondary hydrolysis device R2 (constant-temperature device T2) to 60 minutes and respectively setting the temperature of the constant-temperature device T2 to 250° C. (Production Example 55), 230° C. (Production Example 56), 200° C. (Production Example 57), 180° C. (Production Example 58), 160° C. (Production Example 59), 140° C. (Production Example 60), and 120° C. (Production Example 61). The pressure inside the constant-temperature device T2 in each production example was, sequentially from Production Example 55, 4.03 MPa (250° C.), 2.85 MPa (230° C.), 1.61 MPa (200° C.), 1.05 MPa (180° C.), 0.67 MPa (160° C.), 0.40 MPa (140° C.), and 0.25 MPa (120° C.).

The hydrolysis solution (130 parts by mass/hour) after secondary hydrolysis was extracted from the secondary hydrolysis solution treatment conduit 10. The content of the total sugar, monosaccharides, oligosaccharides, and furfurals contained in the secondary hydrolysis solution was measured, and the yield of each component with respect to the raw material (dry mass) was calculated. The results are shown in Table 11.

TABLE 11

|  |  | Yield (%: relative to raw material) |
|---|---|---|
| Production Example 40 | Total sugar | 7.2 |
| (Primary hydrolysis solution) | Monosaccharides | 4.8 |
|  | Oligosaccharides | 2.4 |
|  | Furfurals | 2.4 |
| Production Example 55 | Total sugar | 0 |
| (Secondary hydrolysis solution) | Monosaccharides | 0 |
| 250° C., retention time: 60 minutes | Oligosaccharides | 0 |
|  | Furfurals | 0 |
| Production Example 56 | Total sugar | 1.0 |
| (Secondary hydrolysis solution) | Monosaccharides | 0.8 |
| 230° C., retention time: 60 minutes | Oligosaccharides | 0.2 |
|  | Furfurals | 4.8 |
| Production Example 57 | Total sugar | 3.6 |
| (Secondary hydrolysis solution) | Monosaccharides | 3.2 |
| 200° C., retention time: 60 minutes | Oligosaccharides | 0.4 |
|  | Furfurals | 5.2 |
| Production Example 58 | Total sugar | 7.6 |
| (Secondary hydrolysis solution) | Monosaccharides | 4.8 |
| 180° C., retention time: 60 minutes | Oligosaccharides | 2.8 |
|  | Furfurals | 4.4 |
| Production Example 59 | Total sugar | 10.4 |
| (Secondary hydrolysis solution) | Monosaccharides | 6.4 |
| 160° C., retention time: 60 minutes | Oligosaccharides | 4.0 |
|  | Furfurals | 3.6 |
| Production Example 60 | Total sugar | 7.2 |
| (Secondary hydrolysis solution) | Monosaccharides | 3.6 |
| 140° C., retention time: 60 minutes | Oligosaccharides | 3.6 |
|  | Furfurals | 3.0 |
| Production Example 61 | Total sugar | 6.4 |
| (Secondary hydrolysis solution) | Monosaccharides | 4.0 |
| 120° C., retention time: 60 minutes | Oligosaccharides | 2.4 |
|  | Furfurals | 2.3 |

As a result of subjecting the primary hydrolysis solution to secondary hydrolysis (hot water treatment, retention time: 60 minutes), the ratios of total sugar, monosaccharides, oligosaccharides, and furfurals contained in the hydrolysis solutions after secondary hydrolysis (Production Examples 55 to 61) changed markedly in comparison to the primary hydrolysis solution (Production Example 40). The yield of furfurals was highest at 200° C. (Production Example 57) and next highest at 230° C. (Production Example 56). The yield of monosaccharides was highest at 160° C. (Production Example 59) and next highest at 180° C. (Production Example 58). The yield of oligosaccharides was highest at 160° C. (Production Example 59) and next highest at 140° C. (Production Example 60). In addition, at 250° C. (Production Example 55), the furfural yield was 0% as a result of changes in furfural due to polymerization.

Production Examples 62 to 68

The primary hydrolysis solution of Production Example 40 was subjected to secondary hydrolysis by setting the retention time of the hydrolysis solution in the secondary hydrolysis device R2 (constant-temperature device T2) to 120 minutes and respectively setting the temperature of the constant-temperature device T2 to 250° C. (Production Example 62), 230° C. (Production Example 63), 200° C. (Production Example 64), 180° C. (Production Example 65), 160° C. (Production Example 66), 140° C. (Production Example 67), and 120° C. (Production Example 68). The pressure inside the constant-temperature device T2 in each production example was, sequentially from Production Example 62, 4.03 MPa (250° C.), 2.85 MPa (230° C.), 1.61 MPa (200° C.), 1.05 MPa (180° C.), 0.67 MPa (160° C.), 0.40 MPa (140° C.), and 0.25 MPa (120° C.).

The content of the total sugar, monosaccharides, oligosaccharides, and furfurals contained in the secondary hydrolysis solution was measured, and the yield of each component with respect to the raw material (dry mass) was calculated. The results are shown in Table 12.

TABLE 12

| | | Yield (%: relative to raw material) |
|---|---|---|
| Production Example 40 | Total sugar | 7.2 |
| (Primary hydrolysis solution) | Monosaccharides | 4.8 |
| | Oligosaccharides | 2.4 |
| | Furfurals | 2.4 |
| Production Example 62 | Total sugar | 0 |
| (Secondary hydrolysis solution) | Monosaccharides | 0 |
| 250° C., retention time: 120 minutes | Oligosaccharides | 0 |
| | Furfurals | 0 |
| Production Example 63 | Total sugar | 0.2 |
| (Secondary hydrolysis solution) | Monosaccharides | 0.2 |
| 230° C., retention time: 120 minutes | Oligosaccharides | 0 |
| | Furfurals | 4.0 |
| Production Example 64 | Total sugar | 4.8 |
| (Secondary hydrolysis solution) | Monosaccharides | 4.6 |
| 200° C., retention time: 120 minutes | Oligosaccharides | 0.2 |
| | Furfurals | 5.0 |
| Production Example 65 | Total sugar | 7.6 |
| (Secondary hydrolysis solution) | Monosaccharides | 5.6 |
| 180° C., retention time: 120 minutes | Oligosaccharides | 2.0 |
| | Furfurals | 5.4 |
| Production Example 66 | Total sugar | 10.6 |
| (Secondary hydrolysis solution) | Monosaccharides | 7.6 |
| 160° C., retention time: 120 minutes | Oligosaccharides | 3.0 |
| | Furfurals | 5.6 |
| Production Example 67 | Total sugar | 8.6 |
| (Secondary hydrolysis solution) | Monosaccharides | 5.8 |
| 140° C., retention time: 120 minutes | Oligosaccharides | 2.8 |
| | Furfurals | 3.5 |
| Production Example 68 | Total sugar | 6.0 |
| (Secondary hydrolysis solution) | Monosaccharides | 3.8 |
| 120° C., retention time: 120 minutes | Oligosaccharides | 2.2 |
| | Furfurals | 2.2 |

As a result of subjecting the primary hydrolysis solution of Production Example 40 to secondary hydrolysis (hot water treatment, retention time: 120 minutes), the ratios of total sugar, monosaccharides, oligosaccharides, and furfurals contained in the hydrolysis solutions after secondary hydrolysis (Production Examples 62 to 68) changed markedly in comparison to the primary hydrolysis solution (Production Example 40). The yield of furfurals was highest at 160° C. (Production Example 66) and next highest at 180° C. (Production Example 65). The yield of monosaccharides was highest at 160° C. (Production Example 66) and next highest at 140° C. (Production Example 67). The yield of oligosaccharides was highest at 160° C. (Production Example 66) and next highest at 140° C. (Production Example 67). In addition, at 250° C. (Production Example 62), the furfural yield was 0% as a result of changes in furfural due to polymerization.

It was ascertained from the results of Production Examples 62 to 68 that it is possible to control the production ratios of monosaccharides, oligosaccharides, and furfurals by controlling not only the temperature of the secondary hydrolysis solution but also the retention time.

Production Examples 69 to 75

Sulfuric acid was added to the primary hydrolysis solution (pH 3.8) of Production Example 40 to adjust the pH to 1.0. This primary hydrolysis solution (pH 1.0) was transferred to the secondary hydrolysis device R2 (T1, T2) and subjected to secondary hydrolysis by setting the retention time of the hydrolysis solution in the secondary hydrolysis device R2 (constant-temperature device T2) to 10 minutes and respectively setting the temperature of the secondary hydrolysis device R2 (constant-temperature device T2) to 250° C. (Production Example 69), 230° C. (Production Example 70), 200° C. (Production Example 71), 180° C. (Production Example 72), 160° C. (Production Example 73), 140° C. (Production Example 74), and 120° C. (Production Example 75). The pressure inside the constant-temperature device T2 in each production example was, sequentially from Production Example 69, 4.03 MPa (250° C.), 2.85 MPa (230° C.), 1.61 MPa (200° C.), 1.05 MPa (180° C.), 0.67 MPa (160° C.), 0.40 MPa (140° C.), and 0.25 MPa (120° C.).

The content of the total sugar, monosaccharides, oligosaccharides, and furfurals contained in the secondary hydrolysis solution was measured, and the yield of each component with respect to the raw material (dry mass) was calculated. The results are shown in Table 13.

TABLE 13

| | | Yield (%: relative to raw material) |
|---|---|---|
| Production Example 40 | Total sugar | 7.2 |
| (Primary hydrolysis solution) | Monosaccharides | 4.8 |
| | Oligosaccharides | 2.4 |
| | Furfurals | 2.4 |
| Production Example 69 | Total sugar | 0.4 |
| (Secondary hydrolysis solution) | Monosaccharides | 0.4 |
| 250° C., retention time: 10 minutes, | Oligosaccharides | 0 |
| pH 1 | Furfurals | 0 |
| Production Example 70 | Total sugar | 2.8 |
| (Secondary hydrolysis solution) | Monosaccharides | 2.8 |
| 230° C., retention time: 10 minutes, | Oligosaccharides | 0 |
| pH 1 | Furfurals | 3.2 |
| Production Example 71 | Total sugar | 6.8 |
| (Secondary hydrolysis solution) | Monosaccharides | 5.2 |
| 200° C., retention time: 10 minutes, | Oligosaccharides | 1.6 |
| pH 1 | Furfurals | 4.0 |
| Production Example 72 | Total sugar | 10.4 |
| (Secondary hydrolysis solution) | Monosaccharides | 7.6 |
| 180° C., retention time: 10 minutes, | Oligosaccharides | 2.8 |
| pH 1 | Furfurals | 3.3 |
| Production Example 73 | Total sugar | 12.0 |
| (Secondary hydrolysis solution) | Monosaccharides | 8.0 |
| 160° C., retention time: 10 minutes, | Oligosaccharides | 4.0 |
| pH 1 | Furfurals | 3.0 |
| Production Example 74 | Total sugar | 9.2 |
| (Secondary hydrolysis solution) | Monosaccharides | 6.0 |
| 140° C., retention time: 10 minutes, | Oligosaccharides | 3.2 |
| pH 1 | Furfurals | 2.8 |
| Production Example 75 | Total sugar | 7.6 |
| (Secondary hydrolysis solution) | Monosaccharides | 5.2 |
| 120° C., retention time: 10 minutes, | Oligosaccharides | 2.4 |
| pH 1 | Furfurals | 2.3 |

As a result of subjecting the primary hydrolysis solution (pH 1.0) to secondary hydrolysis (acid treatment, retention time: 10 minutes), the ratios of total sugar, monosaccharides, oligosaccharides, and furfurals contained in the hydrolysis solutions after secondary hydrolysis (Production Examples 69 to 75) changed markedly in comparison to the primary hydrolysis solution (Production Example 40). The yield of furfurals was highest at 200° C. (Production Example 71) and next highest at 230° C. (Production Example 70). The yield of monosaccharides was highest at 160° C. (Production Example 73) and next highest at 180° C. (Production Example 72). The yield of oligosaccharides was highest at 160° C. (Production Example 73) and next highest at 140° C. (Production Example 74). It was ascertained from the above results that even when secondary hydrolysis is performed after the primary hydrolysis solution is made acidic, it is possible to control the production ratios of monosaccharides, oligosaccharides, and furfurals. In addition, at 250° C. (Production Example 69), the furfural yield was 0% as a result of changes in furfural due to polymerization.

Production Examples 76 to 82

In the continuous primary hydrolysis device R1 illustrated in FIG. 6, primary hydrolysis was performed with the same method as in Production Example 40 with the exception of supplying washing water at a rate of 400 parts by mass/hour from the washing solution supply device W1 at the bottom of the device via the washing water supply conduit 6 and bringing the solution into contact, in a countercurrent manner, with a hydrolysis suspension moving downward from the intermediate extraction port G1 of the continuous primary hydrolysis device R1 provided with a stainless steel metal mesh having an opening size of 80 μm.

Three hours after supply was begun, the primary hydrolysis solution (260 parts by mass/hour) separated from the hydrolysis suspension was extracted from the discharge conduit 3 via the intermediate extraction port G1 (at a position corresponding to a hydrolysis time of 1.5 hours) provided with a stainless steel metal mesh with an opening size of 80 μm in the center of the continuous primary hydrolysis device R1 in a state in which the temperature and pressure in the hydrolysis device were maintained, and the solution was transferred to the secondary hydrolysis device R2. After the temperature of the primary hydrolysis solution supplied to the temperature adjustment device T1 was adjusted inside T1, the solution was supplied to the constant-temperature device T2 from the conduit 3A and subjected to secondary hydrolysis with a retention time of 10 minutes in T2 by respectively setting the temperature of the secondary hydrolysis device R2 (constant-temperature device T2) to 250° C. (Production Example 76), 230° C. (Production Example 77), 200° C. (Production Example 78), 180° C. (Production Example 79), 160° C. (Production Example 80), 140° C. (Production Example 81), and 120° C. (Production Example 82). The pressure inside the constant-temperature device T2 in each experimental example was, sequentially from Production Example 76, 4.03 MPa (250° C.), 2.85 MPa (230° C.), 1.61 MPa (200° C.), 1.05 MPa (180° C.), 0.67 MPa (160° C.), 0.40 MPa (140° C.), and 0.25 MPa (120° C.).

The content of the total sugar, monosaccharides, oligosaccharides, and furfurals contained in the secondary hydrolysis solution was measured, and the yield of each component with respect to the raw material (dry mass) was calculated. The results are shown in Table 14.

TABLE 14

| | | Yield (%: relative to raw material) |
|---|---|---|
| Production Example 76 | Total sugar | 0.8 |
| (Secondary hydrolysis solution) | Monosaccharides | 0.8 |
| 250° C., retention time: 10 minutes | Oligosaccharides | 0 |
| | Furfurals | 0 |
| Production Example 77 | Total sugar | 4.0 |
| (Secondary hydrolysis solution) | Monosaccharides | 3.6 |
| 230° C., retention time: 10 minutes | Oligosaccharides | 0.4 |
| | Furfurals | 4.0 |
| Production Example 78 | Total sugar | 8.8 |
| (Secondary hydrolysis solution) | Monosaccharides | 6.8 |
| 200° C., retention time: 10 minutes | Oligosaccharides | 2.0 |
| | Furfurals | 3.3 |
| Production Example 79 | Total sugar | 6.8 |
| (Secondary hydrolysis solution) | Monosaccharides | 3.2 |
| 180° C., retention time: 10 minutes | Oligosaccharides | 3.6 |
| | Furfurals | 3.2 |
| Production Example 80 | Total sugar | 11.2 |
| (Secondary hydrolysis solution) | Monosaccharides | 8.0 |
| 160° C., retention time: 10 minutes | Oligosaccharides | 3.2 |
| | Furfurals | 3.0 |
| Production Example 81 | Total sugar | 8.8 |
| (Secondary hydrolysis solution) | Monosaccharides | 5.6 |
| 140° C., retention time: 10 minutes | Oligosaccharides | 3.2 |
| | Furfurals | 2.9 |
| Production Example 82 | Total sugar | 8.0 |
| (Secondary hydrolysis solution) | Monosaccharides | 5.2 |
| 120° C., retention time: 10 minutes | Oligosaccharides | 2.8 |
| | Furfurals | 2.4 |

With the systems in which a washing solution was supplied to the continuous primary hydrolysis device R1 illustrated in FIG. 6 (Production Examples 76 to 82), the yield of monosaccharides, oligosaccharides, and furfurals contained in the hydrolysis solution after secondary hydrolysis improved in comparison to the systems in which the washing solution of FIG. 6 was not supplied (Production Examples 41 to 47).

Production Example 83

With the device illustrated in FIG. 7, the primary hydrolysis solution of Production Example 40 extracted from the continuous primary hydrolysis device R1 was subjected to secondary hydrolysis by the secondary hydrolysis device R2 under the same conditions as those of Production Example 43. However, the secondary hydrolysis solution discharged from the constant-temperature device T2 was not cooled, and the hydrolysis solution was transferred to a flash tank (manufactured by Shin-Ei Giken (Ltd.), volume: 4 L) by opening the valve VB of the secondary hydrolysis solution transfer conduit 10. A vapor phase separated by the flash tank (concentration/separation device F) was cooled by the condenser C, and a furfural aqueous solution (9.9 parts by mass/hour) was extracted from the condensate extraction conduit 4 (furfural aqueous solution recovery conduit). In addition, an aqueous solution containing sugars or the like (120 parts by mass/hour) was extracted from the liquid phase extraction conduit 5 as a liquid phase in the flash tank.

The content of total sugar, monosaccharides, oligosaccharides, and furfurals contained in each aqueous solution obtained from the flash tank was measured, and the yield of each component with respect to the raw material (dry mass) was calculated. The results are shown in Table 15.

TABLE 15

| Production Example 83 | Flash tank | Gas phase | Total sugar | 0 |
|---|---|---|---|---|
| | | | Monosaccharides | 0 |
| | | | Oligosaccharides | 0 |
| | | | Furfurals | 7.8 |
| | Flash tank | Liquid phase | Total sugar | 7.6 |
| | | | Monosaccharides | 6.0 |
| | | | Oligosaccharides | 1.6 |
| | | | Furfurals | 0.6 |

Yield (%: relative to raw material)

Production Example 84

With the device illustrated in FIG. 7, the primary hydrolysis solution of Production Example 40 extracted from the continuous primary hydrolysis device R1 was subjected to secondary hydrolysis by the secondary hydrolysis device R2 under the same conditions as those of Production Example 78. However, the secondary hydrolysis solution discharged from the constant-temperature device T2 was not cooled, and the secondary hydrolysis solution was transferred to a flash tank (manufactured by Shin-Ei Giken (Ltd.), volume: 4 L) by opening the valve VB of the secondary hydrolysis solution transfer conduit 10. A vapor phase separated by the flash tank (concentration/separation device F) was cooled by the condenser C, and a furfural aqueous solution (19.8 parts by mass/hour) was extracted from the condensate extraction conduit 4 (furfural aqueous solution recovery conduit). In addition, an aqueous solution containing sugars or the like (239 parts by mass/hour) was extracted from the liquid phase extraction conduit 5 as a liquid phase in the flash tank.

The content of total sugar, monosaccharides, oligosaccharides, and furfurals contained in each aqueous solution obtained from the flash tank was measured, and the yield of each component with respect to the raw material (dry mass) was calculated. The results are shown in Table 16.

TABLE 16

| Production Example 84 | Flash tank | Gas phase | Total sugar | 0 |
|---|---|---|---|---|
| | | | Monosaccharides | 0 |
| | | | Oligosaccharides | 0 |
| | | | Furfurals | 8.1 |
| | Flash tank | Liquid phase | Total sugar | 8.8 |
| | | | Monosaccharides | 6.8 |
| | | | Oligosaccharides | 2.0 |
| | | | Furfurals | 0.6 |

Yield (%: relative to raw material)

As shown in Tables 15 and 16, with the methods of Production Examples 83 and 84, most of the furfural from among the various hydrolysates produced by the hydrolysis reaction was extracted from the flash tank while contained in the vapor phase by means of flash distillation in the flash tank. As a result, it was possible to continuously obtain a high-concentration aqueous solution of the furfural that was produced. On the other hand, the liquid phase discharged from the inside of the flash tank after flash distillation contained only a very small amount of furfurals and contained oligosaccharides and monosaccharides at high concentrations. It was thus possible to recover an aqueous solution containing monosaccharides and oligosaccharides at high concentrations from the liquid phase.

Production Examples 85 to 91

Using the device illustrated in FIG. 8, primary hydrolysis was performed with the same method as in Production Example 40. Next, the primary hydrolysis solution of Production Example 1 described above was transferred to the secondary reaction vessel BR2, and hydrolysis was performed using the secondary reaction vessel BR2 while changing the temperature conditions as follows with a retention time of 30 minutes to obtain the respective secondary hydrolysis solutions of Production Example 85 (250° C.), Production Example 86 (230° C.), Production Example 87 (200° C.), Production Example 88 (180° C.), Production Example 89 (160° C.), Production Example 90 (140° C.), and Production Example 91 (120° C.). The pressure inside the reaction vessel in each production example was 4.03 MPa (250° C.), 2.85 MPa (230° C.), 1.61 MPa (200° C.), 1.05 MPa (180° C.), 0.67 MPa (160° C.), 0.40 MPa (140° C.), and 0.25 MPa (120° C.). The content of total sugar, monosaccharides, oligosaccharides, and furfurals contained in the hydrolysis solutions (130 parts by mass/hour) of Production Examples 85 to 91 was measured, and the yield of each component with respect to the raw material (dry mass) was calculated. The results are shown in Table 17.

TABLE 17

| | | Yield (%: relative to raw material) |
|---|---|---|
| Production Example 40 (Primary hydrolysis solution) | Total sugar | 7.2 |
| | Monosaccharides | 4.8 |
| | Oligosaccharides | 2.4 |
| | Furfurals | 2.4 |
| Production Example 85 (Secondary hydrolysis solution) 250° C., retention time: 30 minutes | Total sugar | 0.5 |
| | Monosaccharides | 0.5 |
| | Oligosaccharides | 0 |
| | Furfurals | 0 |
| Production Example 86 (Secondary hydrolysis solution) 230° C., retention time: 30 minutes | Total sugar | 3.7 |
| | Monosaccharides | 3.2 |
| | Oligosaccharides | 0.5 |
| | Furfurals | 3.6 |
| Production Example 87 (Secondary hydrolysis solution) 200° C., retention time: 30 minutes | Total sugar | 6.7 |
| | Monosaccharides | 4.9 |
| | Oligosaccharides | 1.6 |
| | Furfurals | 3.9 |
| Production Example 88 (Secondary hydrolysis solution) 180° C., retention time: 30 minutes | Total sugar | 8.9 |
| | Monosaccharides | 5.7 |
| | Oligosaccharides | 3.2 |
| | Furfurals | 4.1 |
| Production Example 89 (Secondary hydrolysis solution) 160° C., retention time: 30 minutes | Total sugar | 9.8 |
| | Monosaccharides | 6.5 |
| | Oligosaccharides | 3.3 |
| | Furfurals | 3.2 |
| Production Example 90 (Secondary hydrolysis solution) 140° C., retention time: 30 minutes | Total sugar | 7.8 |
| | Monosaccharides | 4.3 |
| | Oligosaccharides | 3.5 |
| | Furfurals | 2.6 |
| Production Example 91 (Secondary hydrolysis solution) 120° C., retention time: 30 minutes | Total sugar | 7.3 |
| | Monosaccharides | 4.5 |
| | Oligosaccharides | 2.8 |
| | Furfurals | 2.1 |

As a result of subjecting the primary hydrolysis solution to secondary hydrolysis (hot water treatment, retention time: 30 minutes) with the reaction vessel BR2, the ratios of total sugar, monosaccharides, oligosaccharides, and furfurals contained in the hydrolysis solutions after secondary hydrolysis (Production Examples 85 to 91) changed markedly in comparison to the primary hydrolysis solution (Production Example 40). The yield of furfurals was highest at 180° C. (Production Example 88) and next highest at 200° C. (Production Example 87). The yield of monosaccharides was highest at 160° C. (Production Example 89) and next highest at 180° C. (Production Example 88). The yield of oligosaccharides was highest at 140° C. (Production Example 90) and next highest at 160° C. (Production Example 89). It was ascertained from the above results that when the retention time of the secondary hydrolysis device is 30 minutes, it is possible to control the production ratios of monosaccharides, oligosaccharides, and furfurals by controlling the temperature of secondary hydrolysis. In addition, at 250° C. (Production Example 85), the furfural yield was 0% as a result of changes in furfural due to polymerization.

Production Example 92

With the device illustrated in FIG. 9, the primary hydrolysis solution of Production Example 40 extracted from the continuous primary hydrolysis device R1 was subjected to secondary hydrolysis by the secondary reaction vessel BR2 under the same conditions as those of Production Example 87. Next, the hydrolysis solution was transferred to a flash tank (manufactured by Shin-Ei Giken (Ltd.), volume: 4 L) by opening the valve V of the secondary hydrolysis solution transfer conduit 11. A vapor phase separated by the flash tank (concentration/separation device F) was cooled by the condenser C, and a furfural aqueous solution (10 parts by mass/hour) was extracted from the furfural aqueous solution recovery conduit 4. In addition, an aqueous solution containing sugars or the like (120 parts by mass/hour) was extracted from the conduit 5 as a liquid phase in the flash tank.

The content of total sugar, monosaccharides, oligosaccharides, and furfurals contained in each aqueous solution obtained from the flash tank was measured, and the yield of each component with respect to the raw material (dry mass) was calculated. The results are shown in Table 18.

TABLE 18

| | | | | Yield (%: relative to raw material) |
|---|---|---|---|---|
| Production Example 92 | Flash tank | Gas phase | Total sugar | 0 |
| | | | Monosaccharides | 0 |
| | | | Oligosaccharides | 0 |
| | | | Furfurals | 7.5 |
| | Flash tank | Liquid phase | Total sugar | 6.7 |
| | | | Monosaccharides | 4.9 |
| | | | Oligosaccharides | 1.6 |
| | | | Furfurals | 0.6 |

As shown in Table 18, with the method of Production Example 92, most of the furfural from among the various hydrolysates produced by the hydrolysis reaction was extracted from the flash tank while contained in the vapor phase by means of flash distillation in the flash tank. As a result, it was possible to continuously obtain a high-concentration aqueous solution of high-purity furfural. On the other hand, the liquid phase discharged from the inside of the flash tank after flash distillation contained only a very small amount of furfurals and contained oligosaccharides and monosaccharides at high concentrations. It was thus possible to recover an aqueous solution containing monosaccharides and oligosaccharides at high concentrations from the liquid phase.

Practical Example 1

Using the device illustrated in FIG. 10, primary hydrolysis was performed with the same method as in Production Example 40. Next, the primary hydrolysis solution was transferred to the secondary hydrolysis device R2 (T1, T2), and after the temperature was adjusted inside T1, the solution was supplied to the constant-temperature device T2 from the conduit 3A. Hydrolysis was performed inside T2 under a pressure of 1.05 MPa and at 180° C. with a retention time of 10 minutes, and a secondary hydrolysis solution was thus obtained. The secondary hydrolysis solution discharged from the constant-temperature device T2 was not cooled, and the hydrolysis solution was transferred to a flash tank (manufactured by Shin-Ei Giken (Ltd.), volume: 4 L) by opening the valve VB of the secondary hydrolysis solution transfer conduit 10. A vapor phase separated by the flash tank (concentration/separation device) was cooled by the condenser C, and a furfural aqueous solution (10 parts by mass/hour) was extracted from the furfural aqueous solution recovery conduit 4. On the other hand, an aqueous solution containing sugars or the like (120 parts by mass/hour) was extracted from the conduit 5 as a liquid phase inside the flash tank, and the solution was supplied to the supply port of the secondary hydrolysis device R2 (T1→T2) via the circulation conduit 14 for an aqueous solution containing sugars or the like and then continuously circulated. At the point when circulation to the secondary hydrolysis device R2 was begun, the feed rate of the primary hydrolysis solution from the continuous primary hydrolysis device R1 to the secondary hydrolysis device R2 was adjusted to 10 parts by mass/hour, and operation (steady state operation) was continuously maintained thereafter.

During steady state operation (30 minutes after circulation was begun), the content of total sugar, monosaccharides, oligosaccharides, and furfurals contained in each aqueous solution obtained from the flash tank was measured, and the yield of each component with respect to the raw material (dry mass) was calculated. The results are shown in Table 19.

Comparative Example 1

A test in which the aqueous solution containing sugars (liquid phase) separated by the flash tank in the method of Practical Example 1 was not circulated to the secondary hydrolysis device was used as a Comparative Example 1. The results are shown in Table 19.

TABLE 19

| | | | Yield (%: relative to raw material) Flash tank | |
|---|---|---|---|---|
| | Secondary hydrolysis conditions | | Gas phase | Liquid phase |
| Practical Example 1 | Temperature: 180° C., retention time: 10 minutes With circulation (measured 30 minutes after circulation was begun) | Total sugar Monosaccharides Oligosaccharides Furfurals | 0 0 0 9.2 | 7.4 4.8 2.6 0.5 |
| Comparative Example 1 | Temperature: 180° C., retention time: 10 minutes No circulation | Total sugar Monosaccharides Oligosaccharides Furfurals | 0 0 0 6.4 | 9.6 6.4 3.2 0.5 |

It was ascertained from the results of Table 19 that when an aqueous solution containing a sugar solution separated by the flash tank is continuously circulated to the secondary hydrolysis device R2 (180° C., retention time: 10 minutes) (Practical Example 1), furfural can be more efficiently recovered than when the solution is not circulated to the secondary hydrolysis device R2 (Comparative Example 1).

Practical Example 2

Practical Example 2 was implemented with the same method as in Practical Example 1 with the exception that the retention time in the secondary hydrolysis device in Practical Example 1 was changed to 20 minutes. During steady state operation (60 minutes after circulation was begun), the content of total sugar, monosaccharides, oligosaccharides, and furfurals contained in each aqueous solution obtained from the flash tank was measured, and the yield of each component with respect to the raw material (dry mass) was calculated. The results are shown in Table 20.

Comparative Example 2

A test in which the aqueous solution containing sugars (liquid phase) separated by the flash tank in the method of Practical Example 2 was not circulated to the secondary hydrolysis device R2 was used as a Comparative Example 2. The results are shown in Table 20.

TABLE 20

| | Secondary hydrolysis conditions | | Yield (%: relative to raw material) Flash tank | |
| --- | --- | --- | --- | --- |
| | | | Gas phase | Liquid phase |
| Practical Example 2 | Temperature: 180° C., retention time: 20 minutes With circulation (measured 60 minutes after circulation was begun) | Total sugar Monosaccharides Oligosaccharides Furfurals | 0 0 0 12.6 | 3.5 2.1 1.4 0.5 |
| Comparative Example 2 | Temperature: 180° C., retention time: 20 minutes No circulation | Total sugar Monosaccharides Oligosaccharides Furfurals | 0 0 0 6.9 | 9.2 6.1 3.1 0.5 |

It was ascertained from the results of Table 20 that when an aqueous solution containing a sugar solution separated by the flash tank is continuously circulated to the secondary hydrolysis device R2 (180° C., retention time: 20 minutes) (Practical Example 2), furfural can be efficiently recovered in comparison to when the solution is not circulated to the secondary hydrolysis device R2 (Comparative Example 2).

Practical Example 3

Practical Example 3 was implemented with the same method as in Practical Example 1 with the exception that the retention time in the secondary hydrolysis device R2 in Practical Example 1 was changed to 30 minutes. During steady state operation (90 minutes after circulation was begun), the content of total sugar, monosaccharides, oligosaccharides, and furfurals contained in each aqueous solution obtained from the flash tank was measured, and the yield of each component with respect to the raw material (dry mass) was calculated. The results are shown in Table 21.

Comparative Example 3

A test in which the aqueous solution containing sugars (liquid phase) separated by the flash tank in the method of Practical Example 3 was not circulated to the secondary hydrolysis device R2 was used as a Comparative Example 3. The results are shown in Table 21.

TABLE 21

| | Secondary hydrolysis conditions | | Yield (%: relative to raw material) Flash tank | |
| --- | --- | --- | --- | --- |
| | | | Gas phase | Liquid phase |
| Practical Example 3 | Temperature: 180° C., retention time: 30 minutes With circulation (measured 90 minutes after circulation was begun) | Total sugar Monosaccharides Oligosaccharides Furfurals | 0 0 0 10.6 | 3.0 1.8 1.2 0.5 |
| Comparative Example 3 | Temperature: 180° C., retention time: 30 minutes No circulation | Total sugar Monosaccharides Oligosaccharides Furfurals | 0 0 0 7.5 | 9.6 6.4 3.2 0.5 |

It was ascertained that when an aqueous solution containing a sugar solution separated by the flash tank is continuously circulated to the secondary hydrolysis device R2 (180° C., retention time: 30 minutes) (Practical Example 3), furfural can be efficiently recovered in comparison to when the solution is not circulated to the secondary hydrolysis device R2 (Comparative Example 3).

Practical Example 4

Practical Example 4 was implemented with the same method as in Practical Example 1 with the exception that the retention time in the secondary hydrolysis device R2 in Practical Example 1 was changed to 40 minutes. During steady state operation (120 minutes after circulation was begun), the content of total sugar, monosaccharides, oligosaccharides, and furfurals contained in each aqueous solution obtained from the flash tank was measured, and the yield of each component with respect to the raw material (dry mass) was calculated. The results are shown in Table 22.

Comparative Example 4

A test in which the aqueous solution containing sugars (liquid phase) separated by the flash tank in the method of Practical Example 4 was not circulated to the secondary hydrolysis device R2 was used as a Comparative Example 4. The results are shown in Table 22.

TABLE 22

| | Secondary hydrolysis conditions | | Yield (%: relative to raw material) Flash tank | |
| --- | --- | --- | --- | --- |
| | | | Gas phase | Liquid phase |
| Practical Example 4 | Temperature: 180° C., retention time: 40 minutes With circulation (measured 120 minutes after circulation was begun) | Total sugar Monosaccharides Oligosaccharides Furfurals | 0 0 0 10.2 | 2.5 1.5 1.0 0.5 |

TABLE 22-continued

| | Secondary hydrolysis conditions | | Yield (%: relative to raw material) Flash tank | |
| --- | --- | --- | --- | --- |
| | | | Gas phase | Liquid phase |
| Comparative Example 4 | Temperature: 180° C., retention time: 40 minutes No circulation | Total sugar Monosaccharides Oligosaccharides Furfurals | 0 0 0 7.2 | 8.3 5.3 3.0 0.5 |

It was ascertained that when an aqueous solution containing a sugar solution separated by the flash tank is continuously circulated to the secondary hydrolysis device R2 (180° C., retention time: 40 minutes) (Practical Example 4), furfural can be efficiently recovered in comparison to when the solution is not circulated to the secondary hydrolysis device R2 (Comparative Example 4). In addition, in a comparison of Practical Examples 1 to 4, the furfural yield was highest when the retention time of secondary hydrolysis was 20 minutes (Practical Example 2).

The yields (list) of furfurals recovered from the gaseous phased separated by the flash tank, as excerpted from the results of Practical Examples 1 to 4 and Comparative Examples 1 to 4 (Tables 19 to 22), are shown in Table 23 (Practical Examples 1 to 4) and Table 24 (Comparative Examples 1 to 4). In addition, the yields of furfural newly produced from xylose in the secondary hydrolysis step implemented in Comparative Examples 1 to 4 (relative to xylose) are shown in Table 24.

TABLE 23

| | Secondary hydrolysis conditions With circulation | Furfural yield (%: relative to raw material) Recovery from the gaseous phase in the flash tank |
| --- | --- | --- |
| Practical Example 1 | Temperature: 180° C., retention time: 10 minutes | 9.2 |
| Practical Example 2 | Temperature: 180° C., retention time: 20 minutes | 12.6 |
| Practical Example 3 | Temperature: 180° C., retention time: 30 minutes | 10.6 |
| Practical Example 4 | Temperature: 180° C., retention time: 40 minutes | 10.2 |

TABLE 24

| | Secondary hydrolysis conditions No circulation | Furfural yield (%: relative to raw material) Recovery from the gaseous phase in the flash tank | Yield of furfurals produced from xylose in secondary hydroylsis (%: relative to xylose) |
| --- | --- | --- | --- |
| Comparative Example 1 | Temperature: 180° C., retention time: 10 minutes | 6.4 | 43 |
| Comparative Example 2 | Temperature: 180° C., retention time: 20 minutes | 6.9 | 62 |
| Comparative Example 3 | Temperature: 180° C., retention time: 30 minutes | 7.5 | 48 |
| Comparative Example 4 | Temperature: 180° C., retention time: 40 minutes | 7.2 | 32 |

When the hydrolysis solution (liquid phase) separated by the flash tank of Comparative Examples 1 to 4 shown in Table 24 was not circulated to the secondary hydrolysis device R2, the furfural yield was highest at a retention time of 30 minutes (Comparative Example 3). On the other hand, when the hydrolysis solution separated by the flash tank of Practical Examples 1 to 4 shown in Table 23 was circulated to the secondary hydrolysis device R2, the furfural yield was highest at a retention time of 20 minutes (Practical Example 2). It was ascertained from the above results that when the hydrolysis solution separated by the flash tank is circulated to the secondary hydrolysis device R2, not only does the furfural yield improve in comparison to when the solution is not circulated, but it is also possible to reduce the retention time required to achieve a high furfural yield.

In addition, the yield of furfural produced from the raw material in the experiments of Comparative Examples 1 to 4 (without circulation) was highest at a retention time of 30 minutes, but the yield of furfural produced from xylose (relative to xylose) was highest at a retention time of 20 minutes. The above results suggested that furfural can be produced most efficiently by performing secondary hydrolysis with a retention time at which the yield of furfural produced from xylose is highest (20 minutes) and circulating the hydrolysis solution (containing oligosaccharides and monosaccharides) from which the vapor phase is removed by the flash tank to the secondary hydrolysis device R2.

Practical Example 5

Using the device illustrated in FIG. 11, primary hydrolysis was performed with the same method as in Production Example 40. Next, the primary hydrolysis solution was transferred to the secondary reaction vessel BR2, and hydrolysis was performed in the secondary reaction vessel BR2 under a pressure of 1.05 MPa and at 180° C. with a retention time of 10 minutes to obtain a secondary hydrolysis solution. The hydrolysis solution was continuously transferred from the secondary reaction vessel BR to the flash tank (manufactured by Shin-Ei Giken (Ltd.), volume: 4 L) without cooling the hydrolysis solution by opening the valve V of the secondary hydrolysis solution transfer conduit 11. A vapor phase separated by the flash tank (concentration/separation device F) was cooled by the condenser C, and a furfural aqueous solution (10 parts by mass/hour) was extracted from the furfural aqueous solution recovery conduit 4. On the other hand, an aqueous solution containing sugars or the like (120 parts by mass/hour) was extracted from the conduit 5 as a liquid phase inside the flash tank, and the solution was supplied to the supply port (conduit 3) of the secondary reaction vessel BR2 via the circulation conduit 14 for an aqueous solution containing sugars or the like and then continuously circulated. At the point when circulation to the secondary reaction vessel BR2 was begun, the feed rate of the primary hydrolysis solution from the continuous primary hydrolysis device R1 to the secondary reaction vessel BR2 was adjusted to 10 parts by mass/hour, and operation (steady state operation) was continuously maintained thereafter.

During steady state operation (30 minutes after circulation was begun), the content of total sugar, monosaccharides, oligosaccharides, and furfurals contained in each aqueous solution obtained from the flash tank was measured, and the yield of each component with respect to the raw material (dry mass) was calculated. The results are shown in Table 25.

Comparative Example 5

A test in which the aqueous solution containing sugars (liquid phase) separated by the flash tank in the method of Practical Example 5 was not circulated to the secondary reaction vessel BR was used as a Comparative Example 5. The results are shown in Table 25.

TABLE 25

| | Secondary hydrolysis conditions | | Yield (%: relative to raw material) Flash tank | |
|---|---|---|---|---|
| | | | Gas phase | Liquid phase |
| Practical Example 5 | Temperature: 180° C., retention time: 10 minutes With circulation (measured 30 minutes after circulation was begun) | Total sugar Monosaccharides Oligosaccharides Furfurals | 0 0 0 9.0 | 7.6 4.9 2.7 0.5 |
| Comparative Example 5 | Temperature: 180° C., retention time: 10 minutes No circulation | Total sugar Monosaccharides Oligosaccharides Furfurals | 0 0 0 6.1 | 9.6 6.2 3.4 0.5 |

It was ascertained from the results of Table 25 that when an aqueous solution containing a sugar solution separated by the flash tank is continuously circulated to the secondary reaction vessel BR2 (180° C., retention time: 10 minutes) (Practical Example 5), furfural can be recovered more efficiently than when the solution is not circulated to the secondary reaction vessel BR2 (Comparative Example 5).

Practical Example 6

Practical Example 6 was implemented with the same method as in Practical Example 5 with the exception that the retention time in the secondary reaction vessel BR2 was changed to 20 minutes. During steady state operation (60 minutes after circulation was begun), the content of total sugar, monosaccharides, oligosaccharides, and furfurals contained in each aqueous solution obtained from the flash tank was measured, and the yield of each component with respect to the raw material (dry mass) was calculated. The results are shown in Table 26.

Comparative Example 6

A test in which the aqueous solution containing sugars (liquid phase) separated by the flash tank in the method of Practical Example 6 was not circulated to the secondary reaction vessel BR2 was used as a Comparative Example 6. The results are shown in Table 26.

TABLE 26

| | Secondary hydrolysis conditions | | Yield (%: relative to raw material) Flash tank | |
|---|---|---|---|---|
| | | | Gas phase | Liquid phase |
| Practical Example 6 | Temperature: 180° C., retention time: 20 minutes With circulation (measured 60 minutes after circulation was begun) | Total sugar Monosaccharides Oligosaccharides Furfurals | 0 0 0 11.8 | 3.8 2.2 1.6 0.5 |

TABLE 26-continued

| | Secondary hydrolysis conditions | | Yield (%: relative to raw material) Flash tank | |
|---|---|---|---|---|
| | | | Gas phase | Liquid phase |
| Comparative Example 6 | Temperature: 180° C., retention time: 20 minutes No circulation | Total sugar Monosaccharides Oligosaccharides Furfurals | 0 0 0 6.2 | 9.8 6.4 3.4 0.5 |

It was ascertained from the results of Table 26 that when an aqueous solution containing a sugar solution separated by the flash tank is continuously circulated to the secondary reaction vessel BR2 (180° C., retention time: 20 minutes) (Practical Example 6), furfural can be recovered more efficiently than when the solution is not circulated to the secondary reaction vessel BR2 (Comparative Example 6).

Practical Example 7

Practical Example 7 was implemented with the same method as in Practical Example 5 with the exception that the retention time in the secondary reaction vessel BR2 was changed to 30 minutes. During steady state operation (90 minutes after circulation was begun), the content of total sugar, monosaccharides, oligosaccharides, and furfurals contained in each aqueous solution obtained from the flash tank was measured, and the yield of each component with respect to the raw material (dry mass) was calculated. The results are shown in Table 27.

Comparative Example 7

A test in which the aqueous solution containing sugars (liquid phase) separated by the flash tank in the method of Practical Example 7 was not circulated to the secondary reaction vessel BR2 was used as a Comparative Example 7. The results are shown in Table 27.

TABLE 27

| | Secondary hydrolysis conditions | | Yield (%: relative to raw material) Flash tank | |
|---|---|---|---|---|
| | | | Gas phase | Liquid phase |
| Practical Example 7 | Temperature: 180° C., retention time: 30 minutes With circulation (measured 120 minutes after circulation was begun) | Total sugar Monosaccharides Oligosaccharides Furfurals | 0 0 0 10.2 | 3.3 2.0 1.3 0.5 |
| Comparative Example 7 | Temperature: 180° C., retention time: 30 minutes No circulation | Total sugar Monosaccharides Oligosaccharides Furfurals | 0 0 0 7.0 | 9.9 6.5 3.4 0.5 |

It was ascertained that when an aqueous solution containing a sugar solution separated by the flash tank is continuously circulated to the secondary reaction vessel BR (180° C., retention time: 30 minutes) (Practical Example 7), furfural can be recovered more efficiently than when the solution is not circulated to the secondary reaction vessel BR (Comparative Example 7).

Practical Example 8

Practical Example 8 was implemented with the same method as in Practical Example 5 with the exception that the retention time in the secondary reaction vessel BR2 was changed to 40 minutes. During steady state operation (120 minutes after circulation was begun), the content of total sugar, monosaccharides, oligosaccharides, and furfurals contained in each aqueous solution obtained from the flash tank was measured, and the yield of each component with respect to the raw material (dry mass) was calculated. The results are shown in Table 28.

Comparative Example 8

A test in which the aqueous solution containing sugars (liquid phase) separated by the flash tank in the method of Practical Example 8 was not circulated to the secondary reaction vessel BR2 was used as a Comparative Example 8.

The results are shown in Table 28.

TABLE 28

|  | Secondary hydrolysis conditions |  | Yield (%: relative to raw material) | |
|---|---|---|---|---|
|  |  |  | Flash tank | |
|  |  |  | Gas phase | Liquid phase |
| Practical Example 8 | Temperature: 180° C., retention time: 40 minutes With circulation (measured 120 minutes after circulation was begun) | Total sugar Monosaccharides Oligosaccharides Furfurals | 0 0 0 9.7 | 2.9 1.7 1.2 0.5 |
| Comparative Example 8 | Temperature: 180° C., retention time: 40 minutes No circulation | Total sugar Monosaccharides Oligosaccharides Furfurals | 0 0 0 6.6 | 8.8 5.5 3.3 0.5 |

It was ascertained that when an aqueous solution containing a sugar solution separated by the flash tank is continuously circulated to the secondary reaction vessel BR2 (180° C., retention time: 40 minutes) (Practical Example 8), furfural can be recovered more efficiently than when the solution is not circulated to the secondary reaction vessel BR2 (Comparative Example 8). In addition, in a comparison of Practical Examples 5 to 8, the furfural yield was highest when the retention time of secondary hydrolysis was 20 minutes (Practical Example 5).

The yields (list) of furfurals recovered from the gaseous phased separated by the flash tank, as excerpted from the results of Practical Examples 5 to 8 and Comparative Examples 5 to 8 (Tables 25 to 28) are shown in Table 29 (Practical Examples 5 to 8) and Table 30 (Comparative Examples 5 to 8). In addition, the yields of furfural newly produced from xylose in the secondary reaction vessel BR implemented in Comparative Examples 5 to 8 (relative to xylose) are shown in Table 30.

TABLE 29

|  | Secondary hydrolysis conditions With circulation | Furfural yield (%: relative to raw material) Recovery from the gaseous phase in the flash tank |
|---|---|---|
| Practical Example 5 | Temperature: 180° C., retention time: 10 minutes | 9.0 |
| Practical Example 6 | Temperature: 180° C., retention time: 20 minutes | 11.8 |
| Practical Example 7 | Temperature: 180° C., retention time: 30 minutes | 10.2 |
| Practical Example 8 | Temperature: 180° C., retention time: 40 minutes | 9.7 |

TABLE 30

|  | Secondary hydrolysis conditions No circulation | Furfural yield (%: relative to raw material) Recovery from the gaseous phase in the flash tank | Yield of furfurals produced from xylose in secondary hydroylsis (%: relative to xylose) |
|---|---|---|---|
| Comparative Example 5 | Temperature: 180° C., retention time: 10 minutes | 6.1 | 41 |
| Comparative Example 6 | Temperature: 180° C., retention time: 20 minutes | 6.2 | 64 |
| Comparative Example 7 | Temperature: 180° C., retention time: 30 minutes | 7.0 | 47 |
| Comparative Example 8 | Temperature: 180° C., retention time: 40 minutes | 6.6 | 31 |

When the hydrolysis solution (liquid phase) separated by the flash tank of Comparative Examples 5 to 8 shown in Table 30 was not circulated to the secondary reaction vessel BR2, the furfural yield was highest at a retention time of 30 minutes (Comparative Example 7). On the other hand, when the hydrolysis solution separated by the flash tank of Practical Examples 5 to 8 shown in Table 21 was circulated to the secondary reaction vessel BR2, the furfural yield was highest at a retention time of 20 minutes (Practical Example 6). It was ascertained from the above results that when the hydrolysis solution separated by the flash tank is circulated to the secondary reaction vessel BR2, not only does the furfural yield improve in comparison to when the solution is not circulated, but it is also possible to reduce the retention time required to achieve a high furfural yield.

In addition, the yield of furfural produced from the raw material in the experiments of Comparative Examples 5 to 8 (without circulation) was highest at a retention time of 30 minutes, but the yield of furfural produced from xylose (relative to xylose) was highest at a retention time of 20 minutes. The above results suggest that a method of performing secondary hydrolysis with a retention time at which the yield of furfural produced from xylose is highest (20 minutes) and circulating the hydrolysis solution (containing oligosaccharides and monosaccharides) from which the vapor phase is removed by the flash tank to the secondary reaction vessel BR2 is the method with which furfural can be produced most efficiently in the manufacturing process.

Production Examples 93 to 103

A raw material suspension containing a raw material biomass was prepared by mixing *Eucalyptus pellita* chips (2 mm thick) and ion exchange water at a ratio of 5 parts by mass of ion exchange water per 1 part by mass of the chips (dry).

The raw material suspension was continuously supplied from the raw material suspension supply conduit 1 connected to the top supply port A of the continuous primary hydrolysis device R1 illustrated in FIG. 12 at a rate of 400 parts by mass/hour. The solution was hydrolyzed in the continuous primary hydrolysis device R1 at 170° C. and 0.79 MPa, and the suspension containing the hydrolyzed biomass was continuously discharged to the hydrolysis suspension discharge conduit 2 from the bottom discharge port B of the hydrolysis device by opening the decompression valve VP. The retention time in the hydrolysis device was set to three hours.

Washing water was supplied to the bottom of the device from the washing solution supply device W1 installed on the bottom side of the device via the washing solution supply conduit 6 at a rate of 400 parts by mass/hour, and the solution was brought into contact, in a countercurrent manner, with a hydrolysis suspension moving downward from the intermediate extraction port G1 in the center of the continuous primary hydrolysis device R1 provided with a stainless steel metal mesh having an opening size of 80 μm (solid-liquid separation device S1) in the center of the primary hydrolysis device.

Three hours after the supply of the raw material suspension was begun, the primary hydrolysis solution (260 parts by mass/hour) was extracted from the hydrolysis suspension via the intermediate extraction port G1 (at a position corresponding to a hydrolysis time of 1.5 hours) in a state in which the temperature and pressure inside the primary hydrolysis device were maintained by opening the decompression valve VP of the primary hydrolysis solution extraction conduit 3, and the solution was then transferred to the secondary reaction vessel BR2.

At the point when the liquid volume of the primary hydrolysis solution transferred to the secondary reaction vessel BR2 reached 100 L, the decompression valve VP (conduit 3) was closed so as to stop the supply of the primary hydrolysis solution from the continuous primary hydrolysis device R1. Sulfuric acid was added to the primary hydrolysis solution so that the sulfuric acid concentration in the hydrolysis solution was 0.3% (W/V), and the solution was then supplied to the secondary reaction vessel BR2.

Next, secondary hydrolysis (batch-type) was performed at 170° C. with the secondary reaction vessel BR2. The reaction time of secondary hydrolysis was set to 5 minutes (Production Example 93), 10 minutes (Production Example 94), 15 minutes (Production Example 95), 20 minutes (Production Example 96), 30 minutes (Production Example 97), 60 minutes (Production Example 98), 120 minutes (Production Example 99), 240 minutes (Production Example 100), 300 minutes (Production Example 101), 360 minutes (Production Example 102), and 480 minutes (Production Example 103).

After secondary hydrolysis, the secondary hydrolysis solution was extracted from the bottom of the secondary hydrolysis kettle BR2 by the secondary hydrolysis solution extraction conduit 11 and transferred to a flash tank (concentration/separation device F) [manufactured by Shin-Ei Giken (Ltd.), volume: 4 L]. A vapor phase separated by the flash tank F was fed to the condenser C by opening the valve 9 of the vapor phase transfer conduit 9, and after the solution was cooled, 9.2 L of a furfural aqueous solution was extracted from the condensate extraction conduit 4.

The content of furfurals contained in the furfural aqueous solution was measured with the method described below, and the yield of furfurals with respect to the raw material (dry mass) was calculated.

Figure 13:
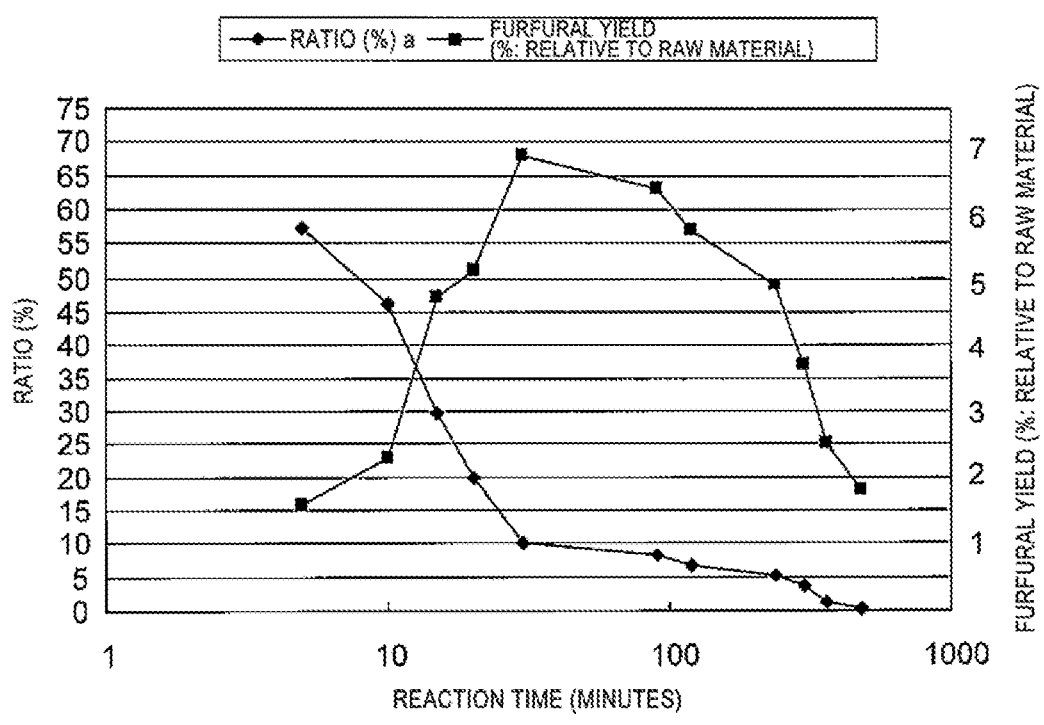
FIG. 13 illustrates the relationship between the secondary hydrolysis conditions and the furfural yield.

In addition, the concentrations of pentoses contained in the hydrolysis solution before and after secondary hydrolysis were measured, and the ratio (%) of the mass of all pentoses contained in the hydrolysis solution after secondary hydrolysis with respect to the mass of all pentoses contained in the hydrolysis solution before secondary hydrolysis was calculated in accordance with the formula described above. The results are illustrated in FIG. 13.

<Measurement of the Mass of all Pentoses>

The solution supplied to the secondary hydrolysis device and the secondary hydrolysis solution after secondary hydrolysis were used as sample solutions, and sulfuric acid was added to each sample solution so that the final concentration was 4 mass %. After hydrolysis was performed for one hour at 120° C., sugar analysis was performed. The content of each pentose (monosaccharide) in each sample solution was calculated, and the total value was used as the mass of all pentoses in each sample solution.

<Sugar Analysis>

Sugar analysis was performed using a sugar analysis system (ICS5000) manufactured by DIONEX. Using a CArBopAk PA-1 (20×250 mm) as a column and a 20 mM NaOH solution as an eluant, monosaccharides were eluted at a flow rate of 0.25 ml/min. A pulsed amperometric detector was used for detection. Arabinose and xylose were used as a standard monosaccharide (pentose) preparation. A calibration curve was created for each of these components, and the content of each monosaccharide in each sample solution was determined.

<Oligosaccharide Content>

A value determined by subtracting the content calculated by sugar analysis with the sugar analysis system from the content calculated after performing hydrolysis with 4 mass % sulfuric acid was used as the oligosaccharide (pentose) content in each sample solution.

<Quantiative Determination of Furfurals>

An HPLC system manufactured by Agilent Technologies was used for the quantitative determination of furfurals. Using an Aminex HPX87P (7.8×300 mm) manufactured by Bio-Rad as a column and a 5 mM sulfuric acid solution as an eluant, furfurals were eluted at a flow rate of 1 ml/min. A UV-Vis detector was used for detection. Furfural was used as a standard furfural preparation, and a calibration curve was created to determine the content in the sample.

The furfural yield was high in tests (Production Examples 95 to 100) in which secondary hydrolysis was performed under reaction conditions under which the ratio % of the mass of all pentoses contained in the hydrolysis solution after secondary hydrolysis with respect to the mass of all pentoses contained in the hydrolysis solution before secondary hydrolysis [(after secondary hydrolysis/before secondary hydrolysis)×100] was from 5.1 to 29.7%. It was inferred from the above results that the production of furfurals from sugars contained in the hydrolysis solution progresses (the total amount of sugar contained in the hydrolysis solution decreases) as secondary hydrolysis is performed for longer periods of time, but the yield of furfurals decreases due to the progression of side reactions between furfurals and side reactions between sugars and furfurals.

Production Examples 104 to 114

Primary hydrolysis was performed with the same method as in Production Example 93 using the device illustrated in FIG. 12. A primary hydrolysis solution (260 parts by mass/hour) was continuously extracted by opening the decompression valve VP of the primary hydrolysis solution extraction conduit 3, and the solution was then transferred to the secondary reaction vessel BR2. Sulfuric acid was automatically added to the primary hydrolysis solution so that the sulfuric acid concentration was 0.3% (W/V). Secondary hydrolysis was continuously performed with the secondary reaction vessel BR2 at 170° C. The retention time of secondary hydrolysis (secondary reaction vessel BR2) was set to 5 minutes (Production Example 104), 10 minutes (Production Example 105), 15 minutes (Production Example 106), 20 minutes (Production Example 107), 30 minutes (Production Example 108), 60 minutes (Production Example 109), 120 minutes (Production Example 110), 240 minutes (Production Example 111), 300 minutes (Production Example 112), 360 minutes (Production Example 113), and 480 minutes (Production Example 114).

The secondary hydrolysis solution (260 parts by mass/hour) after secondary hydrolysis was continuously transferred to the flash tank (concentration/separation device F) from the conduit 11 of the secondary reaction vessel BR2, and the hydrolysis solution was separated into a vapor phase and a liquid phase by the flash tank. The vapor phase of the flash tank was extracted to the conduit 9 and passed through the condenser C so as to be cooled to 20° C., and a furfural aqueous solution (20 parts by mass/hour) was extracted from the condensate extraction conduit 4. In addition, an aqueous solution containing sugars or the like (240 parts by mass/hour) was extracted from the conduit 5 as a liquid phase in the flash tank. The content of furfurals contained in the furfural aqueous solution was measured, and the yield of furfurals with respect to the raw material (dry mass) was calculated.

Figure 14:
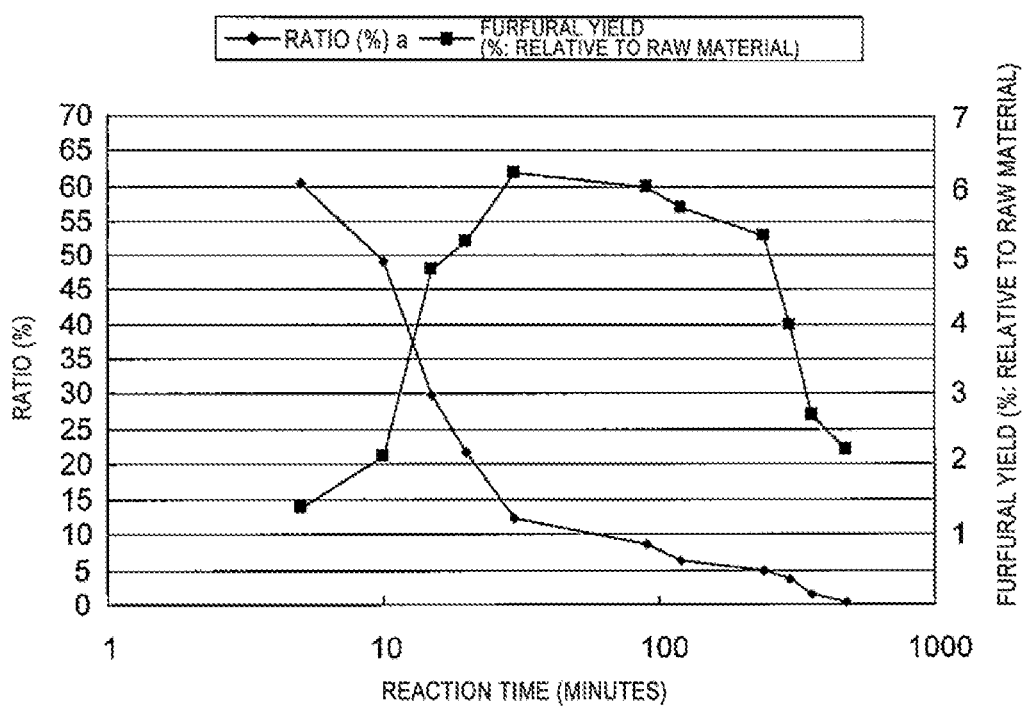
FIG. 14 illustrates the relationship between the secondary hydrolysis conditions and the furfural yield.

In addition, the pentose concentration of the hydrolysis solution supplied to the secondary reaction vessel BR2 (hydrolysis solution of the conduit 3) and the pentose concentration contained in the hydrolysis solution discharged from the secondary reaction vessel BR2 (hydrolysis solution of conduit 11) were measured, and the ratio % of the mass of pentoses contained in the hydrolysis solution after secondary hydrolysis with respect to the mass of pentoses contained in the hydrolysis solution before secondary hydrolysis [(after secondary hydrolysis)/(before secondary hydrolysis)×100] was calculated. The results are illustrated in FIG. 14.

The furfural yield was high in tests (Production Examples 106 to 111) in which secondary hydrolysis was performed under reaction conditions under which the ratio % of the mass of pentoses contained in the hydrolysis solution after secondary hydrolysis with respect to the mass of all pentoses contained in the hydrolysis solution before secondary hydrolysis [(after secondary hydrolysis/before secondary hydrolysis)×100] was from 5.0 to 29.9%.

It was inferred from the above results that the production of furfurals from sugars contained in the hydrolysis solution progresses (the total amount of sugar contained in the hydrolysis solution decreases) as the retention time of secondary hydrolysis is lengthened, but the yield of furfurals decreases due to the progression of side reactions between furfurals and side reactions between sugars and furfurals.

Production Example 115

Part (80 parts by mass/hour) of the aqueous solution containing sugars or the like (240 parts by mass/hour) extracted from the conduit 5 as a liquid phase in the flash tank in Production Example 108 was circulated to the conduit 1 at the top of the primary hydrolysis device via the conduit 8. The content of furfurals contained in the furfural aqueous solution recovered from the vapor phased separated by the flash tank at the point when the continuous operation reached a steady state was measured, and the yield of furfurals with respect to the raw material (dry mass) was calculated. A test (Production Example 108) in which the aqueous solution containing sugars or the like was not circulated was used as a comparative example. The results are shown in Table 31.

TABLE 31

| | Circulation of the liquid phase separated by the concentration/separation device (conduit 23) | Yield (%: relative to raw material) Furfurals |
| --- | --- | --- |
| Production Example 115 | With circulation | 8.1 |
| Production Example 108 | No circulation | 6.2 |

Production Examples 116 to 126

With the same methods as in Production Examples 104 to 114 using the device illustrated in FIG. 12, secondary hydrolysis tests were performed without adding sulfuric acid to the primary hydrolysis solution. Secondary hydrolysis was continuously performed with the secondary reaction vessel BR2 at 170° C. The retention time of secondary hydrolysis (secondary reaction vessel BR2) was set to 5 minutes (Production Example 116), 10 minutes (Production Example 117), 15 minutes (Production Example 118), 20 minutes (Production Example 119), 30 minutes (Production Example 120), 60 minutes (Production Example 121), 120 minutes (Production Example 122), 240 minutes (Production Example 123), 300 minutes (Production Example 124), 360 minutes (Production Example 125), and 480 minutes (Production Example 126).

Figure 15:
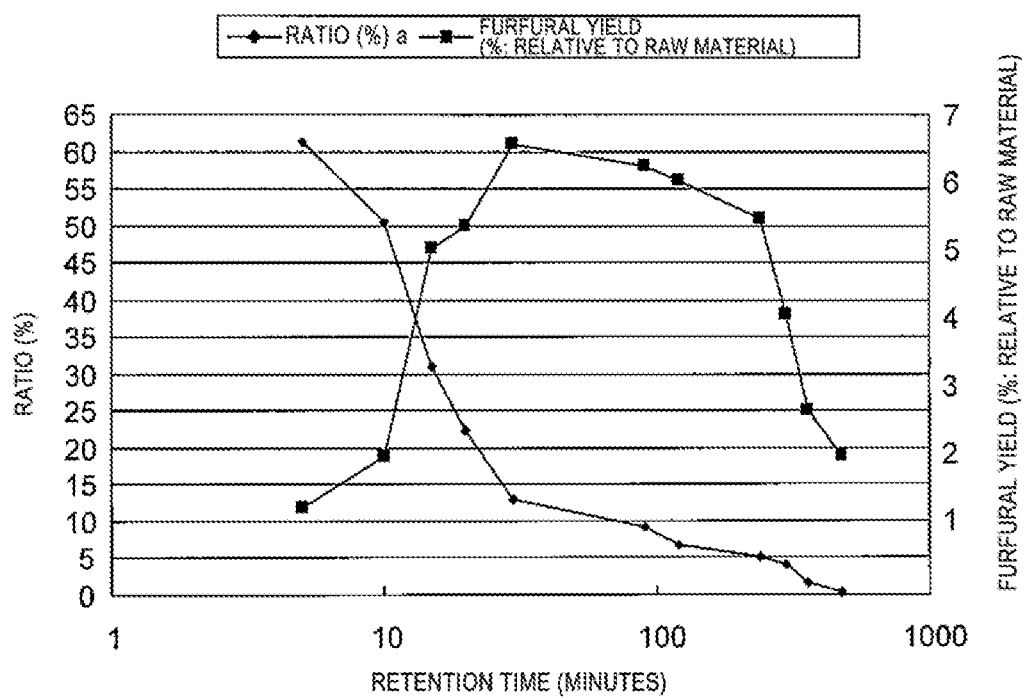
FIG. 15 illustrates the relationship between the secondary hydrolysis conditions and the furfural yield.

All other operations were performed with the same methods as in Production Examples 104 to 114. The results are illustrated in FIG. 15.

The furfural yield was high in tests (Production Examples 116 to 123) in which secondary hydrolysis was performed under reaction conditions under which the ratio % of the mass of pentoses contained in the hydrolysis solution after secondary hydrolysis with respect to the mass of all pentoses contained in the hydrolysis solution before secondary hydrolysis [(after secondary hydrolysis/before secondary hydrolysis)×100] was from 5.1 to 30.0%. It was inferred from the above results that the production of furfurals from sugars contained in the hydrolysis solution progresses (the total amount of sugar contained in the hydrolysis solution decreases) as the retention time of secondary hydrolysis is lengthened, but the yield of furfurals decreases due to the progression of side reactions between furfurals and side reactions between sugars and furfurals.

Practical Examples 9 to 13

A raw material suspension containing a raw material biomass was prepared by mixing *Eucalyptus pellita* chips (2 mm thick) and ion exchange water at a ratio of 5 parts by mass of ion exchange water per 1 part by mass of the chips (dry).

The raw material suspension was continuously supplied from the raw material suspension supply conduit 1 connected to the top supply port A of the continuous primary hydrolysis device R1 illustrated in FIG. 16 at a rate of 400 parts by mass/hour. The solution was hydrolyzed in the continuous primary hydrolysis device R1 at 170° C. and 0.79 MPa, and the suspension containing the hydrolyzed raw material was continuously discharged to the hydrolysis suspension discharge conduit 2 from the bottom discharge port B of the hydrolysis device by opening the decompression valve VP. The retention time in the hydrolysis device was set to three hours.

In addition, washing water was supplied from the countercurrent washing solution supply device W1 at the bottom side of the device via the washing solution supply conduit 6 at a rate of 400 parts by mass/hour, and the solution was brought into contact, in a countercurrent manner, with a hydrolysis suspension moving downward from the intermediate extraction port G1 in the center of the continuous primary hydrolysis device R1 provided with a stainless steel metal mesh having an opening size of 80 μm (solid-liquid separation device S1) in the center of the hydrolysis device.

Three hours after the supply of the raw material suspension was begun, the primary hydrolysis solution (260 parts by mass/hour) was extracted from the hydrolysis suspension via the intermediate extraction port G1 (at a position corresponding to a hydrolysis time of 1.5 hours) in a state in which the temperature and pressure inside the hydrolysis device were maintained by opening the valve V of the primary hydrolysis solution extraction conduit 3, and the solution was then transferred to the secondary reaction vessel BR2.

At the point when the liquid volume of the primary hydrolysis solution transferred to the secondary reaction vessel BR2 reached 100 L, the valve V (conduit 3) was closed so as to stop the transfer of the primary hydrolysis solution from the continuous primary hydrolysis device R1. However, in an experiment in which the pressure inside the primary hydrolysis device was higher than the pressure inside the secondary hydrolysis device, the primary hydrolysis solution was extracted using the decompression valve VP instead of the valve V (not illustrated). Sulfuric acid was added to the primary hydrolysis solution transferred to the secondary reaction vessel BR2 so that the sulfuric acid concentration was 0.3% (W/V).

Next, the primary hydrolysis solution to which sulfuric acid was added as described above was subjected to secondary hydrolysis by the secondary reaction vessel BR2 at 200° C. The reaction time of secondary hydrolysis was set to 10 minutes (Practical Example 9), 30 minutes (Practical Example 10), 60 minutes (Practical Example 11), 120 minutes (Practical Example 12), and 180 minutes (Practical Example 13). After secondary hydrolysis, the vapor phase was extracted by opening the valve V of the vapor phase transfer conduit 21 connected to the secondary reaction vessel BR2, and the vapor phase was then cooled to 100° C. by the condenser C and extracted to the condensate extraction conduit 4 as a condensate (aqueous solution containing furfurals). The extracted condensate was fed to the distillation device EV and concentrated, and a concentrate (20° C.) containing furfurals was recovered from the recovery conduit 25 for the furfural concentrate. The content of furfurals contained in the recovered furfural concentrate was measured with the same method as in Production Example 1, and the yield of furfurals with respect to the raw material (dry mass) was calculated.

In addition, the energy required for the distillation necessary to recover 1 kg of furfural (MJ/furfural-kg) and the time required for the distillation of furfurals (minutes/furfural-kg) were measured.

Further, the liquid phase from which the vapor phase was removed was extracted from the liquid phase extraction conduit 11 at the bottom of the secondary reaction vessel BR2. The monosaccharides and oligosaccharides contained in the liquid phase were measured with the same method as in Production Example 1, and the yield of monosaccharides and oligosaccharides with respect to the raw material (dry mass) was calculated. The results are shown in Table 32.

Comparative Examples 9 to 13

Figure 17:
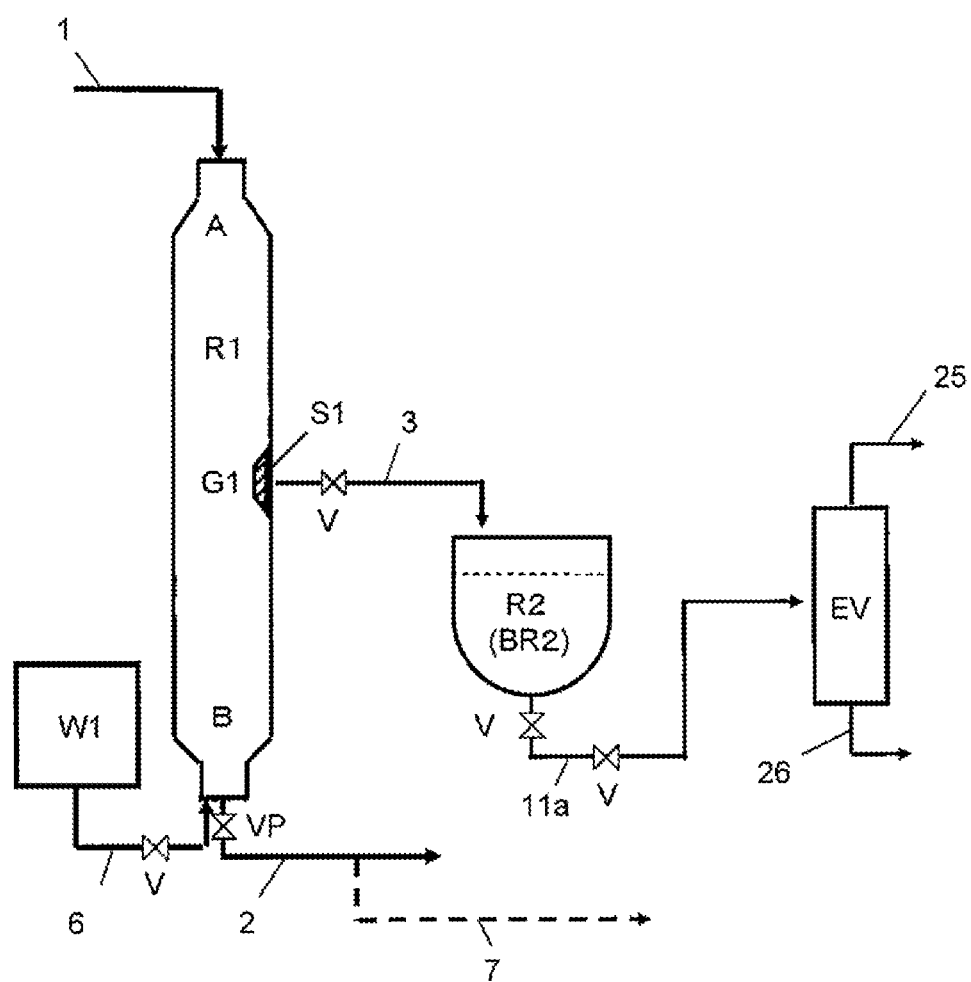
FIG. 17 illustrates a device for implementing a method of a comparative example differing from the device for implementing the method of the present invention.

Using the device illustrated in FIG. 17, primary hydrolysis and secondary hydrolysis were performed with the same method as in Practical Example 9. The reaction time of secondary hydrolysis was set to 10 minutes (Comparative Example 9), 30 minutes (Comparative Example 10), 60 minutes (Comparative Example 11), 120 minutes (Comparative Example 12), and 180 minutes (Comparative Example 13).

After secondary hydrolysis, the entire volume of secondary hydrolysates in the secondary reaction vessel BR2 was extracted and transferred to the distillation device EV by opening the valve V of a secondary hydrolysis solution extraction conduit 11a once the pressure inside the secondary hydrolysis device (secondary reaction vessel BR2) reached normal pressure. The solution was distilled and separated by the distillation device EV, and a concentrate containing furfurals was recovered from the concentrate recovery conduit 25 for the concentrate containing furfurals. On the other hand, an aqueous solution containing monosaccharides and oligosaccharides was recovered from a recovery conduit 26 for an aqueous solution containing sugars or the like.

The content of furfurals contained in the concentrate containing furfurals was measured with the same method as in Practical Example 9, and the yield of furfurals with respect to the raw material (dry mass) was calculated. In addition, the energy required for the distillation necessary to recover 1 kg of furfural (MJ/furfural-kg) and the time required for the distillation of furfurals (minutes/furfural-kg) were measured. Further, the monosaccharides and oligosaccharides contained in the aqueous solution recovered from the recovery conduit 26 for the aqueous solution containing sugars or the like of the distillation device EV were measured with the same method as in Practical Example 1, and the yield of monosaccharides and oligosaccharides with respect to the raw material (dry mass) was calculated. The results are shown in Table 32.

TABLE 32

|  | Secondary hydrolysis conditions (batch-type) | Yield (%: relative to raw material) | | | Energy consumed (MJ/furfural-kg) | Distillation time (minutes/furfural-kg) |
| --- | --- | --- | --- | --- | --- | --- |
|  | 200° C. | Furfurals | Monosaccharides | Oligosaccharides | | |
| Practical Example 9 | 10 minutes | 5.5 | 4.2 | 1.5 | 80.2 | 13.6 |
| Practical Example 10 | 30 minutes | 6.5 | 4.0 | 1.2 | 80.6 | 13.1 |
| Practical Example 11 | 60 minutes | 6.8 | 3.6 | 0.9 | 80.0 | 12.5 |
| Practical Example 12 | 120 minutes | 7.3 | 2.8 | 0.6 | 79.5 | 12.0 |
| Practical Example 13 | 180 minutes | 7.5 | 2.4 | 0.1 | 80.4 | 11.6 |
| Comparative Example 9 | 10 minutes | 5.4 | 4.0 | 1.5 | 102.4 | 17.2 |
| Comparative Example 10 | 30 minutes | 6.3 | 3.8 | 1.1 | 101.5 | 16.8 |
| Comparative Example 11 | 60 minutes | 6.5 | 3.5 | 1.0 | 100.8 | 16.3 |
| Comparative Example 12 | 120 minutes | 7.0 | 2.4 | 0.6 | 101.8 | 15.7 |
| Comparative Example 13 | 180 minutes | 7.1 | 2.1 | 0.1 | 102.2 | 15.3 |

With the methods of Practical Examples 9 to 13 of performing secondary hydrolysis (200° C.) with the batch-type secondary hydrolysis device (secondary reaction vessel BR2), recovering furfurals with the distillation device from the vapor phase extracted from the secondary reaction vessel BR2 after secondary hydrolysis, and recovering monosaccharides and oligosaccharides from the liquid phase extracted from the secondary reaction vessel BR2, it was possible to reduce the energy required for distillation in comparison to the methods of Comparative Examples 9 to 13 of feeding the entire volume of the secondary hydrolysis solution in the secondary reaction vessel after secondary hydrolysis directly to the distillation device and separating and recovering furfurals, monosaccharides, and oligosaccharides. In addition, it was possible to reduce the time required for the concentration of furfurals by the distillation device since the amount of the vapor phase containing furfurals can be reduced. It was ascertained from the above results that the methods of Practical Examples 9 to 13 enable the efficient production of monosaccharides, oligosaccharides, and furfurals.

Practical Examples 14 to 18

Secondary hydrolysis was performed in Practical Example 9 with the secondary reaction vessel BR2 at 170° C. using reaction times of 10 minutes (Practical Example 14), 30 minutes (Practical Example 15), 60 minutes (Practical Example 16), 120 minutes (Practical Example 17), and 180 minutes (Practical Example 18). Other operations were performed with the same methods as in Practical Example 9. The results are shown in Table 33.

Comparative Examples 14 to 18

Secondary hydrolysis was performed in Comparative Example 9 with the secondary reaction vessel BR2 at 170° C. using reaction times of 10 minutes (Comparative Example 14), 30 minutes (Comparative Example 15), 60 minutes (Comparative Example 16), 120 minutes (Comparative Example 17), and 180 minutes (Comparative Example 18). Other operations were performed with the same methods as in Comparative Example 9. The results are shown in Table 33.

TABLE 33

|  | Secondary hydrolysis conditions (batch-type) | Yield (%: relative to raw material) | | | Energy consumed (MJ/furfural-kg) | Distillation time (minutes/furfural-kg) |
| --- | --- | --- | --- | --- | --- | --- |
|  | 170° C. | Furfurals | Monosaccharides | Oligosaccharides | | |
| Practical Example 14 | 10 minutes | 5.0 | 4.6 | 2.0 | 81.4 | 13.5 |
| Practical Example 15 | 30 minutes | 6.1 | 4.3 | 1.7 | 80.6 | 13.2 |
| Practical Example 16 | 60 minutes | 6.5 | 4.0 | 1.2 | 79.4 | 12.4 |
| Practical Example 17 | 120 minutes | 6.9 | 3.1 | 0.8 | 80.5 | 11.8 |
| Practical Example 18 | 180 minutes | 7.2 | 2.8 | 0.5 | 79.6 | 11.5 |
| Comparative Example 14 | 10 minutes | 4.8 | 4.3 | 2.1 | 103.2 | 17.4 |

TABLE 33-continued

|  | Secondary hydrolysis conditions (batch-type) 170° C. | Yield (%: relative to raw material) | | | Energy consumed (MJ/furfural-kg) | Distillation time (minutes/ furfural-kg) |
| --- | --- | --- | --- | --- | --- | --- |
|  |  | Furfurals | Monosaccharides | Oligosaccharides |  |  |
| Comparative Example 15 | 30 minutes | 5.9 | 4.0 | 1.7 | 101.6 | 17.0 |
| Comparative Example 16 | 60 minutes | 6.3 | 3.6 | 1.1 | 101.7 | 16.7 |
| Comparative Example 17 | 120 minutes | 6.3 | 2.8 | 0.7 | 103.5 | 16.0 |
| Comparative Example 18 | 180 minutes | 7.0 | 2.5 | 0.5 | 103.1 | 15.8 |

With the methods of Practical Examples 14 to 18 of performing secondary hydrolysis (170° C.) with the batch-type secondary hydrolysis device (secondary reaction vessel BR2), recovering furfurals with the distillation device from the vapor phase extracted from the secondary reaction vessel BR2, and recovering monosaccharides and oligosaccharides from the liquid phase extracted from the secondary reaction vessel BR2, it was possible to reduce the energy required for distillation in comparison to the methods of Comparative Examples 14 to 18 of feeding the entire volume of the hydrolysates in the secondary reaction vessel BR2 directly to the distillation device and separating and recovering furfurals, monosaccharides, and oligosaccharides. In addition, it was possible to reduce the time required for the concentration of furfurals by the distillation device since the amount of the aqueous containing furfurals can be reduced.

Practical Examples 19 to 23

Secondary hydrolysis was performed in Practical Example 9 with the secondary reaction vessel BR2 at 140° C. using reaction times of 10 minutes (Practical Example 19), 30 minutes (Practical Example 20), 60 minutes (Practical Example 21), 120 minutes (Practical Example 22), and 180 minutes (Practical Example 23). Other operations were performed with the same methods as in Practical Example 9. The results are shown in Table 34.

Comparative Examples 19 to 23

Secondary hydrolysis was performed in Comparative Example 9 with the secondary reaction vessel BR2 at 140° C. using reaction times of 10 minutes (Comparative Example 19), 30 minutes (Comparative Example 20), 60 minutes (Comparative Example 21), 120 minutes (Comparative Example 22), and 180 minutes (Comparative Example 23). Other operations were performed with the same methods as in Comparative Example 9. The results are shown in Table 34.

TABLE 34

|  | Secondary hydrolysis conditions (batch-type) 140° C. | Yield (%: relative to raw material) | | | Energy consumed (MJ/furfural-kg) | Distillation time (minutes/ furfural-kg) |
| --- | --- | --- | --- | --- | --- | --- |
|  |  | Furfurals | Monosaccharides | Oligosaccharides |  |  |
| Practical Example 19 | 10 minutes | 4.8 | 4.8 | 2.6 | 78.6 | 13.8 |
| Practical Example 20 | 30 minutes | 5.8 | 4.6 | 2.3 | 79.5 | 13.5 |
| Practical Example 21 | 60 minutes | 6.1 | 4.3 | 1.9 | 80.3 | 12.8 |
| Practical Example 22 | 120 minutes | 6.6 | 3.9 | 1.5 | 80.7 | 12.3 |
| Practical Example 23 | 180 minutes | 6.9 | 3.6 | 1.2 | 79.8 | 12.0 |
| Comparative Example 19 | 10 minutes | 4.6 | 4.5 | 2.5 | 102.2 | 17.9 |
| Comparative Example 20 | 30 minutes | 5.7 | 4.3 | 2.3 | 103.5 | 17.6 |
| Comparative Example 21 | 60 minutes | 6.0 | 4.0 | 1.8 | 102.1 | 17.1 |
| Comparative Example 22 | 120 minutes | 6.6 | 3.7 | 1.5 | 101.7 | 16.6 |
| Comparative Example 23 | 180 minutes | 6.7 | 3.3 | 1.0 | 101.9 | 16.2 |

With the methods of Practical Examples 19 to 23 of performing secondary hydrolysis (140° C.) with the batch-type secondary hydrolysis device (secondary reaction vessel BR2), recovering furfurals with the distillation device from the vapor phase extracted from the secondary reaction vessel BR2, and recovering monosaccharides and oligosaccharides from the liquid phase extracted from the secondary reaction vessel BR2, it was possible to reduce the energy required for distillation in comparison to the methods of Comparative Examples 19 to 23 of feeding the entire volume of the secondary hydrolysates in the secondary reaction vessel BR2 after secondary hydrolysis directly to the distillation device and separating and recovering furfurals, monosaccharides, and oligosaccharides. In addition, it was possible to reduce the time required for the concentration of furfurals by the distillation device since the amount of the aqueous solution containing furfurals can be reduced.

Practical Examples 24 to 28

Primary hydrolysis was performed with the same method as in Practical Example 9 using the device illustrated in FIG. 16. A primary hydrolysis solution (260 parts by mass/hour) was continuously extracted by opening the valve V of the primary hydrolysis solution extraction conduit 3, and the solution was then transferred to the secondary reaction vessel BR2. Secondary hydrolysis was continuously performed with the secondary reaction vessel BR2 at 170° C. The retention time of secondary hydrolysis (secondary reaction vessel BR2) was set to 10 minutes (Practical Example 24), 30 minutes (Practical Example 25), 60 minutes (Practical Example 26), 120 minutes (Practical Example 27), and 180 minutes (Practical Example 28). After secondary hydrolysis was begun, the vapor phase was continuously extracted by opening the valve (decompression valve) of the vapor phase transfer conduit 21 connected to the secondary reaction vessel BR2. The extracted vapor phase was cooled to 100° C. by the condenser C, and a condensate (aqueous solution containing furfurals) was extracted from the condensate extraction conduit 4. The condensate was concentrated by the distillation device EV, and a concentrate containing furfurals was recovered from the furfural concentrate recovery conduit 25.

The content of furfurals contained in the furfural concentrate was measured with the method described below, and the yield of furfurals with respect to the raw material (dry mass) was calculated. In addition, the energy required for the distillation necessary to recover 1 kg of furfural (MJ/furfural-kg) and the time required for the distillation of furfurals (minutes/furfural-kg) were measured.

Further, liquid phase of the secondary reaction vessel was continuously extracted from the liquid phase extraction conduit 11 at the bottom of the secondary reaction vessel BR2. The monosaccharides and oligosaccharides contained in the liquid phase of the secondary reaction vessel were measured with the same method as in Production Example 1, and the yield of monosaccharides and oligosaccharides with respect to the raw material (dry mass) was calculated. The results are shown in Table 35.

Comparative Examples 24 to 28

Primary hydrolysis and secondary hydrolysis were performed with the same method as in Practical Example 24 using the device illustrated in FIG. 17. The reaction time of secondary hydrolysis was set to 10 minutes (Comparative Example 24), 30 minutes (Comparative Example 25), 60 minutes (Comparative Example 26), 120 minutes (Comparative Example 27), and 180 minutes (Comparative Example 28).

After secondary hydrolysis was begun, the secondary hydrolysis solution was continuously transferred to the distillation device EV by opening the valve (decompression valve) of the conduit 11a connected to the secondary reaction vessel BR2. The solution was concentrated by the distillation device EV, and a furfural concentrate was recovered from the furfural concentrate recovery conduit 25.

The content of furfurals contained in the furfural concentrate was measured, and the yield of furfurals with respect to the raw material (dry mass) was calculated. In addition, the energy required for the distillation necessary to recover 1 kg of furfural (MJ/furfural-kg) was measured. Further, the monosaccharides and oligosaccharides contained in the aqueous solution recovered from the conduit 26 of the distillation device EV were measured with the same method as in Practical Example 1, and the yield of monosaccharides and oligosaccharides with respect to the raw material (dry mass) was calculated.

The results are shown in Table 35.

TABLE 35

| | Secondary hydrolysis conditions (continuous) | Yield (%: relative to raw material) | | | Energy consumed | Distillation time (minutes/ |
|---|---|---|---|---|---|---|
| | 170° C. | Furfurals | Monosaccharides | Oligosaccharides | (MJ/furfural-kg) | furfural-kg) |
| Practical Example 24 | 10 minutes | 5.4 | 4.5 | 1.9 | 81.2 | 13.3 |
| Practical Example 25 | 30 minutes | 6.5 | 4.2 | 1.7 | 80.8 | 13.0 |
| Practical Example 26 | 60 minutes | 6.9 | 4.0 | 1.1 | 80.6 | 12.1 |
| Practical Example 27 | 120 minutes | 7.3 | 3.0 | 0.7 | 79.8 | 11.4 |
| Practical Example 28 | 180 minutes | 7.7 | 2.8 | 0.5 | 79.5 | 11.2 |
| Comparative Example 24 | 10 minutes | 5.2 | 4.2 | 2.0 | 102.5 | 17.6 |
| Comparative Example 25 | 30 minutes | 6.2 | 4.0 | 1.7 | 101.9 | 17.2 |
| Comparative Example 26 | 60 minutes | 6.5 | 3.5 | 1.0 | 102.1 | 16.9 |

TABLE 35-continued

| | Secondary hydrolysis conditions (continuous) 170° C. | Yield (%: relative to raw material) | | | Energy consumed (MJ/furfural-kg) | Distillation time (minutes/ furfural-kg) |
|---|---|---|---|---|---|---|
| | | Furfurals | Monosaccharides | Oligosaccharides | | |
| Comparative Example 27 | 120 minutes | 6.9 | 2.7 | 0.6 | 102.7 | 16.6 |
| Comparative Example 28 | 180 minutes | 7.2 | 2.4 | 0.4 | 103.0 | 16.0 |

With the methods of Practical Examples 24 to 28 of performing secondary hydrolysis (170° C.) with the continuous secondary hydrolysis device (secondary reaction vessel BR2), recovering furfurals with the distillation device from the vapor phase continuously extracted from the secondary reaction vessel BR2, and recovering monosaccharides and oligosaccharides from the liquid phase extracted from the secondary reaction vessel BR2, it was possible to reduce the energy required for distillation in comparison to the methods of Comparative Examples 24 to 28 of performing secondary hydrolysis (170° C.) with the continuous secondary hydrolysis device (secondary reaction vessel BR2) and continuously separating and recovering furfurals (gaseous phase) and monosaccharides and oligosaccharides (liquid phase) from the secondary hydrolysis solution with the distillation device. In addition, it was possible to reduce the time required for the concentration of furfurals by the distillation device since the volume of the aqueous solution containing furfurals can be reduced.

Further, in Practical Examples 24 to 28, side reactions between sugars (monosaccharides and oligosaccharides) and furfurals contained in the hydrolysis solution were controlled by continuously removing the furfurals (vapor phase) from the secondary reaction vessel BR2 in secondary hydrolysis, and it is inferred that the yield of furfurals improved as a result of the acceleration of the production of furfurals from monosaccharides and oligosaccharides.

Practical Example 29

Practical Example 29 was implemented with the same method as in Practical Example 25 using the device illustrated in FIG. 18. However, after secondary hydrolysis was begun, the liquid phase was continuously extracted from the secondary reaction vessel BR2 by opening the valve (decompression valve) of the conduit 11 of the secondary reaction vessel BR2, and part of the liquid phase (100 parts by mass/hour) was continuously circulated and supplied to the primary hydrolysis solution (conduit 3) supplied to the secondary reaction vessel BR2 via the conduit 24. All other operations were performed with the same methods as in Practical Example 25. The results are shown in Table 36.

Comparative Example 29

A test in which the liquid phase extracted from the secondary reaction vessel in Practical Example 29 was not circulated was performed and used as a Comparative Example 29 (same as Practical Example 25). The results are shown in Table 36.

TABLE 36

| | Secondary hydrolysis conditions (continuous) 170° C., 30 minutes | Yield (%: relative to raw material) | | | Energy consumed (MJ/furfural-kg) | Distillation time (minutes/ furfural-kg) |
|---|---|---|---|---|---|---|
| | | Furfurals | Monosaccharides | Oligosaccharides | | |
| Practical Example 29 | With circulation | 7.3 | 3.8 | 1.2 | 79.4 | 12.5 |
| Comparative Example 29 | No circulation | 6.5 | 4.2 | 1.7 | 80.8 | 13.0 |

In the test in which the liquid phase extracted to the conduit 11 from the secondary reaction vessel BR2 was continuously circulated (Practical Example 29), the yield of furfurals improved in comparison to the test in which the secondary hydrolysis solution was not circulated (Comparative Example 29).

Production Example 127

A raw material (raw material suspension) was prepared by mixing *Eucalyptus pellita* chips (2 mm thick) and ion exchange water at a ratio of 5 parts by mass of ion exchange water per 1 part by mass of the chips (dry).

The raw material suspension was continuously supplied from the raw material suspension supply conduit 1 connected to the top part A of the continuous primary hydrolysis device R1 illustrated in FIG. 19 at a rate of 300 parts by mass/hour. The solution was hydrolyzed in the primary hydrolysis device at 165° C. and 0.70 MPa, and the hydrolyzed hydrolysis suspension was discharged to the discharge conduit 2 from the bottom part B of the hydrolysis device via the decompression valve VP. The retention time in the primary hydrolysis device was set to 100 minutes.

On the other hand, washing water was supplied from the washing solution supply device W1 to the bottom of the continuous primary hydrolysis device R1 at a rate of 200 parts by mass/hour by opening the valve V4 of the washing solution supply conduit 6, and the solution was brought into contact, in a countercurrent manner, with a hydrolysis suspension moving downward through the intermediate extraction port G1 of the continuous primary hydrolysis device R1 provided with a stainless steel metal mesh having an opening size of 300 μm.

Three hours after the supply of the raw material was begun (after steady state operation was begun), a hydrolysis solution 1 (200 parts by mass/hour) was extracted from the intermediate extraction port G1 (at a position corresponding to a hydrolysis time of 50 minutes) of the primary hydrolysis device in a state in which the temperature and pressure inside the primary hydrolysis device were maintained by opening the valve V1 of the hydrolysis solution extraction conduit 3.

The hydrolysis suspension discharged to the discharge conduit 2 at the bottom part B was transferred to the digestion device D side via the discharge suspension transfer conduit 17. A hydrolysis solution (500 parts by mass/hour) from which the raw material biomass was removed as solid content from the discharge suspension was extracted by a strainer (opening size: 300 μm) to the hydrolysis solution transfer conduit 18 connected to an extraction port G3 quipped with a strainer (solid-liquid separation device S3) provided at the location of the discharge suspension transfer conduit 17 on the digestion device side. The extracted hydrolysis solution was transferred to the discharge conduit 2 connected to the bottom part B of the continuous primary hydrolysis device R1 and mixed with the discharge suspension (300 parts by mass/hour) discharged from the bottom of the continuous primary hydrolysis device R1, and the mixed discharge suspension (800 parts by mass/hour) was transferred to the strainer by the discharge suspension conduit 17. With the method described above, the portion of the hydrolysis solution from which the raw material biomass was removed was supplied and circulated into a cyclic conduit composed of the discharge suspension transfer conduit 17 and the hydrolysis suspension circulation conduit 18. The inside of the hydrolysis solution circulation conduit 18 was filled in advance with warm water at 95° C. from the aqueous liquid supply device W2 at the time that circulation was begun.

After steady state operation was begun, the hydrolysis solution (200 parts by mass/hour) was continuously extracted as a hydrolysis solution 3 from the extraction conduit 16 connected to the hydrolysis solution circulation conduit 18, and warm water (200 parts by mass/hour) was continuously supplied to the circulation conduit 18 from the aqueous liquid supply device W2 via the supply conduit 15.

The content of the monosaccharides, oligosaccharides, and furfurals contained in the hydrolysis solution 1 extracted from the extraction conduit 3 and the hydrolysis solution 3 extracted from the extraction conduit 16 was measured with the same method as in Production Example 1, and the yield of each component with respect to the raw material (dry mass) was calculated. The results are shown in Table 37.

Production Example 128

All operations were performed with the same method as in Production Example 127 with the exception that the discharge suspension discharged from the bottom of the hydrolysis device in Production Example 127 was not circulated to the cyclic conduit composed of the discharge suspension transfer conduit 17 and the hydrolysis solution circulation conduit 18. The content of the monosaccharides, oligosaccharides, and furfurals contained in the hydrolysis solution 1 extracted from the extraction conduit 3 was measured, and the yield of each component with respect to the raw material (dry mass) was calculated. The results are shown in Table 37.

TABLE 37

| | Yield (%: relative to raw material) | | | | |
|---|---|---|---|---|---|
| | Hydrolysis solution 1 (collected from conduit 3) | | Hydrolysis solution 3 (collected from conduit 16) | | Total |
| Production Example 127 | Monosaccharides | 3.67 | Monosaccharides | 1.66 | 5.33 |
| | Oligosaccharides | 3.46 | Oligosaccharides | 2.06 | 5.52 |
| | Furfurals | 1.52 | Furfurals | 0.87 | 2.39 |
| Production Example 128 | Monosaccharides | 3.65 | Monosaccharides | — | 3.65 |
| | Oligosaccharides | 3.49 | Oligosaccharides | — | 3.49 |
| | Furfurals | 1.50 | Furfurals | — | 1.50 |

As shown in Table 37, the yield (total) of monosaccharides, oligosaccharides, and furfurals increased as a result of extracting only a hydrolysis solution before supplying the hydrolysis suspension containing the hydrolyzed raw material biomass discharged from the bottom of the primary hydrolysis device to the digestion device and also extracting a hydrolysis solution from the hydrolysis solution circulation conduit 18 forming a cyclic circulation system together with the discharge conduit connected to the discharge port of the hydrolysis device.

It was concluded from the above results that hydrolysis progresses further and the yields of monosaccharides, oligosaccharides, and furfurals improve as a result of circulating the hydrolysis solution portion in the hydrolysis suspension discharged from the bottom part B of the primary hydrolysis device through the cyclic conduit connecting the discharge suspension transfer conduit for the hydrolysis suspension formed between the primary hydrolysis device and the digestion device and the circulation conduit for the hydrolysis solution separated from the hydrolysis suspension inside the discharge suspension transfer conduit. In addition, it was concluded that the cause of the improvement in yield was that it was possible to recover substantial amounts of the monosaccharides, oligosaccharides, and furfurals remaining in the hydrolysis suspension in the interval where the hydrolysates are washed by countercurrent washing (below the hydrolysis device) by means of countercurrent washing with the washing solution supplied to the bottom of the device.

Production Example 129

A raw material suspension containing a raw material biomass was prepared from *Eucalyptus pellita* chips with the same method as in Production Example 127, and the solution was subjected to hydrolysis.

As illustrated in FIG. 20, three hours after the supply of the raw material was begun (after steady state operation was begun), a hydrolysis solution 1 (200 parts by mass/hour) was extracted from the extraction conduit 3 from the intermediate extraction port G1 (at a position corresponding to a hydrolysis time of 50 minutes) of the hydrolysis device in a state in which the temperature and pressure inside the hydrolysis device were maintained. On the other hand, warm water at 95° C. (10 parts by mass/hour) from the aqueous liquid supply device W2 was supplied into the continuous primary hydrolysis device R1 from the aqueous liquid supply port E via the aqueous liquid supply conduit 19 at the same time that the discharge of the hydrolysis solution 1 was begun. In addition, washing water was supplied from the washing solution supply device W1 to the bottom of the continuous primary hydrolysis device R1 at a rate of 100 parts by mass/hour by opening the valve V4 of the washing solution supply conduit 6, and the solution was brought into contact, in a countercurrent manner, with a hydrolysis suspension moving downward through the intermediate extraction port G1 in the center of the continuous primary hydrolysis device R1 provided with a stainless steel metal mesh having an opening size of 300 μm.

All other operations were performed with the same methods as in Production Example 127. The content of the monosaccharides, oligosaccharides, and furfurals contained in the hydrolysis solution 1 extracted from the extraction conduit 3 and the hydrolysis solution 3 extracted from the extraction conduit 16 was measured, and the yield of each component with respect to the raw material (dry mass) was calculated. The results are shown in Table 38.

TABLE 38

| | Yield (%: relative to raw material) | | | | |
|---|---|---|---|---|---|
| | Hydrolysis solution 1 (collected from conduit 3) | | Hydrolysis solution 3 (collected from conduit 16) | | Total |
| Production Example 129 | Monosaccharides | 3.62 | Monosaccharides | 2.24 | 5.86 |
| | Oligosaccharides | 3.43 | Oligosaccharides | 2.74 | 6.27 |
| | Furfurals | 1.55 | Furfurals | 1.28 | 2.83 |

As shown in Table 38, when warm water was supplied to the aqueous liquid supply port E positioned below the intermediate extraction port at the same time that the hydrolysis solution was extracted from the intermediate extraction port of the primary hydrolysis device (Production Example 129), the yield of monosaccharides, oligosaccharides, and furfurals increased in comparison to the test in which warm water was not supplied (Production Example 127).

It can be inferred from the above results that the yield of monosaccharides, oligosaccharides, and furfurals improved as a result of the monosaccharides, oligosaccharides, and furfurals becoming more soluble in the aqueous solution from the raw material in the hydrolysis device after extracting the hydrolysis solution from the intermediate extraction port of the hydrolysis device and simultaneously supplying warm water.

Production Example 130

A raw material suspension containing a raw material biomass was prepared from *Eucalyptus pellita* chips with the same method as in Production Example 27, and the solution was subjected to hydrolysis.

As illustrated in FIG. 21, three hours after the supply of the raw material was begun (after steady state operation was begun), a hydrolysis solution 1 (200 parts by mass/hour) was extracted from the intermediate extraction port G1 (at a position corresponding to a hydrolysis time of 50 minutes) on the upper side of the hydrolysis device in a state in which the temperature and pressure inside the continuous primary hydrolysis device R1 were maintained by opening the valve V1 of the hydrolysis solution extraction conduit 3, and a hydrolysis solution 2 (200 parts by mass/hour) was extracted from the intermediate extraction port G2 (at a position corresponding to a hydrolysis time of 70 minutes) on the lower side of the hydrolysis device by opening the valve V2 of the hydrolysis solution extraction conduit 4. Warm water at 95° C. (200 parts by mass/hour) was extracted from the aqueous liquid supply device W2 by opening the valve 3 of the aqueous liquid supply conduit 19 at the same time that the extraction of the hydrolysis solution was begun, and the solution was supplied to the primary hydrolysis device from the aqueous liquid supply port E between the upper intermediate extraction port (G1) and the lower extraction port (G2) for the hydrolysis solution. In addition, washing water was supplied from the washing solution supply device W1 to the bottom of the primary hydrolysis device at a rate of 200 parts by mass/hour by opening the valve V4 of the washing solution supply conduit 6, and the solution was brought into contact, in a countercurrent manner, with a hydrolysis suspension moving downward through the lower intermediate extraction port (G2) in the center of the continuous primary hydrolysis device R1 provided with a stainless steel metal mesh having an opening size of 300 μm.

All other operations were performed with the same methods as in Production Example 127. The content of the monosaccharides, oligosaccharides, and furfurals contained in the hydrolysis solution 1 extracted from the upper extraction conduit 3, the hydrolysis solution 2 extracted from the lower extraction conduit 4, and the hydrolysis solution 3 extracted by the extraction conduit 16 from the hydrolysis solution circulation conduit 18 forming the cyclic conduit described above was measured, and the yield of each component with respect to the raw material (dry mass) was calculated. The results are shown in Table 39.

TABLE 39

| | Yield (%: relative to raw material) | | | | | | |
|---|---|---|---|---|---|---|---|
| | Hydrolysis solution 1 (collected from conduit 3) | | Hydrolysis solution 2 (collected from conduit 4) | | Hydrolysis solution 3 (collected from conduit 16) | | Total |
| Production Example 130 | Monosaccharides | 3.63 | Monosaccharides | 1.57 | Monosaccharides | 1.54 | 6.74 |
| | Oligosaccharides | 3.49 | Oligosaccharides | 1.89 | Oligosaccharides | 1.95 | 7.33 |
| | Furfurals | 1.54 | Furfurals | 0.86 | Furfurals | 0.72 | 3.12 |

As shown in Table 39, when the hydrolysis solutions were extracted by the extraction conduits 3 and 4 from the intermediate extraction ports G1 and G2 at two locations of the continuous primary hydrolysis device R1 and the hydrolysis solution in the hydrolysis suspension from the bottom is also extracted from the extraction conduit 16 of the hydrolysis solution circulation conduit 18 forming the cyclic conduit described above (Production Example 13), the yield of monosaccharides, oligosaccharides, and furfurals increases in comparison to when the hydrolysis solution is extracted by only the extraction conduit 3 from the intermediate extraction port G1 (upper) at one location of the continuous primary hydrolysis device R1 (Production Example 128) or when the hydrolysis solution is extracted from extraction conduits at two locations (Productions Examples 127 and 129).

From the above results, the yield of monosaccharides, oligosaccharides, and furfurals markedly improved when an aqueous liquid (warm water) was supplied at the same time that the hydrolysis solutions were extracted from extraction conduits at two locations of the hydrolysis device at the same volume as the extracted volume, and the hydrolysis solution in the hydrolysis suspension from the bottom is also extracted from the extraction conduit 16 of the circulation conduit 18 forming the cyclic conduit described above.

Production Example 131

Tests were performed using the device illustrated in FIG. 22. Tests were performed with the same method as in Production Example 129, and the hydrolysis solution 1 extracted from the extraction conduit 3 and the hydrolysis solution 3 extracted from the extraction conduit 16 of the hydrolysis solution circulation conduit 18 forming the cyclic conduit described above were transferred to a flash tank (manufactured by Shin-Ei Giken (Ltd.), volume: 4 L). A vapor phase separated by the flash tank (concentration/separation device F) was fed to the condenser C by the conduit 9. After the vapor phase was cooled and condensed, a furfural aqueous solution (40 parts by mass/hour) was extracted from the condensate extraction conduit 4. In addition, an aqueous solution containing sugars or the like (360 parts by mass/hour) was extracted from the extraction conduit 5 as a liquid phase in the flash tank.

The content of monosaccharides, oligosaccharides, and furfurals contained in each aqueous solution obtained from the flash tank was measured, and the yield of each component with respect to the raw material (dry mass) was calculated. The results are shown in Table 40.

TABLE 40

| | | | | Yield (%: relative to raw material) |
|---|---|---|---|---|
| Production Example 131 | Flash tank | Gas phase | Monosaccharides | 0 |
| | | | Oligosaccharides | 0 |
| | | | Furfurals | 4.17 |
| | | Liquid phase | Monosaccharides | 5.82 |
| | | | Oligosaccharides | 6.14 |
| | | | Furfurals | 0.20 |

As shown in Table 40, with the method of Production Example 131, most of the furfural from among the various hydrolysates produced by hydrolysis was extracted from the flash tank while contained in the vapor phase by means of flash distillation in the flash tank. As a result, it was possible to continuously obtain a high-concentration aqueous solution of the furfural that was produced. On the other hand, the liquid phase discharged from the inside of the flash tank after flash distillation contained only a very small amount of furfurals and contained oligosaccharides and monosaccharides at high concentrations. It was thus possible to recover an aqueous solution containing monosaccharides and oligosaccharides at high concentrations from the liquid phase.

Production Example 132

Tests were performed using the device illustrated in FIG. 23. Tests were performed with the same method as in Production Example 130, and the hydrolysis solution 1 extracted from the extraction conduit 3, the hydrolysis solution 2 extracted from the extraction conduit 4, and the hydrolysis solution 3 extracted from the extraction conduit 16 of the hydrolysis solution circulation conduit 18 forming the cyclic conduit described above were pooled and transferred to a flash tank (manufactured by Shin-Ei Giken (Ltd.), volume: 4 L). A vapor phase separated by the flash tank (concentration/separation device F) was cooled by the condenser C, and a furfural aqueous solution (60 parts by mass/hour) was extracted from the condensate extraction conduit 4. In addition, an aqueous solution containing sugars or the like (540 parts by mass/hour) was extracted from the liquid phase extraction conduit 5 as a liquid phase in the flash tank.

The content of monosaccharides, oligosaccharides, and furfurals contained in each aqueous solution obtained from the flash tank was measured, and the yield of each component with respect to the raw material (dry mass) was calculated. The results are shown in Table 41.

TABLE 41

| | | | | Yield (%: relative to raw material) |
|---|---|---|---|---|
| Production Example 132 | Flash tank | Gas phase | Monosaccharides | 0 |
| | | | Oligosaccharides | 0 |
| | | | Furfurals | 5.34 |
| | | Liquid phase | Monosaccharides | 6.68 |
| | | | Oligosaccharides | 7.28 |
| | | | Furfurals | 0.23 |

As shown in Table 41, in the method of Production Example 132 as well, most of the furfural from among the various hydrolysates produced by the hydrolysis reaction was extracted from the flash tank while contained in the vapor phase by means of flash distillation in the flash tank. As a result, it was possible to continuously obtain a high-concentration aqueous solution of the furfural that was produced. On the other hand, the liquid phase discharged from the inside of the flash tank after flash distillation contained only a very small amount of furfurals and contained oligosaccharides and monosaccharides at high concentrations. It was thus possible to recover an aqueous solution containing monosaccharides and oligosaccharides at high concentrations from the liquid phase.

Practical Example 30

Hot Water Treatment

*Eucalyptus pellita* chips (2 mm thick) were pulverized using a Wiley mill [manufactured by Tozai Seiki (Ltd.)], and the resulting homogenate was treated with a stainless steel sieve to obtain a wood powder with a particle size of 100 to 120 μm. An aqueous suspension raw material (raw material suspension) was prepared by mixing the resulting wood powder and ion exchange water at a ratio of 5 parts by mass of ion exchange water per 1 part by mass of the wood chips (dry).

The raw material suspension was continuously supplied from the raw material suspension supply conduit 1 (aqueous suspension raw material supply line 1) connected to the top supply port A of the continuous primary hydrolysis device R1 illustrated in FIG. 24 at a rate of 400 parts by mass/hour. The solution was hydrolyzed in the hydrolysis device at 170° C. and 0.79 MPa, and the hydrolyzed raw material suspension was continuously discharged to the discharge conduit 2 (hydrolysis suspension recovery line 2) from the bottom discharge port B of the continuous primary hydrolysis device R1 by opening the decompression valve VP. The retention time in the hydrolysis device was set to three hours.

Three hours after supply was begun, a hydrolysis solution (130 parts by mass/hour) separated from the hydrolysis suspension was extracted from the intermediate extraction port G1 (at a position corresponding to a hydrolysis time of 1.5 hours) provided with a stainless steel metal mesh with an opening size of 80 μm in the center of the hydrolysis device in a state in which the temperature and pressure in the hydrolysis device were maintained by opening the valve V of the extraction conduit 3 (hydrolysis solution transfer line 3), and the solution was transferred to the flash tank [manufactured by Shin-Ei Giken (Ltd.), volume: 4 L].

The furfural concentration in the hydrolysis solution extracted to the extraction conduit 3 from the intermediate extraction port G1 of the continuous primary hydrolysis device R1 was 0.15 mass %, and the concentration of the SS (suspended substance) was 0.12 mass %.

The hydrolysis solution was separated into a vapor phase (vapor fraction) and a liquid phase (solution fraction) by the flash tank, and the vapor phase (vapor fraction) of the flash tank was extracted by opening the valve V of the vapor phase transfer conduit 9. The vapor phase was passed through the condenser C so as to be cooled to 20° C., and a furfural aqueous solution (9.8 parts by mass/hour) was recovered by opening the valve of the condensate extraction conduit 4 (furfural aqueous solution recovery line 4). In addition, the solution fraction (120 parts by mass/hour) in the flash tank was extracted by opening the valve of the liquid phase extraction conduit 5 (recovery line 5 for an aqueous solution containing sugars or the like).

The content of total sugar, monosaccharides, oligosaccharides, and furfurals contained in each aqueous solution obtained from the flash tank was measured with the same method as in Production Example 1, and the yield of each component with respect to the raw material (dry mass) was calculated.

The furfural content of the furfural aqueous solution extracted from the condenser C by the furfural aqueous solution recovery line 4 was determined using HPLC (manufactured by Waters). Using an Aminex HPX87-H (manufactured by Bio-Rad) as a column and using 5 mM sulfuric acid for the mobile layer, the content was detected with an R1 detector. The furfural yield in the gaseous phase (vapor fraction) with respect to the chips (dry mass) was calculated from the quantitative value of furfural in the aqueous solution. In addition the furfural yield in the solution fraction recovered from the recovery line 5 for the aqueous solution containing sugars or the like was also calculated in the same manner.

The results are shown in Table 42.

Practical Example 31

Acid Treatment

A *Eucalyptus pellita* wood powder was prepared with the same method as in Practical Example 30, and an aqueous suspension raw material (raw material suspension) in which the wood powder and ion exchange water containing sulfuric acid at a concentration of 1 mass % were mixed at a ratio of 5 parts by mass of ion exchange water containing sulfuric acid per 1 part by mass of the wood powder (dry) was prepared. The raw material suspension was hydrolyzed with the same method as in Practical Example 30.

The furfural concentration in the hydrolysis solution immediately after being extracted to the extraction conduit 3 (transfer line 3) from the continuous primary hydrolysis device R1 was 0.16 mass %, and the concentration of the SS suspended substance) was 0.14 mass %.

The hydrolysis solution was separated into a vapor phase (vapor fraction) and a liquid phase (solution fraction) by the flash tank, and the vapor phase (vapor fraction) of the flash tank was extracted to the vapor phase transfer conduit 9. The vapor phase was passed through the condenser C so as to be cooled to 20° C., and a furfural aqueous solution (9.9 parts by mass/hour) was extracted from the condensate extraction conduit 4 (furfural aqueous solution recovery line 4). In addition, an aqueous solution containing sugars or the like (119 parts by mass/hour) as a liquid phase in the flash tank was extracted from the conduit 5.

The furfural content of the furfural aqueous solution obtained by feeding the gaseous phase in the flash tank F to the condenser C was determined using HPLC (manufactured by Waters) Using an Aminex HPX87-H (manufactured by Bio-Rad) as a column and using 5 mM sulfuric acid for the mobile layer, the content was detected with an R1 detector. The furfural yield in the gaseous phase (vapor fraction) with respect to the chips (dry mass) was calculated from the quantitative value of furfural in the aqueous solution. In addition, the furfural yield in the liquid phase (solution fraction) was also calculated in the same manner. The results are shown in Table 42.

In addition, the yield of each component of total sugar, monosaccharides, oligosaccharides, and furfurals contained in each aqueous solution obtained from the flash tank with respect to the raw material (dry mass) was calculated. The results are shown in Table 43.

Comparative Example 30

Hot Water Treatment

In the method of Practical Example 30, a hydrolysis solution was obtained by feeding the hydrolysis solution extracted to the extraction conduit 3 from the intermediate extraction port G1 of the continuous primary hydrolysis device R1 (furfural concentration: 0.15 mass %, SS (suspended substance) concentration: 0.14 mass %) to a storage tank (not illustrated), without transferring the solution to the flash tank illustrated in FIG. 24, and then gradually cooling the solution to 20° C.

The furfural content contained in the resulting hydrolysis solution was measured with the same method as in Practical Example 1, and the furfural yield with respect to the chips (dry mass) was calculated. The results are shown in Table 42.

In addition, the content of total sugar, monosaccharides, oligosaccharides, and furfurals contained in the resulting hydrolysis solution was measured with the same method as in Production Example 1, and the yield of each component with respect to the chips (dry mass) was calculated. The results are shown in Table 43.

Comparative Example 31

Figure 25:
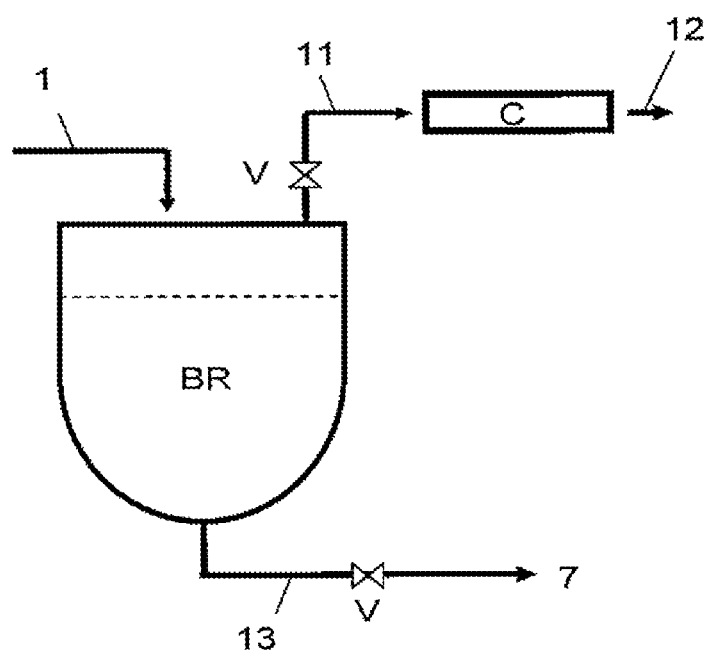
FIG. 25 illustrates a device for producing monosaccharides, oligosaccharides, and/or furfurals with a batch digester.

Hot Water Treatment 400 parts by mass of a raw material suspension of a raw material prepared in the same manner as in Practical Example 30 was supplied to the batch digester BR1 [manufactured by Toyo Koatsu (Inc.)] illustrated in FIG. 25 from the raw material suspension supply conduit 1 and hydrolyzed for 1.5 hours at 170° C. and 0.79 MPa.

After treatment, the vapor phase was fed to the condenser C from the vapor phase conduit 11 by opening the valve V of the digester BR1 and cooled to 20° C. A furfural aqueous solution (9.8 parts by mass/hour) was recovered by the condensate extraction conduit 12 (furfural aqueous solution recovery line 12). The suspension in the digester (119 parts by mass/hour) was discharged to the outside of the digester from the hydrolysis suspension recovery conduit 13 (hydrolysis suspension recovery line 13).

The content of furfural contained in the aqueous solution obtained by cooling the vapor phase and the furfural content in the liquid of the suspension discharged from the digester were determined with the same method as in Practical Example 1. The results are shown in Table 42.

The content of total sugar, monosaccharides, oligosaccharides, and furfurals contained in the aqueous solution obtained by cooling the vapor phase and the suspension discharged from the digester was measured with the same method as in Production Example 1. The results are shown in Table 43.

TABLE 42

| | | | Furfural content (%) (content in recovered aqueous solution) | Furfural yield (%) |
|---|---|---|---|---|
| Practical Example 30 (hot water treatment) | Flash tank | Gas phase | 3.8% | 5.8% |
| | Flash tank | Liquid phase | 0.04% | 0.6% |
| Practical Example 31 (acid treatment) | Flash tank | Gas phase | 4.0% | 6.1% |
| | Flash tank | Liquid phase | 0.04% | 0.6% |
| Comparative Example 30 (hot water treatment) | Hydrolysis device | Gas phase | — | — |
| | Hydrolysis device | Liquid phase | 0.16% | 2.4% |
| Comparative Example 31 (hot water treatment) | Digester | Gas phase | 3.0% | 4.6% |
| | Digester | Liquid phase | 0.12% | 1.7% |

TABLE 43

| | | | | Yield (%: relative to raw material) |
|---|---|---|---|---|
| Practical Example 30 (hot water treatment) | Flash tank | Gas phase | Total sugar | 0 |
| | | | Monosaccharides | 0 |
| | | | Oligosaccharides | 0 |
| | | | Furfurals | 5.8 |
| | | Liquid phase | Total sugar | 7.0 |
| | | | Monosaccharides | 4.7 |
| | | | Oligosaccharides | 2.3 |
| | | | Furfurals | 0.6 |
| Practical Example 31 (acid treatment) | Flash tank | Gas phase | Total sugar | 0 |
| | | | Monosaccharides | 0 |
| | | | Oligosaccharides | 0 |
| | | | Furfurals | 6.1 |
| | | Liquid phase | Total sugar | 7.4 |
| | | | Monosaccharides | 4.9 |
| | | | Oligosaccharides | 2.5 |
| | | | Furfurals | 0.6 |
| Comparative Example 30 (hot water treatment) | Hydrolysis device | Gas phase | Total sugar | — |
| | | | Monosaccharides | — |
| | | | Oligosaccharides | — |
| | | | Furfurals | — |

TABLE 43-continued

| | | | | Yield (%: relative to raw material) |
|---|---|---|---|---|
| | | Liquid phase | Total sugar | 7.0 |
| | | | Monosaccharides | 4.7 |
| | | | Oligosaccharides | 2.3 |
| | | | Furfurals | 2.4 |
| Comparative Example 31 (hot water treatment) | Digester | Gas phase | Total sugar | 0 |
| | | | Monosaccharides | 0 |
| | | | Oligosaccharides | 0 |
| | | | Furfurals | 4.6 |
| | | Liquid phase | Total sugar | 4.9 |
| | | | Monosaccharides | 3.2 |
| | | | Oligosaccharides | 1.7 |
| | | | Furfurals | 1.7 |

As shown in Tables 42 and 43, with the methods of Practical Examples 30 and 31, most of the furfural from among the various hydrolysates produced in the hydrolysis reaction was extracted from the flash tank while contained in the vapor phase by means of flash distillation in the flash tank. As a result, it was possible to continuously obtain a high-concentration aqueous solution of the furfural that was produced.

On the other hand, the liquid phase discharged from the inside of the flash tank after flash distillation contained only a very small amount of furfurals and contained oligosaccharides and monosaccharides at high concentrations. It was thus possible to recover an aqueous solution containing monosaccharides and oligosaccharides at high concentrations from the liquid phase. In the tests using flash distillation (Practical Examples 30 and 31), the yield of oligosaccharides and monosaccharides recovered from the liquid phase was higher than in the test using a digester (Comparative Example 31).

In contrast, in the case of the method of Comparative Example 30, in which flash distillation is not performed by the flash tank, the entire amount of the furfural produced by the continuous primary hydrolysis device R1 is obtained as a hydrolysate-containing aqueous solution contained at a low concentration in a large volume of the liquid phase containing polysaccharides, oligosaccharides, monosaccharides, organic acids, and the like, so an expensive separation/purification step is required to recover the target furfural from the hydrolysate-containing aqueous solution.

In addition, when performing batch hydrolysis in Comparative Example 31, it is possible to obtain an aqueous solution containing high-purity furfural as an aqueous solution obtained by condensing the vapor phase separated from the hydrolysis solution, but the amount of produced furfural that is recovered in a state contained in the gaseous phase is lower than when the flash tank of the practical examples is installed. A non-negligible amount of produced furfural is contained in the liquid phase, which also contains polysaccharides, oligosaccharides, monosaccharides, organic acids, and the like, so in order to increase the yield of furfural, an expensive recovery step for recovering furfural from the liquid phase is required.

Practical Example 32

Hot Water Treatment

In the continuous primary hydrolysis device R1 illustrated in FIG. 24, the concentration of the furfural-containing aqueous solution by means of hydrolysis and flash distillation was performed in the same manner as in the method described in Practical Example 9 with the exception of supplying washing water at a rate of 400 parts by mass/hour from the washing solution supply device W1 at the bottom of the device via the washing water supply conduit 6 and bringing the solution into contact, in a countercurrent manner, with a hydrolysis suspension moving downward from the intermediate extraction port G1 of the continuous primary hydrolysis device R1 provided with a stainless steel metal mesh having an opening size of 80 μm. Three hours after supply was begun, a hydrolysis solution (260 parts by mass/hour) separated from the hydrolysis suspension was extracted from the intermediate extraction port G1 (at a position corresponding to a hydrolysis time of 1.5 hours) provided with a stainless steel metal mesh with an opening size of 80 μm in the center of the hydrolysis device in a state in which the temperature and pressure in the hydrolysis device were maintained by opening the valve V of the conduit 3, and the solution was transferred to the flash tank [manufactured by Shin-Ei Giken (Ltd.), volume: 4 L].

The furfural concentration in the hydrolysis solution extracted to the conduit 3 from the intermediate extraction port G1 of the continuous primary hydrolysis device R1 was 0.08 mass %, and the concentration of the SS (suspended substance) was 0.07 mass %.

The vapor phase (vapor fraction) separated by the flash tank was extracted from the conduit 9 and cooled by the condenser C, and a furfural aqueous solution (19.8 parts by mass/hour) was extracted from the condensate extraction conduit 4. In addition, an aqueous solution containing sugars or the like (240 parts by mass/hour) was extracted from the conduit 5 as a liquid phase in the flash tank.

The furfural content contained in each aqueous solution obtained from the flash tank was measured with the same method as in Practical Example 1, and the furfural yield with respect to the chips (dry) was calculated. The results are shown in Table 44.

The content of total sugar, monosaccharides, oligosaccharides, and furfural contained in each aqueous solution obtained from the flash tank was measured with the same method as in Production Example 1, and the yield of each component with respect to chips (dry mass) was calculated. The results are shown in Table 45.

Practical Example 33

Hot Water Treatment

Hydrolysis was performed the method with the same method as in Practical Example 30 with the exception of using cedar (2 mm thick) as a raw material in the method described in Practical Example 30.

The furfural concentration in the hydrolysis solution immediately after being extracted to the conduit 3 (transfer line 3) from the continuous primary hydrolysis device R1 was 0.16 mass %, and the concentration of the SS suspended substance) was 0.13 mass %.

A vapor phase separated by the flash tank was cooled by the condenser C, and a furfural aqueous solution (9.9 parts by mass/hour) was extracted from the furfural aqueous solution recovery line 4. In addition, an aqueous solution containing sugars or the like (119 parts by mass/hour) as a liquid phase in the flash tank was extracted from the conduit 5.

The furfural content contained in each aqueous solution obtained from the flash tank F was measured with the same method as in Practical Example 1, and the furfural yield with respect to the chips (dry) was calculated. The results are shown in Table 44.

The content of total sugar, monosaccharides, oligosaccharides, and furfural contained in each aqueous solution obtained from the flash tank was measured with the same method as in Production Example 1, and the yield of each component with respect to chips (dry mass) was calculated. The results are shown in Table 45.

TABLE 44

| | | | Furfural content (%) (content in recovered aqueous solution) | Furfural yield (%) |
|---|---|---|---|---|
| Practical Example 32 (hot water treatment) | Flash tank | Gas phase | 4.2% | 6.4% |
| | Flash tank | Liquid phase | 0.03% | 0.5% |
| Practical Example 33 (hot water treatment) | Flash tank | Gas phase | 3.6% | 5.5% |
| | Flash tank | Liquid phase | 0.04% | 0.4% |

TABLE 45

| | | | | Yield (%: relative to raw material) |
|---|---|---|---|---|
| Practical Example 32 (hot water treatment) | Flash tank | Gas phase | Total sugar | 0 |
| | | | Monosaccharides | 0 |
| | | | Oligosaccharides | 0 |
| | | | Furfurals | 6.4 |
| | | Liquid phase | Total sugar | 7.5 |
| | | | Monosaccharides | 5.0 |
| | | | Oligosaccharides | 2.5 |
| | | | Furfurals | 0.5 |
| Practical Example 33 (hot water treatment) | Flash tank | Gas phase | Total sugar | 0 |
| | | | Monosaccharides | 0 |
| | | | Oligosaccharides | 0 |
| | | | Furfurals | 5.5 |
| | | Liquid phase | Total sugar | 6.1 |
| | | | Monosaccharides | 4.2 |
| | | | Oligosaccharides | 1.9 |
| | | | Furfurals | 0.4 |

With the system in which a washing solution was supplied to the continuous primary hydrolysis device illustrated in FIG. 24 (Practical Example 32), the yield of monosaccharides, oligosaccharides, and furfurals contained in the hydrolysis solution after secondary hydrolysis improved in comparison to the system in which the washing solution of FIG. 24 was not supplied (Practical Example 30).

In Practical Example 33 in which the biomass raw material was replaced with cedar, the same results as in Practical Example 30 using *Eucalyptus pellita* as a raw material were obtained.

Production Example 132

Figure 26:
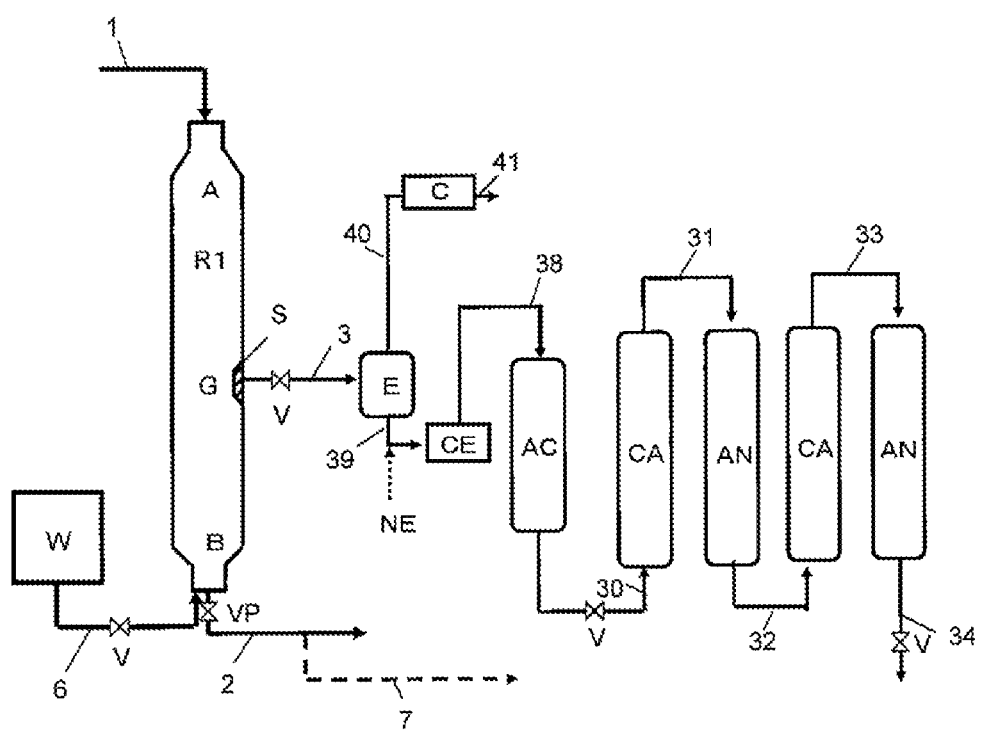
FIG. 26 illustrates the method for manufacturing monosaccharides and oligosaccharides with a continuous hydrolysis device according to the present invention.

Tests were performed with the manufacturing process illustrated in FIG. 26.

<Production of Sugar Solution with High Xylose Content>

Primary hydrolysis was performed with the same method as in Production Example 12. A primary hydrolysis solution after primary hydrolysis was transferred from the line 3 to an evaporator (concentration device E), and the solution was separated by the evaporator into a liquid phase (containing sugars) and a vapor phase (containing furfural). The liquid phase was concentrated until the total sugar concentration of the liquid phase reached 25 mass %. On the other hand, the vapor phase was condensed by the condenser C via the line 39, and a concentrate having high furfural content was extracted from the line 40. The precipitate contained in the concentrate (liquid phase) separated by the evaporator was removed using a ceramic filter CE, and the filtrate was separated. The separated filtrate was passed through an activated carbon column AC filled with particulate activated carbon (MS10 manufactured by Calgon Carbon) from the line 38 at a flow rate of SV=2 so as to decolorize the solution. Next, the decolorized concentrate was passed through a column filled with a cation exchange resin CA (CT200 manufactured by Organo) from a line 30, and the solution was further passed through a column filled with an anion exchange resin AN (IRA96SB manufactured by Organo) from a line 31 at SV=2. After an aqueous solution (containing sugars) discharged from the anion exchange resin AN was further passed through the cation exchange resin CA via a line 32 and the anion exchange resin AN via a line 33, an aqueous solution (sugar solution) was recovered from a line 34 connected to the anion exchange resin. The recovered sugar solution was concentrated by an evaporator to obtain 70 mass % liquid sugar. The absorbance at 420 nm of the resulting liquid sugar was 0, and the electrical conductivity was 0.001 mS/m. The sugar composition of the liquid sugar is shown in Table 46.

Production Example 133

Tests were performed with the manufacturing process illustrated in FIG. 26.
<Production of Sugar Solution Having High Xylooligosaccharide Content>
Primary hydrolysis was performed with the same method as in Production Example 24. All other operations were performed with the same methods as in Production Example 132. The absorbance at 420 nm of the 70 mass % liquid sugar concentrated by the evaporator was 0, and the electrical conductivity was 0.001 mS/m. The sugar composition of the liquid sugar is shown in Table 46.

Production Example 134

Figure 27:
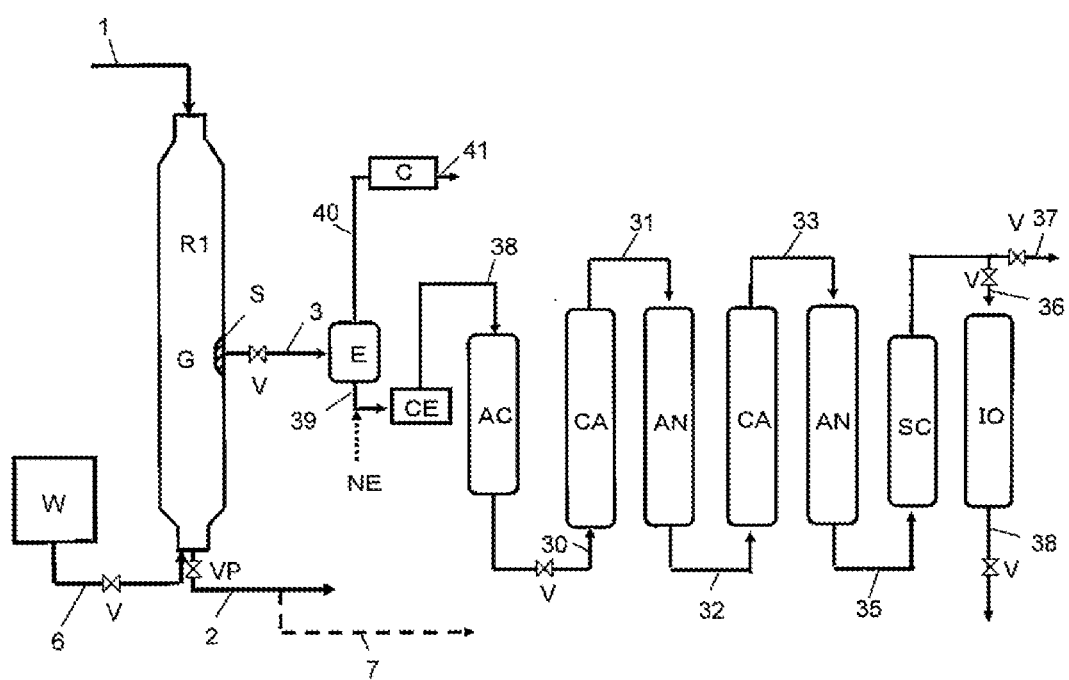
FIG. 27 illustrates the method for manufacturing monosaccharides and oligosaccharides with a continuous hydrolysis device according to the present invention.

Tests were performed with the manufacturing process illustrated in FIG. 27.
<Production of Sugar Solution Having High Xylooligosaccharide Content>
Primary hydrolysis was performed with the same method as in Production Example 24. A primary hydrolysis solution after primary hydrolysis was transferred from the line 3 to an evaporator (concentration device E), and the solution was separated by the evaporator into a liquid phase (containing sugars) and a vapor phase (containing furfural). The liquid phase was concentrated until the total sugar concentration of the liquid phase reached 25 mass %. On the other hand, the vapor phase was condensed by the condenser C via the line 39, and a concentrate having high furfural content was extracted from the line 40. The precipitate contained in the concentrate (liquid phase) separated by the evaporator was removed using a ceramic filter CE, and the filtrate was separated. The separated filtrate was passed through an activated carbon column AC filled with particulate activated carbon (MS10 manufactured by Calgon Carbon) from the line 38 at a flow rate of SV=2 so as to decolorize the solution. Next, the decolorized concentrate was passed through a column filled with a cation exchange resin CA (CT200 manufactured by Organo) from a line 30, and the solution was further passed through a column filled with an anion exchange resin AN (IRA96SB manufactured by Organo) from a line 31 at SV=2. An aqueous solution (containing sugars) discharged from the anion exchange resin AN was further passed through the cation exchange resin CA via a line 32 and the anion exchange resin AN via a line 33.

Next, an aqueous solution (sugar solution) discharged from a line 35 connected to the anion exchange resin AN was passed through a two-component separation chromatographic separation device SC (manufactured by the Nippon Rensui Co.) filled with a cation exchange resin (manufactured by Mitsubishi Scientific, Diaion UBK530 (Na type)), and a monosaccharide fraction was recovered from a line 37. An oligosaccharide fraction was passed through a polisher filled with a mixture of an ion exchange resin 10 consisting of a cation exchange resin (IRA120B manufactured by Organo) and an anion exchange resin (XE583 manufactured by Organo) at a ratio of 1:2 via a line 36 at a flow rate of SV=2 to recover a sugar solution from a line 38. The recovered sugar solution was concentrated by an evaporator to form 70 mass % liquid sugar. The absorbance at 420 nm of the 70 mass % liquid sugar concentrated by the evaporator was 0, and the electrical conductivity was 0.001 mS/m. The sugar composition of the liquid sugar is shown in Table 46.

Production Example 135

Tests were performed with the manufacturing process illustrated in FIG. 26.
<Production of Sugar Solution with High Xylose Content>
Production was implemented with the same method as in Production Example 132. A sugar solution was produced with exactly the same method as in Production Example 132 with the exception that a phenol/formadehyde resin/synthetic adsorption resin (manufactured by Ajinomoto Fine Techno Co., Inc.) was used instead of the activated carbon column AC. The absorbance at 420 nm of the 70 mass % liquid sugar concentrated by the evaporator was 0, and the electrical conductivity was 0.001 mS/m. The sugar composition of the liquid sugar is shown in Table 46.

TABLE 46

| | Sugar composition (%) | | | | | |
| --- | --- | --- | --- | --- | --- | --- |
| | Xylose | Glucose | Galactose | Mannose | Arabinose | Oligosaccharides |
| Production Example 132 | 53.1 | 6.2 | 7.7 | 1.7 | 1.6 | 29.7 |
| Production Example 133 | 29.4 | 4.4 | 4.9 | 1.5 | 1.3 | 58.5 |
| Production Example 134 | 7.6 | 2.5 | 1.8 | 0.4 | 0.3 | 87.4 |
| Production Example 135 | 53.3 | 6.2 | 7.6 | 1.6 | 1.6 | 29.7 |

In Production Examples 132 and 135, it was possible to produce liquid sugars having high xylose content. On the other hand, in Production Examples 133 and 134, it was possible to produce liquid sugars having high oligosaccharide content.

Production Example 136

Figure 28:
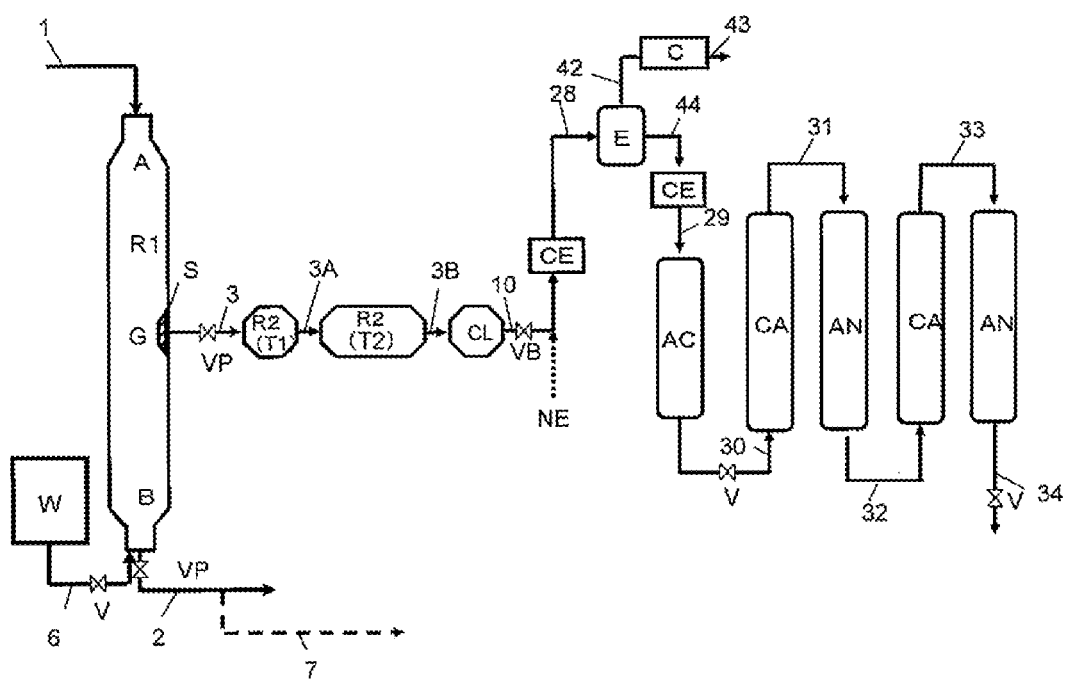
FIG. 28 illustrates an example of a device for implementing the method for continuously manufacturing monosaccharides and oligosaccharides from biomass according to the present invention.

Tests were performed with the manufacturing process illustrated in FIG. 28.
<Production of Sugar Solution Containing Xylose>
Primary hydrolysis and secondary hydrolysis were performed with the same method as in Production Example 70. Sugars contained in the hydrolysis solution (secondary hydrolysis solution) were purified using the hydrolysis solution after secondary hydrolysis. First, calcium hydroxide was added to the secondary hydrolysis solution, and after the pH was adjusted to 2.7, the gypsum that was produced was separated into gypsum and a filtrate using a ceramic filter CE. The resulting filtrate was transferred from the line 3 to the evaporator (concentration device E), and the filtrate was separated by the evaporator into a liquid phase (containing sugars) and a vapor phase (containing furfural). The liquid phase was concentrated until the total sugar concentration of the liquid phase reached 50 mass %. On the other hand, the vapor phase was condensed by the condenser C via a line 42, and a concentrate having high furfural content was extracted from a line 43. The precipitate contained in the concentrate (liquid phase) separated by the evaporator was removed using a ceramic filter CE, and the filtrate was separated.

This filtrate (concentrate) was passed through an activated carbon column AC filled with particulate activated carbon (MS10 manufactured by Calgon Carbon) from a line 29 at a flow rate of SV=2 so as to decolorize the solution. Next, the decolorized concentrate was passed through a column filled with a cation exchange resin CA (CT200 manufactured by Organo) from a line 30, and the solution was further passed through a column filled with an anion exchange resin AN (IRA96SB manufactured by Organo) from a line 31 at SV=2. After an aqueous solution (containing sugars) discharged from the anion exchange resin AN was further passed through the cation exchange resin CA via the line 32 and the anion exchange resin AN via the line 33, an aqueous solution (sugar solution) was recovered from the line 34. The resulting sugar solution was concentrated by an evaporator to obtain 70 mass % liquid sugar. The absorbance at 420 nm of the resulting liquid sugar was 0, and the electrical conductivity was 0.001 mS/m. The sugar composition of the liquid sugar is shown in Table 47.

Production Example 137

Figure 29:
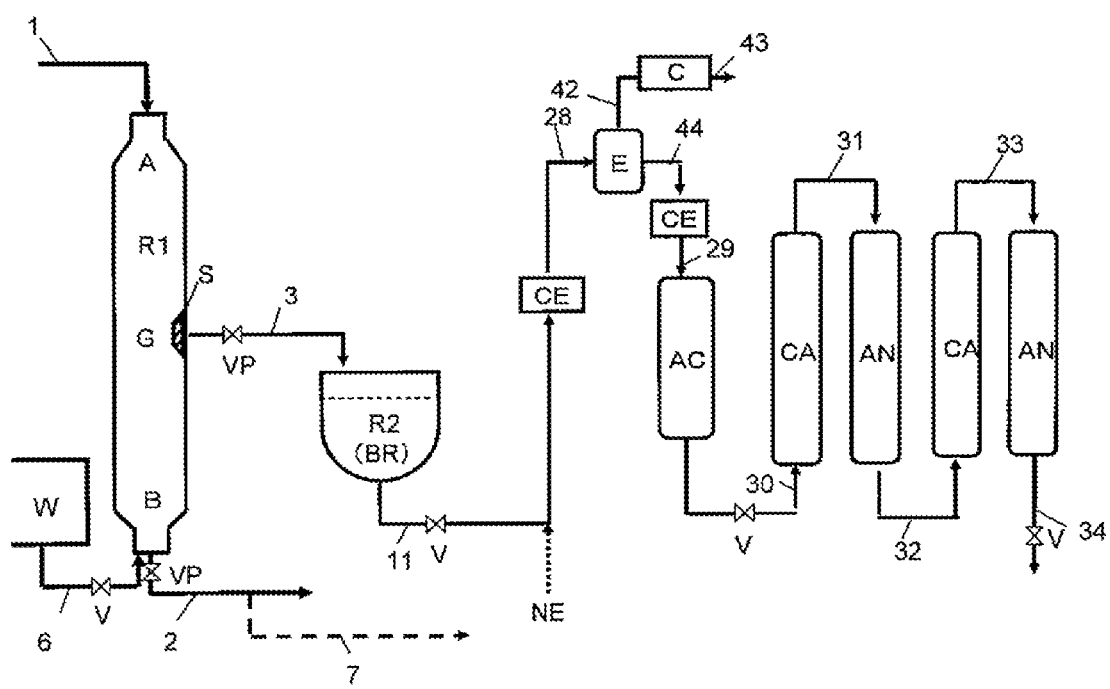
FIG. 29 illustrates an example of a device for implementing the method for continuously manufacturing monosaccharides and oligosaccharides from biomass according to the present invention.

Tests were performed with the manufacturing process illustrated in FIG. 29.
<Production of Sugar Solution Containing Xylose>
Primary hydrolysis and secondary hydrolysis were performed with the same method as in Production Example 85. Liquid sugar was produced with the same method as in Practical Example 136 using the hydrolysis solution after secondary hydrolysis. The absorbance at 420 nm of the 70 mass % liquid sugar concentrated by the evaporator was 0, and the electrical conductivity was 0.001 mS/m. The sugar composition of the liquid sugar is shown in Table 47.

Production Example 138

Tests were performed with the manufacturing process illustrated in FIG. 29.
<Production of Sugar Solution Containing Xylose>
Primary hydrolysis and secondary hydrolysis were performed with the same method as in Production Example 85. A sugar solution was produced with exactly the same method as in Production Example 136 with the exception that a phenol/formadehyde resin/synthetic adsorption resin (manufactured by Ajinomoto Fine Techno Co., Inc.) was used instead of the activated carbon column AC. The absorbance at 420 nm of the 70 mass % liquid sugar concentrated by the evaporator was 0, and the electrical conductivity was 0.001 mS/m. The sugar composition of the liquid sugar is shown in Table 47.

Production Example 139

Figure 30:
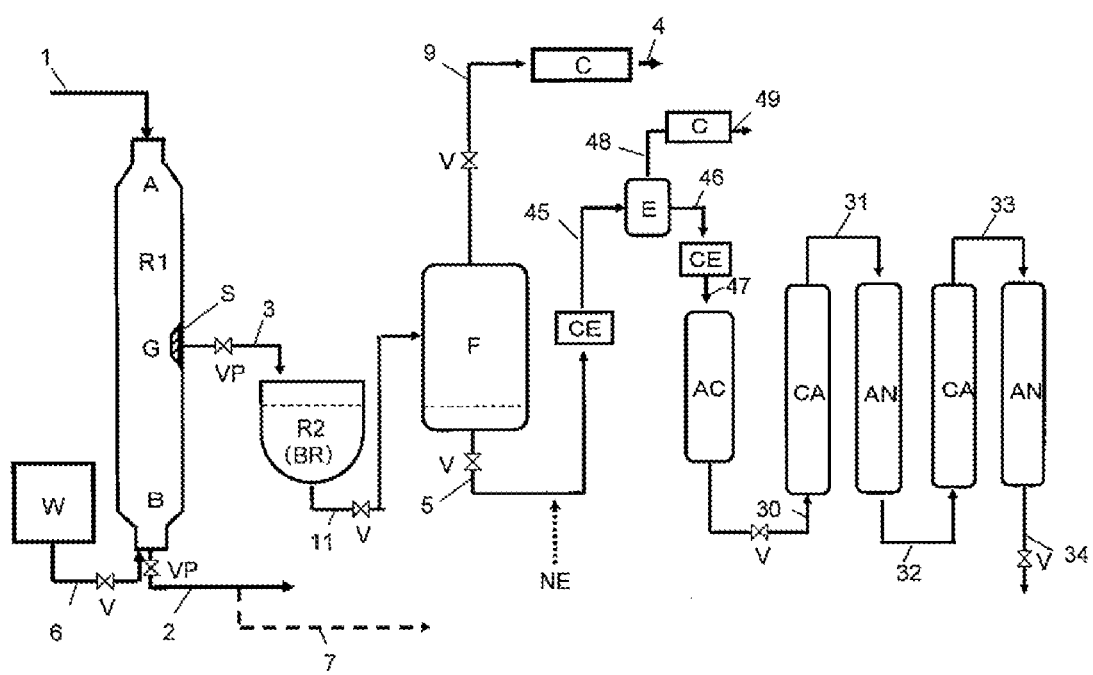
FIG. 30 illustrates an example of a device for implementing the method for continuously manufacturing monosaccharides and oligosaccharides from biomass according to the present invention.

Tests were performed with the manufacturing process illustrated in FIG. 30.
<Production of Sugar Solution Containing Xylose>
Primary hydrolysis and secondary hydrolysis were performed with the same method as in Production Example 92, and the solution was separated by the flash tank into a vapor phase and a liquid phase. Calcium hydroxide was added to the liquid phase in the flash tank, and after the pH was adjusted to 2.7, the gypsum that was produced was separated into gypsum and a filtrate using a ceramic filter CE. The resulting filtrate was transferred from a line 45 to the evaporator (concentration device E), and the filtrate was separated by the evaporator into a liquid phase (containing sugars) and a vapor phase (containing furfural). The liquid phase was concentrated until the total sugar concentration of the liquid phase reached 50 mass %. On the other hand, the vapor phase was condensed by the condenser C via a line 48, and a concentrate having high furfural content was extracted from a line 49. The precipitate contained in the concentrate (liquid phase) separated by the evaporator was removed using a ceramic filter CE, and the filtrate was separated.

This filtrate (concentrate) was passed through an activated carbon column AC filled with particulate activated carbon (MS10 manufactured by Calgon Carbon) from a line 47 at a flow rate of SV=2, and liquid sugar was produced with the same method as in Production Example 54. The sugar solution from which the aqueous solution (sugar solution) was recovered via the line 34 was concentrated by the evaporator to obtain 70 mass % liquid sugar. The absorbance at 420 nm of the 70 mass % liquid sugar concentrated by the evaporator was 0, and the electrical conductivity was 0.001 mS/m. The sugar composition of the liquid sugar is shown in Table 47.

TABLE 47

| | Sugar composition (%) | | | | | |
| --- | --- | --- | --- | --- | --- | --- |
| | Xylose | Glucose | Galactose | Mannose | Arabinose | Oligosaccharides |
| Production Example 136 | 76.2 | 9.1 | 11.1 | 1.9 | 1.7 | 0.0 |
| Production Example 137 | 76.0 | 9.3 | 10.8 | 2.1 | 1.8 | 0.0 |

TABLE 47-continued

| | Sugar composition (%) | | | | | |
|---|---|---|---|---|---|---|
| | Xylose | Glucose | Galactose | Mannose | Arabinose | Oligosaccharides |
| Production Example 138 | 76.1 | 9.3 | 10.7 | 2.1 | 1.8 | 0.0 |
| Production Example 139 | 62.8 | 5.1 | 5.7 | 1.0 | 0.8 | 24.6 |

In Production Examples 136, 137, and 138, it was possible to produce liquid sugars having high xylose content. On the other hand, in Production Example 139, it was possible to produce a liquid sugar having high xylose and oligosaccharide content.

Practical Example 34

Tests were performed with the same method as in Practical Example 15. After secondary hydrolysis, a vapor phase was extracted using the valve V of the vapor phase transfer line 21 connected to the secondary reaction vessel BR2, and a concentrate containing furfurals (20° C.) was recovered from the vapor phase with the same method as in Practical Example 15 (furfural concentrate A).

Next, as illustrated in FIG. 31, the inside of the secondary reaction vessel BR2 was decompressed using a decompression device VAC while maintaining the secondary reaction vessel BR2 (liquid phase) at 90° C. A vapor phase containing furfurals was extracted from this liquid phase via the vapor transfer conduit 21, and this was fed to the condenser C and condensed. The condensate was fed to the distillation device EV and concentrated, and a concentrate (20° C.) containing furfurals was recovered (fufural concentrate B).

The content of furfurals contained in each of the furfural concentrates (furfural concentrate A and furfural concentrate B) was measured, and the yield of furfurals (total value for furfural concentrate A and furfural concentrate B) with respect to the raw material (dry mass) was calculated. A test in which furfurals were not collected with the decompression device VAC from the liquid phase from which the vapor phase was removed after secondary hydrolysis (Practical Example 15) was used as a comparative example. The results are shown in Table 48.

TABLE 48

| | Secondary hydrolysis conditions (batch type) 170° C., 30 minutes | Furfural yield (%: relative to raw material) |
|---|---|---|
| Practical Example 34 | With vacuum distillation of the liquid phase | 8.1 |
| Practical Example 15 | Without vacuum distillation of the liquid phase | 6.1 |

By subjecting the liquid phase from which the vapor phase is removed after secondary hydrolysis to vacuum distillation at 90° C., it was possible to further recover the furfurals remaining in the liquid phase, and the furfural yield improved as a result.

INDUSTRIAL APPLICABILITY

The method of the present invention is a method with which furfural, which is used as a pharmaceutical intermediate, a raw material for plastics, or the like, or furfurals used as raw materials for furfuryl alcohols as raw materials for furan resins or monosaccharides and oligosaccharides, which are expected to be in greater demand in the future as food products or food additives, can be produced by effectively utilizing unused biomass such as "waste biomass" as a biomass resource without incinerating the biomass. The method may also be used as a technique for reducing $CO_2$ emissions, which is a critical technique for addressing global warming.

All of the publications, patents, and patent applications cited in this specification are incorporated directly into this specification by reference.

REFERENCE NUMERALS

1: raw material suspension supply conduit
2: hydrolysis suspension discharge conduit
3: primary hydrolysis solution extraction conduit
3A: primary hydrolysis solution transfer conduit
3B: primary hydrolysis solution transfer conduit
4: condensate extraction conduit
5: liquid phase extraction conduit
6: washing solution supply conduit
7: hydrolysis suspension transfer conduit
8: recovery conduit for an aqueous phase containing sugars or the like
9: vapor phase transfer conduit
10: secondary hydrolysis solution transfer conduit
11: secondary hydrolysis solution extraction conduit
11a: secondary hydrolysate extraction conduit
12: condensate extraction conduit
13: hydrolysis suspension recovery conduit
14: biomass transfer conduit
15: aqueous liquid supply conduit
16: hydrolysis solution extraction conduit
17: hydrolysis suspension transfer conduit
18: hydrolysis solution circulation conduit
19: aqueous liquid supply conduit
20: hydrolysis solution extraction conduit
21: vapor phase transfer conduit
22: circulation conduit for an aqueous solution containing sugars or the like
25: furfural concentrate recovery conduit
26: recovery conduit for an aqueous solution containing sugars or the like
27: transfer conduit for an aqueous solution containing sugars or the like
28': decompression line
R1: continuous primary hydrolysis device
R2: secondary hydrolysis device
T1: temperature adjustment device
2: constant-temperature device
CL: cooling device
BR1: reaction vessel (batch digester)
BR2: secondary reaction vessel D: digestion device
BO: recovery boiler
A: raw material suspension supply port
B: hydrolysis suspension discharge port
E: aqueous liquid supply port
S1 to S4: solid-liquid separation devices
1: intermediate extraction port on upper side
G2: intermediate extraction port on lower side
G3: extraction port
G4: extraction port
C: condenser
F: concentration/separation device
EV: distillation device
W1: washing solution supply device
W2: aqueous liquid supply device
V1 to V9: valves
VP: decompression valve
VB: back pressure valve
TA1: aqueous solution storage tank
TA2: aqueous solution storage tank
C: condenser
EV: distillation device
G: intermediate extraction port
R1: primary hydrolysis device
R2: secondary hydrolysis device
S: solid-liquid separation device
V, VP: valves
W: washing solution supply device
VAC: decompression device
28: ceramic filter treatment solution transfer line
29: ceramic filter treatment solution transfer line
30: cation exchange resin supply line
31: anion exchange resin supply line
32: cation exchange resin supply line
33: anion exchange resin supply line
34: liquid sugar extraction line
35: two-component separation chromatographic separation device supply line
36: ion exchange resin supply line
37: aqueous solution extraction line
38: liquid sugar recovery line
39: concentrate transfer line
40: vapor phase transfer line
41: condensate extraction line
42: vapor phase transfer line
43: condensate extraction line
44: concentrate transfer line
45: ceramic filter treatment solution transfer line
46: concentrate transfer line
47: ceramic filter treatment solution transfer line
48: vapor phase transfer line
49: condensate extraction line
CE: ceramic filter
E: concentration device
AC: activated carbon column
CA: cation exchange resin
AN: anion exchange resin
SC: two-component separation chromatographic separation device
IO: ion exchange resin
C: condenser
NE: neutralization step

The invention claimed is:

1. A method for manufacturing monosaccharides, oligosaccharides, and furfurals comprising: subjecting a biomass to primary hydrolysis under pressurization and heating conditions under which monosaccharides, oligosaccharides, and/or furfurals are produced while continuously supplying an aqueous suspension of a raw material suspension of the biomass from a supply port of a continuous primary hydrolysis device and moving the biomass suspension through the device, continuously discharging the primary hydrolysis suspension from a discharge port of the continuous primary hydrolysis device, and continuously extracting the primary hydrolysis solution separated from the primary hydrolysis suspension in the device from an intermediate extraction port equipped with a solid-liquid separation device provided at any position between the supply port and the discharge port of the continuous primary hydrolysis device in a state in which the temperature and pressurization of primary hydrolysis are maintained; extracting the primary hydrolysis solution from the primary hydrolysis suspension in the continuous primary hydrolysis device and feeding the solution to a secondary hydrolysis device; performing secondary hydrolysis with the secondary hydrolysis device under conditions in which the ratio (%) of the mass of all pentoses in the secondary hydrolysis solution discharged from a discharge port of the secondary hydrolysis device with respect to the mass of all pentoses contained in the solution supplied to the secondary hydrolysis device containing the primary hydrolysis solution [(mass of all pentoses in the secondary hydrolysis solution discharged from the discharge port of the secondary hydrolysis device/mass of all pentoses contained in the solution supplied to the secondary hydrolysis device)× 100] is from 1 to 30%; and separating the secondary hydrolysis solution obtained by the secondary hydrolysis device into a vapor phase containing furfurals and a liquid phase containing sugars.

2. The method according to claim 1, wherein hydrolysis solution containing monosaccharides, oligosaccharides, and/or furfurals is extracted from a hydrolysis suspension in the hydrolysis device via intermediate extraction ports equipped with solid-liquid separation devices provided at two or more intermediate positions at a distance in the vertical direction between the supply port and the discharge port of the continuous primary hydrolysis device, while simultaneously supplying an aqueous liquid to the hydrolysis device from an aqueous liquid supply port formed between the respective intermediate extraction ports; and thereby maintaining the hydrolysis conditions inside the hydrolysis device.

3. The method according to claim 2, comprising separating the primary hydrolysis suspension extracted from the discharge port of the continuous primary hydrolysis device, to which a hydrolysis suspension extraction conduit provided with a solid-liquid separation device is connected, into a solid and a liquid; and recovering an additional amount of the hydrolysis solution containing monosaccharides, oligosaccharides, and/or furfurals.

4. The method according to claim 1, comprising obtaining a secondary hydrolysis solution with an increased content ratio of at least one type selected from the monosaccharide component, the oligosaccharide component, and the furfural component contained in the primary hydrolysis solution by continuously extracting the primary hydrolysis solution separated from the primary hydrolysis suspension in the continuous primary hydrolysis device in a state in which the temperature and pressure of primary hydrolysis are maintained, and subjecting the solution to secondary hydrolysis by a secondary hydrolysis device under pressure at 120 to 230° C. for a retention time of 1 to 180 minutes.

5. The method according to claim 4, comprising separating a vapor phase containing produced furfural from a liquid phase by feeding the secondary hydrolysis solution obtained from the secondary hydrolysis device to a concentration/separation device and distilling the solution; recovering a furfural-containing aqueous solution by condensing the separated vapor phase; and recovering monosaccharides and oligosaccharides from the liquid phase after distillation.

6. The method according to claim 5, comprising increasing the content ratio of the furfural component by circulating at least part of the liquid phase remaining after the vapor phase is separated by the distillation of the secondary hydrolysis solution in the concentration/separation device to the supply port of the secondary hydrolysis device.

7. The method according to claim 5, comprising adding at least part of the liquid phase remaining after the vapor phase is separated by the distillation of the secondary hydrolysis solution in the concentration/separation device to the aqueous suspension of the biomass supplied to the primary hydrolysis device.

8. The method according to claim 1, comprising adding at least part of the liquid phase containing sugars separated from the secondary hydrolysis solution to the biomass raw material suspension supplied to the primary hydrolysis device.

9. The method according to claim 1, comprising extracting the primary hydrolysis solution separated from the primary hydrolysis suspension in the continuous primary hydrolysis device in a state in which the temperature and pressure of primary hydrolysis are maintained; feeding the primary hydrolysis solution to a secondary hydrolysis device and subjecting the solution to secondary hydrolysis; separating secondary hydrolysates in the secondary hydrolysis device into a liquid phase containing monosaccharides and oligosaccharides and a vapor phase containing furfurals; and further feeding the vapor phase to a distillation device, treating the vapor phase, and recovering the vapor phase as a concentrate containing furfurals.

10. The method according to claim 9, comprising circulating at least part of the liquid phase containing monosaccharides and oligosaccharides extracted from the secondary hydrolysis device to the secondary hydrolysis device and subjecting the liquid phase to hydrolysis together with the primary hydrolysis solution.

11. The method according to claim 1, comprising transferring the discharge suspension discharged from the discharge port of the continuous primary hydrolysis device to a separation device for recovering the hydrolyzed biomass via a discharge suspension transfer conduit and then separating the suspension into the hydrolyzed biomass and a hydrolysis solution containing hydrolysates; recovering the hydrolyzed biomass; extracting the hydrolysis solution from the separation device to a circulation conduit for circulating and combining the hydrolysis solution with the discharge suspension discharged from the bottom of the hydrolysis device; and circulating and combining the remaining part with the discharge suspension discharged from the bottom of the hydrolysis device while recovering part of the suspension as a hydrolysate from an intermediate part of the circulation conduit.

12. The method according to claim 11, comprising adding an aqueous liquid to the hydrolysis solution of the remaining part recovered as part of the hydrolysis solution containing the hydrolysate in the circulation conduit, which was separated from the discharge suspension by a separation device and extracted to the circulation conduit.

13. The method according to claim 1, comprising continuously extracting the primary hydrolysis solution separated from the primary hydrolysis suspension in the continuous primary hydrolysis device in a state in which the temperature and pressure of primary hydrolysis are maintained; feeding the solution to a concentration/separation device and subjecting the solution to flash distillation; separating a vapor phase containing produced furfural from a liquid phase; and condensing the separated vapor phase to obtain an aqueous solution containing furfural.

14. The method according to claim 1, comprising supplying an aqueous washing solution to the hydrolysis device from the vicinity of the discharge port of the continuous primary hydrolysis device so as to bring the solution into contact with a hydrolysis suspension in a countercurrent manner between the intermediate extraction port equipped with a solid-liquid separation device and the discharge port.

15. The method according to claim 1, wherein the biomass is a wood biomass.

* * * * *